US012661415B2

(12) United States Patent
Liu et al.

(10) Patent No.: US 12,661,415 B2
(45) Date of Patent: Jun. 23, 2026

(54) ISOINDOLINONE COMPOUNDS AND IMAGING AGENTS FOR IMAGING HUNTINGTIN PROTEIN

(71) Applicant: CHDI Foundation, Inc., New York, NY (US)

(72) Inventors: Longbin Liu, Thousand Oaks, CA (US); Celia Dominguez, Los Angeles, CA (US); Jonathan Bard, New York, NY (US); Christopher John Brown, Abingdon (GB); Xuemei Chen, Voorheesville, NY (US); Daniel Clark-Frew, Wantage (GB); Matthew Robert Mills, Wantage (GB); Peter David Johnson, Oxfordshire (GB); Elise Gadouleau, Didcot (GB)

(73) Assignee: CHDI Foundation, Inc., New York, NY (US)

( * ) Notice: Subject to any disclaimer, the term of this patent is extended or adjusted under 35 U.S.C. 154(b) by 956 days.

(21) Appl. No.: 17/715,661

(22) Filed: Apr. 7, 2022

(65) Prior Publication Data

US 2022/0339302 A1 Oct. 27, 2022

Related U.S. Application Data

(60) Provisional application No. 63/172,617, filed on Apr. 8, 2021.

(51) Int. Cl.

| | |
|---|---|
| ***A61K 51/04*** | (2006.01) |
| ***A61P 25/28*** | (2006.01) |
| ***C07D 401/14*** | (2006.01) |

(52) U.S. Cl.

CPC ...... *A61K 51/0459* (2013.01); *A61K 51/0455* (2013.01); *A61P 25/28* (2018.01); *C07D 401/14* (2013.01); *C07B 2200/05* (2013.01)

(58) Field of Classification Search

CPC . A61K 51/0459; A61K 51/0455; A61P 25/28; C07D 401/14; C07B 2200/05

USPC ........................................................ 424/1.89

See application file for complete search history.

(56) References Cited

U.S. PATENT DOCUMENTS

| | | | | |
|---|---|---|---|---|
| 10,479,802 | B2 | 11/2019 | Dominguez et al. | |
| 10,907,197 | B2 | 2/2021 | Dominguez et al. | |
| 11,059,836 | B2 | 7/2021 | Dominguez et al. | |
| 11,071,793 | B2 | 7/2021 | Dominguez et al. | |
| 12,036,291 | B2 | 7/2024 | Dominguez et al. | |
| 12,258,355 | B2 | 3/2025 | Dominguez et al. | |
| 2017/0283436 | A1* | 10/2017 | Dominguez ....... | A61K 51/0459 |

FOREIGN PATENT DOCUMENTS

| | | | | |
|---|---|---|---|---|
| WO | 2016/033445 | A1 | 3/2016 | |
| WO | WO-2016033436 | A1 * | 3/2016 | ......... A61K 51/0446 |
| WO | WO-2016033460 | A1 * | 3/2016 | ......... A61K 51/0419 |

OTHER PUBLICATIONS

International Search Report and Written Opinion for International Application No. PCT/US2022/023861, Jun. 29, 2022, 16 pages.

Liu Longbin et al., "Imaging Mutant Huntingtin Aggregates: Development of a Potential PET Ligand", Journal of Medicinal Chemistry, vol. 63, No. 15, Jul. 14, 2020, pp. 8608-8633.

PubChem database CID: 118903129 (Apr. 9, 2016), downloaded from https://pubchem.ncbi.nlm.nih.gov/compound/118903129 on May 30, 2025.

* cited by examiner

*Primary Examiner* — Michael G. Hartley
*Assistant Examiner* — Sean R Donohue
(74) *Attorney, Agent, or Firm* — Sheppard Mullin Richter & Hampton LLP

(57) ABSTRACT

Provided herein are certain isoindolinone compounds and imaging agents useful for detecting a disease or condition associated with protein aggregation, compositions thereof, and methods of their use.

10 Claims, 3 Drawing Sheets

ISOINDOLINONE COMPOUNDS AND IMAGING AGENTS FOR IMAGING HUNTINGTIN PROTEIN

CROSS REFERENCE TO RELATED APPLICATIONS

This application claims priority to U.S. Provisional Application No. 63/172,617, filed Apr. 8, 2021, which is incorporated herein by reference for all purposes.

FIELD

Provided herein are compounds and imaging agents useful for detecting, treating, or preventing a disease or condition associated with protein aggregation, compositions thereof, and methods of their use.

BACKGROUND

The advent of molecular imaging approaches, such as positron emission tomography (PET) and single photon emission computed tomography (SPECT), has enabled measurements of molecular and cellular mechanisms throughout the body in preclinical and clinical settings. Such measurements have widespread diagnostic utility and their use for evaluation of treatment responses and to assist drug development is expanding rapidly. The introduction of high-resolution molecular imaging technology is considered by many experts as a major breakthrough.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

Molecular probes labeled with positron-emitting radionuclides and associated PET imaging assays are under development to target, detect, visualize, and quantify various extracellular and intracellular molecules and processes associated with various diseases.

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. HD is caused by the expanded CAG trinucleotide repeat in the exon-1 region of the huntingtin gene (HTT). The resulting polyglutamate domain expansion may induce misfolding and conformational changes in the mutant huntingtin (mHTT) protein, leading to formation of protein aggregates. HD has a prevalence of 5-10 cases per 100,000 worldwide, which makes it the most common inherited and monogenic neurodegenerative disorder.

Consistent with other medical conditions, treatments for HD are ideally initiated at or before early signs of disease. Thus, early indicators of disease onset and reliable pharmacodynamic biomarkers of disease progression are highly desirable.

In view of the central role of the accumulation of aggregated forms of proteins in the pathogenesis of neurodegenerative conditions including HD, there is a need for molecules that bind to such proteins with high sensitivity and specificity and that permit molecular imaging.

SUMMARY

The present disclosure relates to compounds useful for imaging Huntingtin protein. Some embodiments provide for a compound of Formula I as described herein, wherein the compound is optionally labeled with one or more radioactive isotopes. In some embodiments, the compound of Formula I contains one or more positron-emitting radioactive isotopes selected from $^{11}C$, $^{13}N$, $^{15}O$, and $^{18}F$.

In some embodiments, an imaging agent comprising the compound of Formula I, or an isotopically enriched analog, pharmaceutically acceptable salt, prodrug, tautomer, stereoisomer, or a mixture of stereoisomers thereof, is provided.

Also provided are imaging agents comprising a compound described herein, wherein the compound is labeled with one or more positron-emitting radionuclides. In some embodiments, the compound contains one or more positron-emitting radionuclides selected from $^{11}C$, $^{13}N$, $^{15}O$, and $^{18}F$.

Also provided is a method of detecting the presence or absence of a protein susceptible to aggregation in an individual comprising administering an effective amount of a compound described herein or an imaging agent comprising a compound described herein, and generating an image of a body part or body area of the individual.

In some embodiments, provided is a compound or an imaging agent for use in detecting the presence or absence of a protein susceptible to aggregation in an individual, wherein the use comprises administering an effective amount of a compound or an imaging agent described herein to an individual, and generating an image of a body part or body area of the individual.

In some embodiments, provided is a compound or an imaging agent for use as described herein, wherein generating an image of a body part or body area of the individual comprises detecting the presence or absence of a protein susceptible to aggregation in the image. In some embodiments, provided is a compound or an imaging agent for use as described herein, wherein the protein susceptible to aggregation is huntingtin protein (HTT protein). In some embodiments, provided is a compound or an imaging agent for use as described herein, wherein the HTT protein is found in basal ganglia.

In some embodiments, provided is a compound or an imaging agent for use as described herein, wherein the presence or absence of a protein aggregate corresponds to the presence or absence of a neurodegenerative disease.

In some embodiments, provided is a compound or an imaging agent for use as described herein, wherein the neurodegenerative disease is selected from Alzheimer's disease, amyotrophic lateral sclerosis, Huntington's disease, Parkinson's disease, Prion disease, and spinocerebellar ataxias. In some embodiments, provided is a compound or an imaging agent for use as described herein, wherein the neurodegenerative disease is Huntington's disease (HD).

In some embodiments, provided is a compound or an imaging agent for use as described herein, wherein the effective amount of the imaging agent comprises from about 0.1 to about 20 mCi. In some embodiments, provided is a compound or an imaging agent for use as described herein, wherein the effective amount of the imaging agent comprises about 10 mCi.

In some embodiments, provided is a compound or an imaging agent for use as described herein, wherein generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof. In some embodiments, provided is a compound or an imaging agent for use as described herein, wherein generating an image comprises PET imaging.

In some embodiments, provided is a compound or an imaging agent for use as described herein, wherein the HTT protein is present as oligomers or aggregates, or a combination thereof. In some embodiments, provided is a compound or an imaging agent for use as described herein, wherein the HTT protein is mutant.

In some embodiments, provided is a compound or an imaging agent for use as described herein, wherein the body part or body area is head, spinal cord, limb, thorax, or abdomen. In some embodiments, provided is a compound or an imaging agent for use as described herein, wherein the body part or body area is brain.

DETAILED DESCRIPTION

Figure 1:
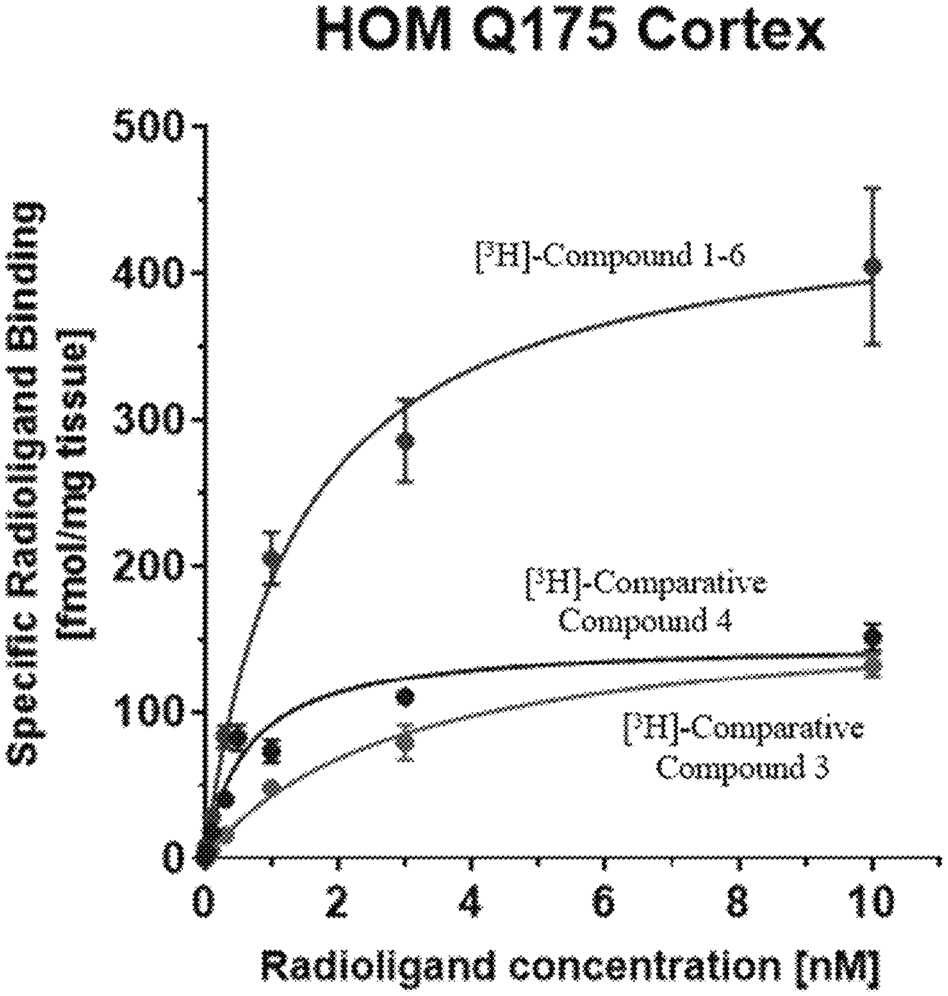
FIG. 1 shows specific and saturation binding of tested radioligand compounds, over a range of concentrations, determined in cortex tissue of the HD mouse model 12-month-old HOM zQ175.

The following description sets forth exemplary embodiments of the present technology. It should be recognized, however, that such description is not intended as a limitation on the scope of the present disclosure but is instead provided as a description of exemplary embodiments.

Definitions

As used in the present specification, the following words, phrases and symbols are generally intended to have the meanings as set forth below, except to the extent that the context in which they are used indicates otherwise.

A compound described herein refers to a compound, or an isotopically labeled analog, pharmaceutically acceptable salt, solvate, prodrug, stereoisomer, or mixture of stereoisomers thereof, of any formula described herein, including those of Formula I, II, III, IV, V, VI, VII, VII, IX, X, XI, XII, XIII, XIV, XV, XVI, or XVII or a compound described anywhere herein including the Examples, or a compound of Table 1 or a labeled isomer of such compound as defined herein, or an imaging agent or pharmaceutical composition comprising such compound or labeled compound.

A dash ("-") that is not between two letters or symbols is used to indicate a point of attachment to a parent structure for a substituent. For example, $—C(O)NH_2$ is attached to a parent structure through the carbon atom. A dash at the front or end of a chemical group is a matter of convenience; chemical groups may be depicted with or without one or more dashes without losing their ordinary meaning. A wavy line drawn through a bond in a structure indicates a specified point of attachment. Unless chemically or structurally required, no directionality or stereochemistry is indicated or implied by the order in which a chemical group is written or named.

The prefix "$C_{u-v}$" indicates that the following group has from u to v carbon atoms, exclusive of further substitution. For example, "$C_{1-6}$ alkyl" indicates an alkyl group having from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plurals thereof unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 9 carbon atoms (i.e., $C_{1-9}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $—(CH_2)_3CH_3$), sec-butyl (i.e., $—CH(CH_3)CH_2CH_3$), isobutyl (i.e., $—CH_2CH(CH_3)_2$) and tert-butyl (i.e., $—C(CH_3)_3$); and "propyl" includes n-propyl (i.e., $—(CH_2)_2CH_3$) and isopropyl (i.e., $—CH(CH_3)_2$).

Alternative chemical names known to those of skill in the art may be used in lieu of the terms provided herein. For example, a divalent group such as a divalent "alkyl" group, a divalent "aryl" group, etc., may also be referred to as an "alkylene" or an "arylene" group, respectively. Also, unless indicated explicitly otherwise (for example, by a dash), where combinations of groups are referred to herein as one moiety, e.g., arylalkyl or aralkyl, the last mentioned group contains the atom by which the moiety is attached to the rest of the molecule.

"Alkenyl" refers to a hydrocarbon group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl), and isoprenyl.

"Alkynyl" refers to an hydrocarbon group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having a triple bond and a double bond.

"Alkoxy" refers to a group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylamino" refers to a group "alkyl-NH—". Examples of alkylamino groups include, e.g., methylamino, ethylamino, iso-propylamino, tert-butylamino, and n-hexylamino. "Dialkylamino" refers to a group "$(alkyl)_2N—$". Examples of dialkylamino groups include, e.g., dimethyl-amino, diethylamino, (iso-propyl)(methyl)amino, (n-pentyl)(tert-butyl)amino, and di-n-hexylamino.

"Alkylthio" refers to a group "alkyl-S—". "Alkylsulfinyl" refers to the group "alkyl-S(O)—". "Alkylsulfonyl" refers to a group "alkyl-$S(O)_2$—". "Alkylsulfonylalkyl" refers to -alkyl-$S(O)_2$-alkyl.

"Acyl" refers to a group —C(O)$R^y$, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to a group —OC(O)$NR^yR^z$ and an "N-amido" group which refers to a group —$NR^y$C(O)$R^z$, wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to a group —$NR^yR^z$ wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein. In some embodiments, "amino" refers to a group $NH_2$.

"Amidino" refers to a group —C(=$NR^y$)$NR^z_2$, wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl) or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to a group "aryl-alkyl-".

"Carbamoyl" refers to both an "O-carbamoyl" group which refers to a group —O—C(O)$NR^yR^z$ and an "N-carbamoyl" group which refers to a group —$NR^y$C(O)O$R^z$, wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Carboxyl ester" or "ester" refer to both —OC(O)$R^x$ and —C(O)O$R^x$, wherein $R^x$ is alkyl, alkenyl, alkynyl, haloalkyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ ring carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cyclohexenyl, cycloheptyl and cyclooctyl. Polycyclic groups include, for example, bicyclo[2.2.1]heptanyl, bicyclo[2.2.2]octanyl, adamantyl, norbornyl, norbornenyl, decalinyl, 7,7-dimethyl-bicyclo[2.2.1]heptanyl and the like. Further, the term cycloalkyl is intended to encompass any non-aromatic ring system which may include a fused aryl ring, regardless of the attachment to the remainder of the molecule. Still further, cycloalkyl also includes "spirocycloalkyl," for example spiro[2.5]octanyl, spiro[4.5]decanyl, or spiro[5.5]undecanyl. When there are two positions for substitution on a carbon atom in a parent structure, cycloalkyl as a substituent group may include spirocycloalkyl. A cycloalkyl may be substituted at its carbon atom of attachment to a parent structure.

"Cycloalkoxy" refers to a group "—O-cycloalkyl."

"Cycloalkylalkyl" refers to a group "cycloalkyl-alkyl-".

"Guanidino" refers to —$NR^y$C(=$NR^z$)$NR^yR^z$, wherein each $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Imino" refers to a group —C(=$NR^y$)$R^z$, wherein $R^y$ and $R^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

"Imido" refers to a group —C(O)$NR^y$C(O)$R^z$, wherein $R^y$ and $R^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

"Halogen" or "halo" refers to a substituent atom of group VIIA of the periodic table, such as fluoro, chloro, bromo or iodo.

"Haloalkyl" refers to an unbranched or branched alkyl group as defined above, wherein one or more (e.g., 1 to 6 or 1 to 3) hydrogen atoms, up to and including all hydrogen atoms, are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. A perhaloalkyl group is a haloalkyl group in which every hydrogen substituent is replaced by halo. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6 or 1 to 3) hydrogen atoms, up to and including all hydrogen atoms, are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms of the alkyl chain (and any associated hydrogen atoms) are each independently replaced with the same or different heteroatomic group, provided the point of attachment to the remainder of the molecule is through a carbon atom. The term "heteroalkyl" includes unbranched or branched saturated chains having carbon and heteroatoms. By way of example, 1, 2 or 3 carbon atoms may be independently replaced with the same or different heteroatomic group. Heteroatomic groups include, but are not limited to, —$NR^y$—, —$C(O)NR^y$—, —$NR^yC(O)$—, —O—, —S—, —S(O)—, and —$S(O)_2$—, wherein $R^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of heteroalkyl groups include, e.g., ethers (e.g., —$CH_2OCH_3$, —$CH(CH_3)OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.) and aminoalkyls (e.g., —$CH_2NR^yCH_3$, —$CH(CH_3)NR^yCH_3$, —$CH_2CH_2NR^yCH_3$, —$CH_2CH_2NR^yCH_2CH_2NR^yCH_3$, etc., where $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring or multiple fused rings, with one or more ring heteroatoms independently selected from nitrogen, oxygen, and sulfur, and may comprise one or more (e.g., 1 to 3) N-oxide (—$O^-$) moieties. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring system, having a single or multiple fused rings containing at least one ring heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to a group "heteroaryl-alkyl-".

"Heterocyclyl" refers to a saturated or partially unsaturated cyclic alkyl group, with one or more ring heteroatoms independently selected from nitrogen, oxygen and sulfur, wherein the nitrogen or sulfur atoms are optionally oxidized to form an N-oxide, a sulfinyl (—S(O)—), or a sulfoxide (—$S(O)_2$—). The term "heterocyclyl" includes heterocycloalkenyl groups (i.e., a heterocyclyl group having at least one double bond), bridged-heterocyclyl groups, fused-heterocyclyl groups, spiro-heterocyclyl, and oxo-heterocyclyl groups. A heterocyclyl may be a single ring or multiple rings wherein the multiple rings may be fused, bridged or spiro. Regardless of substituent groups listed, a heterocyclyl may comprise one or more (e.g., 1 to 3) oxo (=O) or N-oxide (—O—) moieties unless stated otherwise. A heterocyclyl can be bound through a carbon atom or a heteroatom as valency permits. Further, the term heterocyclyl encompasses any ring system including a non-aromatic ring or ring system containing at least one heteroatom, which ring may be fused to an aryl or heteroaryl ring, regardless of the attachment to the remainder of the molecule. A heterocyclyl may have a charged resonance structure that is aromatic (e.g., pyridin-2(1H)-on-1-yl). As used herein, a heterocyclyl may include 3 to 14 ring atoms, 3 to 10 ring atoms, 3 to 6 ring atoms, or 5 to 6 ring atoms, and/or 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiro-heterocyclyl." Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. When there are two positions for substitution on a carbon atom in a parent structure, heterocyclyl as a substituent group may include spiro-heterocyclyl. Examples of bridged-heterocyclyl rings include, but are not limited to, 2,5-diazabicyclo[2.2.1]heptane, 2-oxa-5-azabicyclo[2.2.1]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system. An "oxo-heterocyclyl" group is a heterocyclyl including at least one oxo substituent (e.g., 1, or 1 to 2 oxo substituents), whether or not additional substituents are permitted (i.e., an unsubstituted oxo-heterocyclyl includes an oxo and no other substitution). In some embodiments, an oxo-heterocyclyl includes a cyclic amide moiety.

"Heterocyclylalkyl" refers to a group "heterocyclyl-alkyl-."

"Oxime" refers to a group —$CR^y$(=NOH) wherein $R^y$ is hydrogen, alkyl, alkenyl, alkynyl, haloalkyl, cycloalkyl, heterocyclyl, aryl, heteroalkyl or heteroaryl; each of which may be optionally substituted, as defined herein.

"Sulfonyl" refers to a group —$S(O)_2R^y$, where $R^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to a group —$S(O)R^y$, where $R^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —$SO_2NR^yR^z$ and —$NR^ySO_2R^z$, where $R^y$ and $R^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to a group which is unsubstituted or substituted.

The term "substituted" used herein refers to a group in which any one or more (e.g., 1 to 5 or 1 to 3) hydrogen atoms is replaced by a non-hydrogen group such as, but not limited to alkyl, alkenyl, alkynyl, alkoxy, alkylthio, acyl, amido, amino, amidino, aryl, arylalkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, —$NHNH_2$, =$NNH_2$, imino, imido, hydroxy, oxo, oxime, nitro, sulfonyl, sulfinyl, alkylsulfonyl, alkylsulfinyl, thiocyanate, —S(O)OH, —$S(O)_2OH$, sulfonamido, thiol, thioxo, N-oxide or —$Si(R^y)_3$, wherein each $R^y$ is independently hydrogen, alkyl, alkenyl, alkynyl, haloalkyl, heteroalkyl, cycloalkyl, aryl, heteroaryl, or heterocyclyl.

In certain embodiments, "substituted" refers to a group in which one or more (e.g., 1 to 5 or 1 to 3) hydrogen atoms are independently replaced with deuterium, halo, cyano, hydroxyl, imino, nitro, azido, oxo, thioxo, alkyl, alkenyl, alkynyl, haloalkyl, alkoxy, thioalkyl, haloalkoxy, cycloalkyl, heterocyclyl, N-heterocyclyl, heterocyclylalkyl, aryl, arylalkyl, heteroaryl, heteroarylalkyl, —$NR^gR^h$, —$NR^gC(=O)R^h$, —$NR^gC(=O)NR^gR^h$, —$NR^gC(=O)OR^h$, —$NR^gS(=O)_{1-2}R^h$, —$C(=O)R^g$, —$C(=O)OR^g$, —$OC(=O)OR^g$, —$OC(=O)R^g$, —$C(=O)NR^gR^h$, —$OC(=O)NR^gR^h$, —$OR^g$, —$SR^g$, —$S(=O)R^g$, —$S(=O)_2R^g$, —$OS(=O)_{1-2}R^g$, —$S(=O)_{1-2}R^g$, —$NR^gS(=O)_{1-2}NR^gR^h$, =$NSO_2R^g$, =$NOR^g$, —$S(=O)_{1-2}NR^gR^h$, —$SF_5$, or —$SCF_3$. In certain embodiments, "substituted" also means a group in which one or more (e.g., 1 to 5 or 1 to 3) hydrogen atoms are replaced with —$C(=O)R^g$, —$C(=O)OR^g$, —$C(=O)NR^gR^h$, —$CH_2SO_2R^g$, or —$CH_2SO_2NR^gR^h$. In the foregoing, $R^g$ and $R^h$ are the same or different and independently hydrogen, alkyl, alkenyl, alkynyl, alkoxy, thioalkyl, aryl, arylalkyl, cycloalkyl, cycloalkylalkyl, haloalkyl, heterocyclyl, heterocyclylalkyl, heteroaryl, and/or heteroarylalkyl, or two of $R^g$ and $R^h$ are taken together with the atoms to which they are attached to form a heterocyclyl ring optionally substituted with oxo, halo, or alkyl wherein the alkyl is optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended to arise from the above definitions. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to encompass compounds having chemically unfeasible or unisolable substitution patterns (e.g., methyl substituted with 5 fluorines or heteroaryl groups having three consecutive oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein is intended to represent unlabeled forms as well as "isotopically enriched analogs" of the compounds. Isotopically enriched forms of compounds may also be referred to as "labeled." Isotopically enriched analogs have structures depicted herein, except that one or more atoms are enriched in an isotope having a selected atomic mass or mass number. Examples of isotopes that can be incorporated into the compounds described herein include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Generally, an isotopically enriched analog includes compounds having any isotopic enrichment above the natural abundance of the isotope (e.g., at Earth's surface). Various isotopically labeled compounds are included in the present disclosure, for example those into which radioactive isotopes such as $^{3}H$, $^{18}F$, $^{11}C$, and $^{14}C$ are incorporated. Compounds labeled with $^{18}F$, $^{3}H$, or $^{11}C$ may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds may exhibit increased resistance to metabolism and are thus may be useful for increasing the half-life of any compound when administered to a mammal, particularly a human See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Where a compound is described as a deuterated analog, the compound may be drawn with deuterium as a substituent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen and its isotopes at their natural abundances.

In many cases, the compounds of this disclosure are capable of forming acid and/or base salts by virtue of the presence of amino and/or carboxyl groups or groups similar thereto.

Provided also are isotopically enriched analogs, pharmaceutically acceptable salts, prodrugs, tautomers, stereoisomers, and mixtures of stereoisomers of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a compound described herein refers to salts that retain the biological effectiveness and properties of the given compound and which are not biologically or otherwise undesirable. "Pharmaceutically acceptable salts" or "physiologically acceptable salts" of compounds described herein include, for example, acid addition salts obtained by interacting a compound with a basic functional group with an acid, and base addition salts obtained by interacting a compounds with an acidic functional group with a base. If the compound is obtained as an acid addition salt, the free base can be obtained by basifying a solution of the acid salt. Conversely, if the compound is a free base (e.g., of an amine), an addition salt may be produced by dissolving the free base in a suitable organic solvent and treating the solution with an acid. Those skilled in the art will recognize various synthetic methodologies that may be used to prepare nontoxic pharmaceutically acceptable addition salts. Pharmaceutically acceptable acid addition salts of compounds described herein may be prepared from inorganic and organic acids. Suitable inorganic acids include, e.g., hydrochloric acid, hydrobromic acid, sulfuric acid, nitric acid, phosphoric acid and the like. Suitable organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), di(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri (substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), cyclic amines (e.g., piperidine, piperazine, 1,4-diazabicyclo[2.2.2]octane), aromatic amines (e.g., pyridine, quinoline), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Some compounds described herein may exist as tautomers. For example, where a compound is drawn as including an amide, the compound may exist as an imidic acid tautomer, and where a compound is drawn as including a ketone, the compound may also exist as an enol tautomer. Regardless of which tautomer is shown and regardless of the nature of the equilibrium among tautomers, the compounds are understood by one of ordinary skill in the art to comprise both tautomers. Thus, for example, the amide containing compounds are understood to include their imidic acid tautomers, and the imidic acid containing compounds are understood to include their amide tautomers.

The compounds described herein may include an asymmetric center and may thus give rise to enantiomers, diastereomers, and other stereoisomeric forms that may be defined, in terms of absolute stereochemistry, as (R)– or (S)–, or as (D)– or (L)– for amino acids. Compounds described herein are meant to include all such possible isomers, as well as their racemic and optically pure forms. Optically active (+) and (–), (R)– and (S)–, or (D)– and (L)– isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain double bonds or other centers of geometric asymmetry, and unless specified otherwise, it is intended that the compounds include both cis- and trans- or E- and Z-geometric isomers.

A "stereoisomer" refers to one of a set of compounds made up of the same atoms bonded by the same bonds but having different three-dimensional structures. Various stereoisomers and mixtures thereof are contemplated including "enantiomers," which refers to stereoisomeric compounds that are non-superimposable mirror images of one another.

A "diastereomer" is one of a set of stereoisomers that have at least two asymmetric atoms that are not mirror-images of each other.

A "prodrug" is any molecule which releases a putatively active parent drug according to a compound described herein in vivo when such prodrug is administered to a mammalian subject. A prodrug may be a form of a compound described herein modified in such a way that the modifications may be cleaved in vivo to release the parent compound. Prodrugs may be prepared by modifying functional groups present in the compound described herein in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

In some embodiments, the term "neurodegenerative disease" refers to a disease or condition in which the function of a subject's nervous system becomes impaired. Examples of neurodegenerative diseases include those described herein.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The above-listed terms also include in vitro and ex vivo methods.

As used herein the terms "group," "moiety," "radical," "substituent," and "fragment" are synonymous and are intended to indicate portions of molecules attachable to other portions of molecules, e.g., through an indicated attachment point or bond.

The term "active agent" is used to indicate a compound which has biological activity in the treatment, amelioration, or prevention of a disease or condition. In some embodiments, an "active agent" is a compound or an isotopically labeled analog, pharmaceutically acceptable salt, solvate, prodrug, stereoisomer, or mixture of stereoisomers thereof, having pharmaceutical utility. For example an active agent may be an anti-neurodegenerative therapeutic.

The term "effective amount" means an amount, for example, of a compound described herein, sufficient to bring about a desired response in an individual or patient. In the context of use of an imaging agent, an effective amount may be an amount needed to produce an image having diagnostic or therapeutic utility. The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease described herein. The (therapeutically) effective amount may vary depending on the subject, and disease or condition being treated, the weight and age of the subject, the severity of the disease or condition, and the manner of administering, which can readily be determined by one of ordinary skill in the art.

The term "huntingtin protein" or "HTT protein" as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "protein aggregate," as used herein refers to an aggregation of protein which may be, for example, an insoluble fibrous amyloid comprising mis-folded HTT protein molecules ("HTT protein aggregate") or mis-folded β-amyloid protein molecules ("β-amyloid aggregate"). A "protein susceptible to aggregation" is a protein that is capable of forming such aggregates, in its wild type or in a mutated form.

The term "imaging agent," as used herein, refers to a compound described herein labeled with one or more positron-emitting isotopes or radionuclides, or a composition comprising the labeled compound. A positron-emitter labeled compound need only be enriched with a detectable isotope to a degree that permits detection with a technique suitable for the particular application.

The term "PET imaging" (which may be referred to as positron emission tomography imaging), as used herein, refers to the use of a positron-emitter labeled compound to produce images of internal structures of the human or animal body.

The term "positron-emitting radionuclide," as used herein, refers to a radioactive isotope that exhibits particular type of radioactive decay referred to as 13+ decay, in which a proton inside a radionuclide nucleus is converted into a neutron while releasing a positron and an electron neutrino ($v_e$). Some examples of positron-emitting radionuclides include $^{15}O$, $^{13}N$, $^{11}C$, $^{18}F$, $^{76}Br$, and $^{124}I$.

The term "labeled," as used herein, refers to a compound which is associated with one or more positron-emitting radionuclides in greater than natural abundance. For example, a labeled compound described herein may contain one or more positron-emitting radionuclides, wherein an atom in the molecule (including an atom in an indicated substituent) is present as a positron-emitting isotope.

The term "tomography," as used herein, refers to a process of imaging by sections. The images may be looked at individually, as a series of two-dimensional slices or together, as a computer-generated three-dimensional representation.

In some embodiments, the term "neurodegenerative disease" refers to a disease or condition in which the function of a subject's nervous system becomes impaired. Examples of neurodegenerative diseases include those described herein.

"Treatment" or "treating" means any treatment of a disease state in a patient, including a) inhibiting the disease (e.g., decreasing one or more symptoms resulting from the disease or condition, and/or diminishing the extent of the disease or condition);
b) slowing or arresting the development of clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival).

"Prevention" or "preventing" means any treatment of a disease or condition that causes the clinical symptoms of the disease or condition not to develop. Compounds may, in some embodiments, be administered to a subject (including a human) who is at risk (e.g., carries a genetic or epigenetic marker, has engaged in an activity, or has been exposed to an environmental condition, associated with the disease or condition) or has a family history of the disease or condition.

"Subject" or "patient" refers to an animal, such as a mammal, that has been or will be the object of treatment, observation or experiment. The methods described herein may be useful in both human therapy and veterinary applications. In some embodiments, the subject or patient is a mammal. In some embodiments the subject or patient is human.

The term "Curie" (Ci) is a unit of measurement of radioactivity and has its customary meaning to those of skill in the art.

The term "diagnostic imaging," as used herein, refers to the use of electromagnetic radiation to produce images of internal structures of the human or animal body for the purpose of diagnosis.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I or any other formula are specifically embraced herein just as if each and every combination was individually and explicitly recited, to the extent that such combinations result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

List of Abbreviations and Acronyms

| δ | Chemical shift |
|---|---|
| Ac | Acetate |
| addn. | Addition |
| AIBN | Azobisisobutyronitrile |
| approx. | Approximately |
| aq | Aqueous |
| Ar | Aryl |
| ARG | Autoradiography |

-continued

List of Abbreviations and Acronyms

| δ | Chemical shift |
|---|---|
| atm | Atmosphere |
| BINAP | 2,2'-Bis(diphenylphosphino)-1,1'-binaphthyl |
| $B_{max}$ | Maximum number of binding sites |
| Bn | Benzyl |
| Boc | Tert-butyloxycarbonyl |
| BP | Binding potential |
| br | Broad |
| CMBP | Cyanomethyltributylphosphorane |
| CTRL | Control |
| d | Deuterated |
| d | Doublet |
| dd | Doublet of doublets |
| dba | Dibenzylideneacetone |
| DCE | Dichloroethane |
| DCM | Dichloromethane |
| DIBAL | Diisobutylaluminium hydride |
| DIPEA | Diisopropylethylamine |
| dppf | Bisdiphenylphosphinyl ferrocene |
| DMF | N,N-dimethylformamide |
| DMSO | Dimethyl sulfoxide |
| ELS | Evaporative light scattering |
| eq | Equivalent |
| ES | Electrospray ionization |
| Et | Ethyl |
| EtOAc | Ethyl acetate |
| EtOH | Ethanol |
| FCC | Flash column chromatography |
| $f_{u,brain}$ | Free fraction in brain |
| h | Hour(s) |
| HCl | Hydrochloric acid |
| HDGECs | HD gene-expanded carriers |
| HPLC | High performance liquid chromatography |
| $IC_{50}$ | Half maximal inhibitory concentration |
| IPA | Isopropyl alcohol |
| J | Coupling constant |
| $K_D$ | Dissociation Constant |
| LCMS | Liquid chromatography-mass spectrometry |
| LLoQ | Lower limit of quantification |
| m | Multiplet |
| Me | Methyl |
| MeCN | Acetonitrile |
| MeOH | Methanol |
| MHz | Megahertz |
| min | Minute(s) |
| MOM | methoxymethyl |
| MPLC | Medium Pressure Liquid Chromatography |
| MTBE | Methyl tert-butyl ether |
| m/z | Mass to charge ratio |
| N | Normal |
| NBS | N-bromosuccinimide |
| NFSI | N-fluoro-N-(phenylsulfonyl)benzenesulfonamide |
| NMR | Nuclear magnetic resonance |
| NSB | Non-specific binding |
| p | Para |
| PBS | Phosphate buffered saline |
| Ph | Phenyl |
| ppm | Part(s) per million |
| prep | Preparative |
| q | Quartet |
| quant. | Quantitative |
| RBA | Radioligand binding assay |
| RBF | Round bottom flask |
| ROI | Regions of interest |
| rt | Room temperature |
| RuPhos | 2-Dicyclohexylphosphino-2',6'-diisopropoxybiphenyl |
| s | Singlet |
| sat. | Saturated |
| SB | Specific binding |
| SCX | Propylsulfonic acid (non-endcapped) functionalized silica |
| SEM | Trimethylsilylethoxymethyl |
| t | Triplet |
| TAC | Time activity curve |
| TB | Total binding |
| TBAF | Tetrabutylammonium fluoride |
| TBDMS | Tert-butyldimethylsilyl |

-continued

List of Abbreviations and Acronyms

| | |
|---|---|
| δ | Chemical shift |
| tBuXPhos | 2-di-tert-butylphosphino-2',4',6'-tri-isopropyl-1,1'-biphenyl |
| TFA | Trifluoroacetic acid |
| THF | Tetrahydrofuran |
| Tr | Retention time |
| Tris | Tris(hydroxymethyl)aminomethane |
| Ts | p-Toluenesulfonyl |
| UV | Ultraviolet |
| v/v | Volume per volume |
| wt % | Weight percentage |
| WT | Wild type |
| w/v | Weight per volume |
| Xantphos | 9,9-dimethyl-4,5-bis(diphenylphosphino)xanthene |

Compounds

The present disclosure relates to compounds useful for imaging a protein susceptible to aggregation, for example, Huntingtin protein. Some embodiments provide for a compound of Formula I:

I

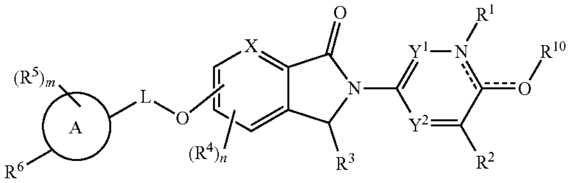

or an isotopically enriched analog, pharmaceutically acceptable salt, prodrug, tautomer, stereoisomer, or a mixture of stereoisomers thereof, wherein:

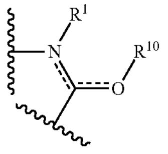
is
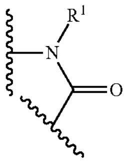
or
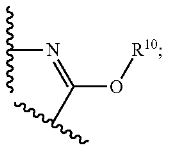

$R^1$, when present, is hydrogen, $C_{1-6}$alkyl, or $C_{1-6}$haloalkyl;

$R^{10}$, when present, is hydrogen, $C_{1-6}$alkyl, or $C_{1-6}$haloalkyl;

Ring A is 5- to 6-membered heteroaryl;

X is $CR^{11}$ or N;

$R^{11}$ is hydrogen, cyano, hydroxy, halo, $C_{1-6}$alkyl, $C_{1-6}$haloalkyl, or $C_{1-6}$alkoxy;

$Y^1$ is $CR^{12}$ or N;

$Y^2$ is $CR^{13}$ or N;

each of $R^{12}$ and $R^{13}$ is hydrogen, hydroxy, halo, $C_{1-6}$alkyl, $C_{1-6}$haloalkyl, or $C_{1-6}$alkoxy;

$R^2$ is hydrogen, hydroxy, halo, $C_{1-6}$alkyl, $C_{1-6}$haloalkyl, or $C_{1-6}$alkoxy;

L is $C_1$-$C_3$alkylene optionally substituted with 1 to 6 fluoro;

$R^3$ is hydrogen, fluoro, $C_{1-6}$alkyl, or $C_{1-6}$haloalkyl;

each $R^4$ is independently cyano, hydroxy, halo, $C_{1-6}$alkyl, $C_{1-6}$haloalkyl, or $C_{1-6}$alkoxy;

each $R^5$ is independently cyano, hydroxy, halo, $C_{1-6}$alkyl, $C_{1-6}$haloalkyl, or $C_{1-6}$alkoxy;

$R^6$ is hydrogen, cyano, hydroxy, halo, $C_{1-6}$alkyl, —$SO_2F$, or $L^1$-$R^7$;

$L^1$ is —O—, —$SO_2$—, or —$OSO_2$—;

$R^7$ is hydrogen, $C_{1-6}$alkyl, or $C_{1-6}$haloalkyl, wherein the $C_{1-6}$alkyl or $C_{1-6}$haloalkyl of $R^7$ is optionally substituted with —$SO_2$-aryl, —$OSO_2$-aryl, 1 to 6 deuterium atoms, or a combination thereof, and wherein the —$SO_2$-aryl or —$OSO_2$-aryl is further optionally substituted with cyano, hydroxy, halo, $C_{1-6}$alkyl, $C_{1-6}$haloalkyl, or $C_{1-6}$alkoxy;

m is 0, 1, 2, or 3; and n is 0, 1, or 2.

In some embodiments, the compound of Formula I is a compound of Formula II:

II

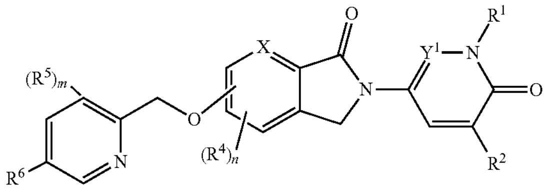

or an isotopically enriched analog, pharmaceutically acceptable salt, prodrug, tautomer, stereoisomer, or a mixture of stereoisomers thereof.

In some embodiments, the compound of Formula I is a compound of Formula III:

III

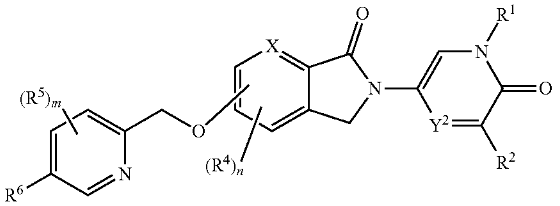

or an isotopically enriched analog, pharmaceutically acceptable salt, prodrug, tautomer, stereoisomer, or a mixture of stereoisomers thereof.

In some embodiments, the compound of Formula I is a compound of Formula IV:

IV

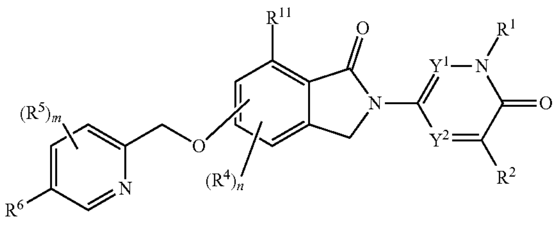

or an isotopically enriched analog, pharmaceutically acceptable salt, prodrug, tautomer, stereoisomer, or a mixture of stereoisomers thereof.

In some embodiments, the compound of Formula I is a compound of Formula V:

V

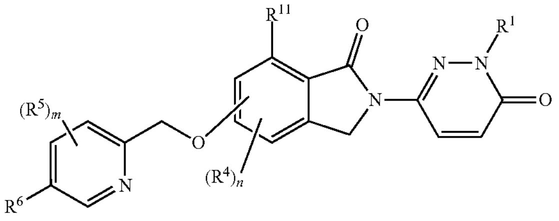

or an isotopically enriched analog, pharmaceutically acceptable salt, prodrug, tautomer, stereoisomer, or a mixture of stereoisomers thereof.

In some embodiments, the compound of Formula I is a compound of Formula VI:

VI

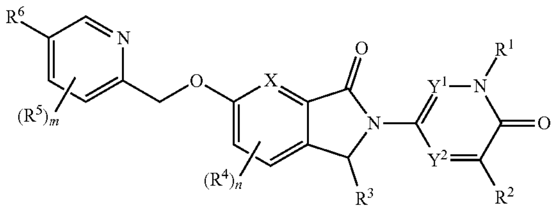

or an isotopically enriched analog, pharmaceutically acceptable salt, prodrug, tautomer, stereoisomer, or a mixture of stereoisomers thereof.

In some embodiments, the compound of Formula I is a compound of Formula VII:

VII

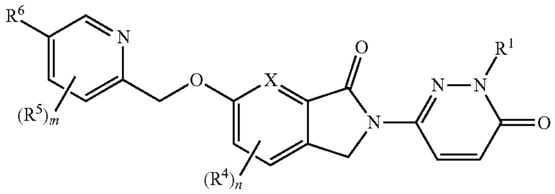

or an isotopically enriched analog, pharmaceutically acceptable salt, prodrug, tautomer, stereoisomer, or a mixture of stereoisomers thereof.

In some embodiments, the compound of Formula I is a compound of Formula VIII:

VIII

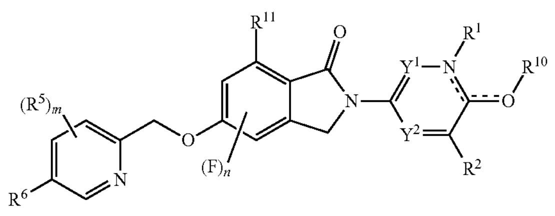

or an isotopically enriched analog, pharmaceutically acceptable salt, prodrug, tautomer, stereoisomer, or a mixture of stereoisomers thereof.

In some embodiments, the compound of Formula I is a compound of Formula IX:

IX

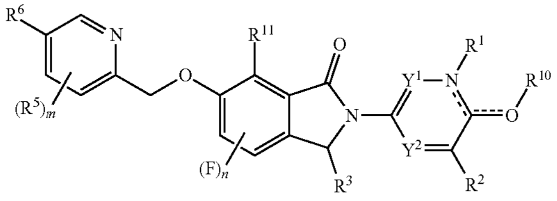

or an isotopically enriched analog, pharmaceutically acceptable salt, prodrug, tautomer, stereoisomer, or a mixture of stereoisomers thereof.

In some embodiments, the compound of Formula I is a compound of Formula X:

X

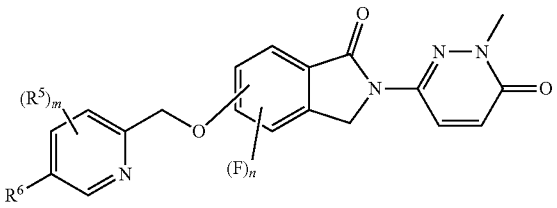

or an isotopically enriched analog, pharmaceutically acceptable salt, prodrug, tautomer, stereoisomer, or a mixture of stereoisomers thereof.

In some embodiments, the compound of Formula I is a compound of Formula XI:

XI

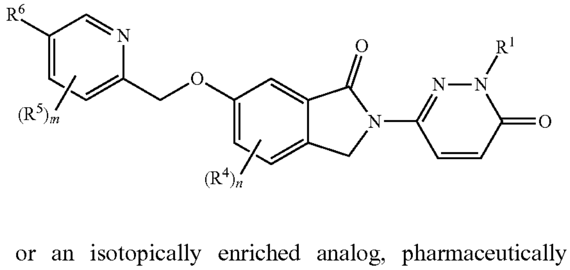

or an isotopically enriched analog, pharmaceutically acceptable salt, prodrug, tautomer, stereoisomer, or a mixture of stereoisomers thereof.

In some embodiments, the compound of Formula I is a compound of Formula XII:

XII

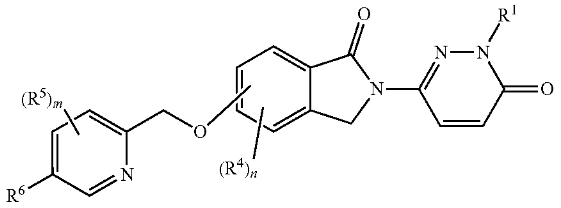

or an isotopically enriched analog, pharmaceutically acceptable salt, prodrug, tautomer, stereoisomer, or a mixture of stereoisomers thereof.

In some embodiments, the compound of Formula I is a compound of Formula XIII:

XIII

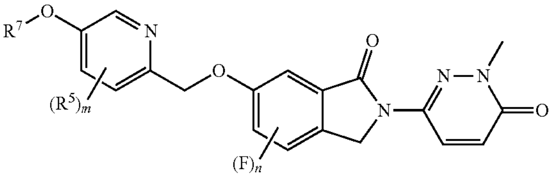

or an isotopically enriched analog, pharmaceutically acceptable salt, prodrug, tautomer, stereoisomer, or a mixture of stereoisomers thereof.

In some embodiments, the compound of Formula I is a compound of Formula XIV:

XIV

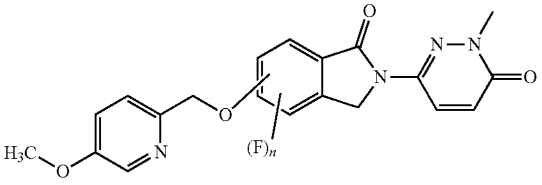

or an isotopically enriched analog, pharmaceutically acceptable salt, prodrug, tautomer, stereoisomer, or a mixture of stereoisomers thereof.

In some embodiments, the compound of Formula I is a compound of Formula XV:

XV

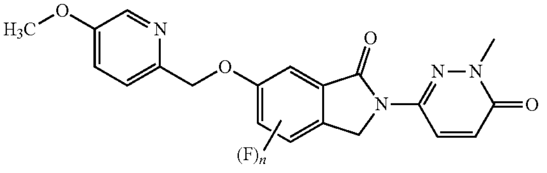

or an isotopically enriched analog, pharmaceutically acceptable salt, prodrug, tautomer, stereoisomer, or a mixture of stereoisomers thereof.

In some embodiments, the compound of Formula I is a compound of Formula XVI:

XVI

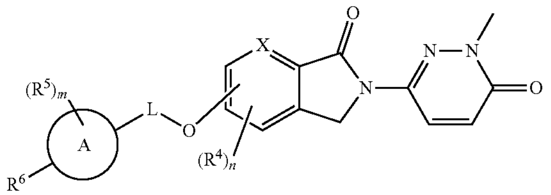

or an isotopically enriched analog, pharmaceutically acceptable salt, prodrug, tautomer, stereoisomer, or a mixture of stereoisomers thereof.

In some embodiments, the compound of Formula I is a compound of Formula XVII:

XVII

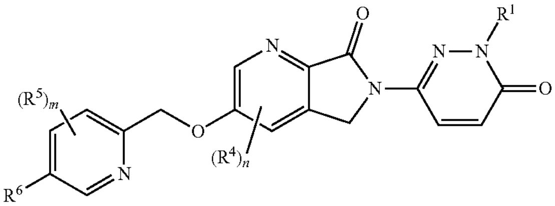

or an isotopically enriched analog, pharmaceutically acceptable salt, prodrug, tautomer, stereoisomer, or a mixture of stereoisomers thereof.

In some embodiments, $R^1$ is hydrogen or $C_{1-6}$alkyl. In some embodiments, $R^1$ is $C_{1-6}$alkyl. In some embodiments, $R^1$ is $C_{1-6}$haloalkyl. In some embodiments, $R^1$ is methyl.

In some embodiments, $R^2$ is hydrogen. In some embodiments, $R^3$ is hydrogen.

In some embodiments, $R^4$ is halo. In some embodiments, $R^4$ is fluoro.

In some embodiments, n is 1. In some embodiments, n is 0.

In some embodiments, $R^{11}$ is hydrogen.

In some embodiments, m is 1.

In some embodiments, $R^5$ is halo. In some embodiments, $R^5$ is fluoro. In some embodiments, n is 1 and $R^5$ is fluoro.

In some embodiments, m is 0.

In some embodiments, $R^6$ is F or $L^1$-$R^7$. In some embodiments, $R^6$ is $L^1$-$R^7$ and $L^1$ is —O—.

In some embodiments, $R^7$ is $C_{1-6}$haloalkyl or $C_{1-6}$alkyl. In some embodiments, $R^7$ is $C_{1-6}$haloalkyl which is substituted with 1 to 6 deuterium atoms.

In some embodiments, $R^6$ is methoxy.

In some embodiments, X is N. In some embodiments, X is $CR^{11}$. In some embodiments, X is C—H.

In some embodiments, L is $CH_2$.

In some embodiments, $Y^1$ is N and $Y^2$ is CH.

In some embodiments, Ring A is heteroaryl containing one or two ring nitrogen atoms. In some embodiments, Ring A is heteroaryl containing one ring nitrogen atom. In some embodiments, Ring A is pyridinyl. In some embodiments, Ring A is pyridin-2-yl.

In some embodiments,

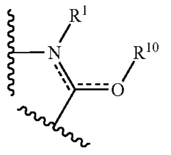

is

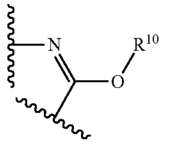

and $R^{10}$ is $C_{1-6}$alkyl.

In some embodiments, the compound comprises at least one halo. In some embodiments, the compound comprises at least one fluoro. In some embodiments, the compound comprises one fluoro. In some embodiments, the compound is substituted by at least one fluoro. In some embodiments, at least one of $R^1$, $R^4$, $R^5$, $R^6$, and $R^{11}$ includes a fluorine atom. In some embodiments, at least one of $R^4$, $R^5$, $R^6$, and $R^{11}$ includes a fluorine atom. In some embodiments, one of $R^4$, $R^5$, or $R^{11}$ is fluoro. In some embodiments, one $R^4$ or one $R^{11}$ is fluoro. In some embodiments, one of $R^4$ or $R^{11}$ is fluoro.

In some embodiments, the compound of Formula I is labeled with one or more radioactive isotopes.

In some embodiments, the compound of Formula I contains one or more positron-emitting radioactive isotopes selected from $^{11}C$, $^{13}N$, $^{15}O$, and $^{18}F$.

In some embodiments, the compound of Formula I or any compound as described herein is labeled with $^3H$, $^{11}C$, $^{13}N$, $^{15}O$, or $^{18}F$. In some embodiments, the compound of Formula I or any compound as described herein is labeled with $^3H$, $^{11}C$, or $^{18}F$.

In some embodiments, an imaging agent comprising the compound of Formula I, or an isotopically enriched analog, pharmaceutically acceptable salt, prodrug, tautomer, stereoisomer, or a mixture of stereoisomers thereof, is provided.

Also provided are additional compounds as described herein. In some embodiments, provided is a compound selected from Table 1, or an isotopically labeled analog, pharmaceutically acceptable salt, solvate, prodrug, stereoisomer, or mixture of stereoisomers thereof.

In some embodiments, provided is a compound selected from those in Table 1, or an isotopically enriched analog, pharmaceutically acceptable salt, prodrug, tautomer, stereoisomer, or a mixture of stereoisomers thereof, optionally wherein the compound is labeled with one or more radioactive isotopes.

In some embodiments, provided is a pharmaceutical composition comprising the compound described herein, or an isotopically enriched analog, pharmaceutically acceptable salt, prodrug, tautomer, stereoisomer, or a mixture of stereoisomers thereof, and a pharmaceutically acceptable excipient.

Non-metal radionuclides may be covalently linked to the compounds described herein by a reaction well known from the state of art. When the radionuclide is a metallic positron-emitter, it is understood that labeling may require the use of a chelating agent. Such chelating agents are well known from the state of the art.

In some embodiments, provided is a compound selected from those in described in the Examples section provided herein.

Also provided is a compound, or an isotopically enriched analog, pharmaceutically acceptable salt, prodrug, tautomer, stereoisomer, or a mixture of stereoisomers thereof, selected from Table 1:

TABLE 1

| Ex. | Structure |
|---|---|
| 1-1 | 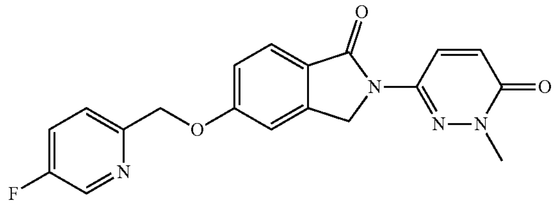 [SMILES: Cn1nc(N2Cc3cc(OCc4ccc(F)cn4)ccc3C2=O)ccc1=O] |
| 1-2 | 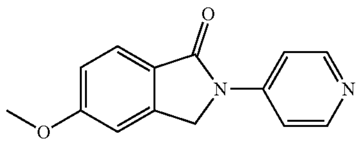 [SMILES: COc1ccc2c(c1)CN(c1ccncc1)C2=O] |
| 1-3 | 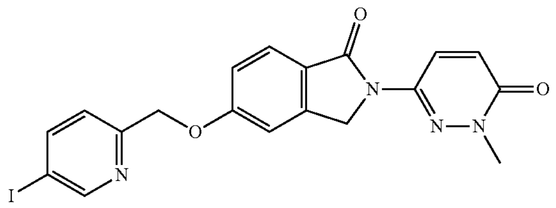 [SMILES: Cn1nc(N2Cc3cc(OCc4ccc(I)cn4)ccc3C2=O)ccc1=O] |

TABLE 1-continued
| Ex. | Structure |
|---|---|
| 1-4 | 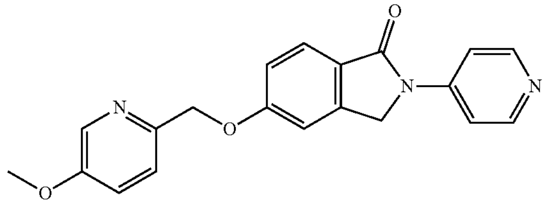 [SMILES: COc1ccc(COc2ccc3c(c2)CN(c2ccncc2)C3=O)nc1] |
| 1-5 | 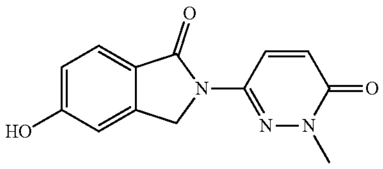 [SMILES: Cn1nc(N2Cc3cc(O)ccc3C2=O)ccc1=O] |
| 1-6 | 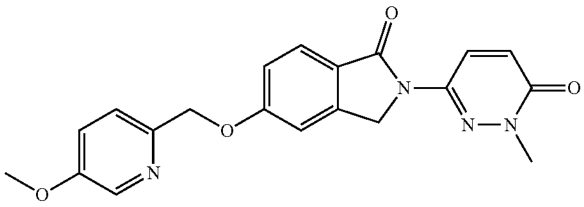 [SMILES: COc1ccc(COc2ccc3c(c2)CN(c2ccc(=O)n(C)n2)C3=O)nc1] |
| 1-7 | 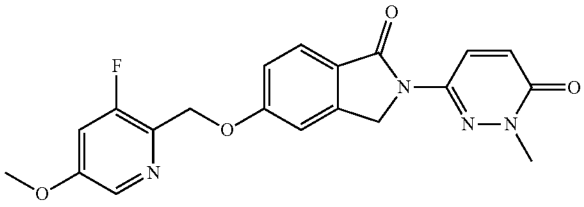 [SMILES: COc1cnc(COc2ccc3c(c2)CN(c2ccc(=O)n(C)n2)C3=O)c(F)c1] |
| 1-8 | 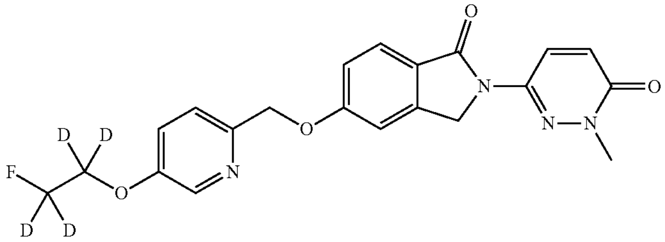 [SMILES: [2H]C([2H])(F)C([2H])([2H])Oc1ccc(COc2ccc3c(c2)CN(c2ccc(=O)n(C)n2)C3=O)nc1] |
| 1-9 | 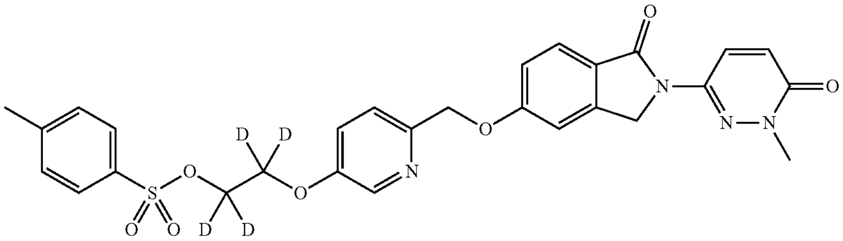 [SMILES: [2H]C([2H])(Oc1ccc(COc2ccc3c(c2)CN(c2ccc(=O)n(C)n2)C3=O)nc1)C([2H])([2H])OS(=O)(=O)c1ccc(C)cc1] |
| 1-10 | 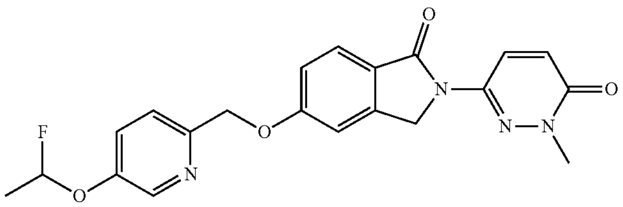 [SMILES: CC(F)Oc1ccc(COc2ccc3c(c2)CN(c2ccc(=O)n(C)n2)C3=O)nc1] |

TABLE 1-continued
| Ex. | Structure |
| --- | --- |
| 1-11 | 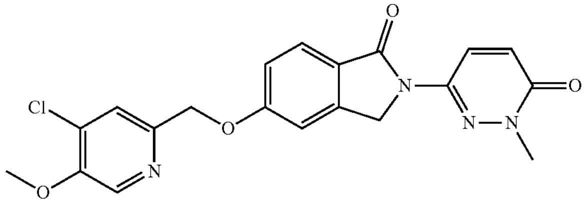 [SMILES: COc1cnc(COc2ccc3c(c2)CN(c2ccc(=O)n(C)n2)C3=O)cc1Cl] |
| 1-12 | 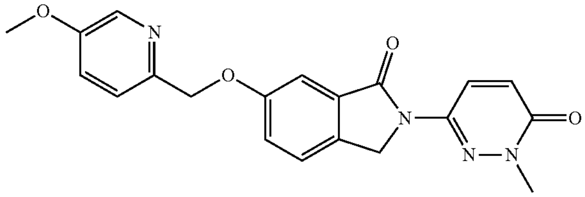 [SMILES: COc1ccc(COc2ccc3c(c2)C(=O)N(c2ccc(=O)n(C)n2)C3)nc1] |
| 1-13 | 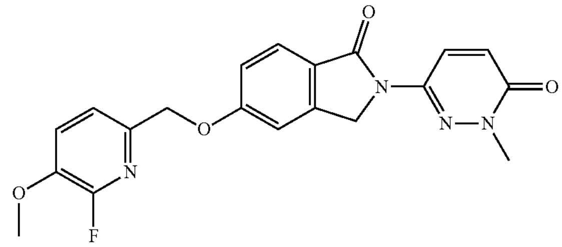 [SMILES: COc1ccc(COc2ccc3c(c2)CN(c2ccc(=O)n(C)n2)C3=O)nc1F] |
| 1-14 | 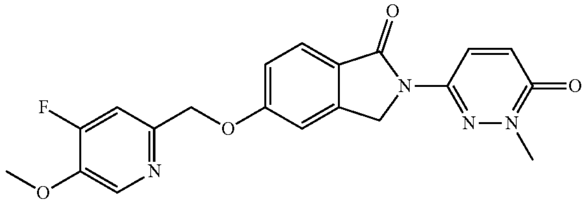 |
| 2-1 | 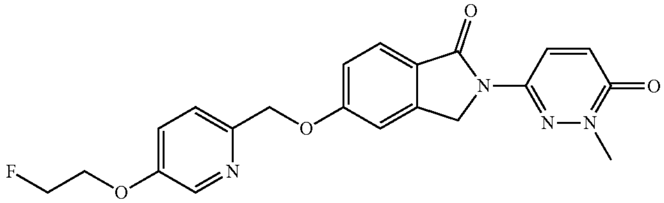 |
| 2-2 | 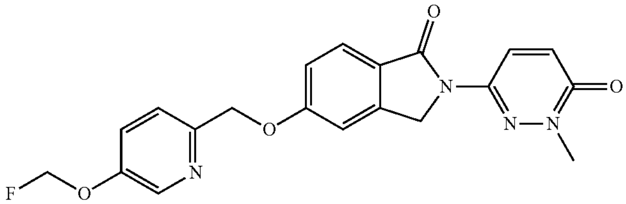 |
| 2-3 | 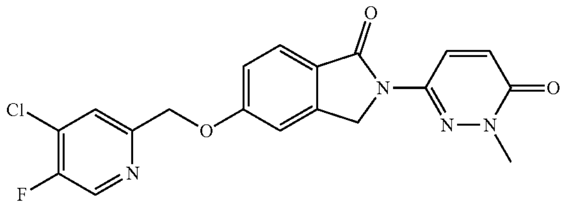 [SMILES: Cn1nc(N2Cc3cc(OCc4cc(Cl)c(F)cn4)ccc3C2=O)ccc1=O] |

TABLE 1-continued
| Ex. | Structure |
| --- | --- |
| 3-1 | 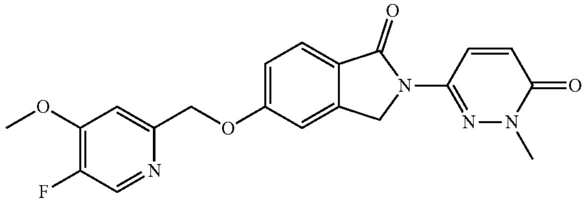 [SMILES: COc1cc(COc2ccc3c(c2)CN(c2ccc(=O)n(C)n2)C3=O)ncc1F] |
| 4-1 | 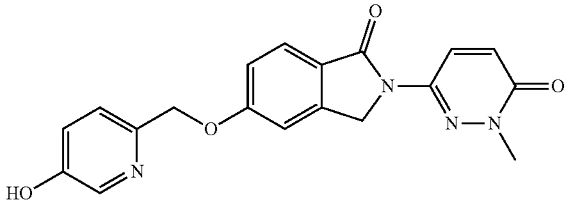 [SMILES: Cn1nc(N2Cc3cc(OCc4ccc(O)cn4)ccc3C2=O)ccc1=O] |
| 5-1 | 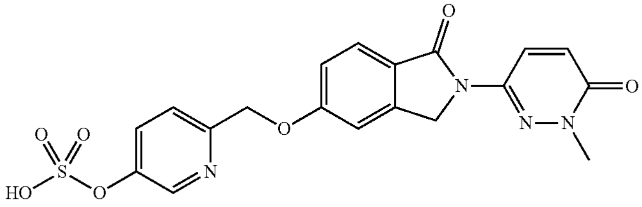 [SMILES: Cn1nc(N2Cc3cc(OCc4ccc(OS(=O)(=O)O)cn4)ccc3C2=O)ccc1=O] |
| 6-1 | 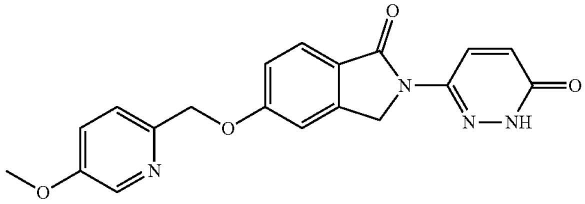 [SMILES: COc1ccc(COc2ccc3c(c2)CN(c2ccc(=O)[nH]n2)C3=O)nc1] |
| 7-1 | 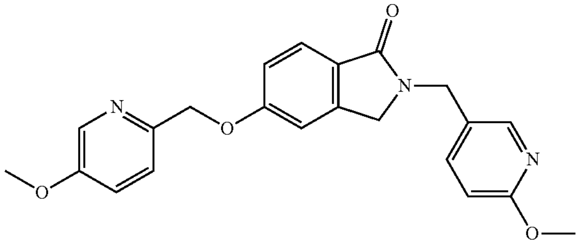 |
| 8-1 | 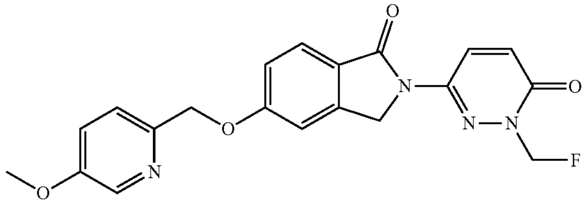 [SMILES: COc1ccc(COc2ccc3c(c2)CN(c2ccc(=O)n(CF)n2)C3=O)nc1] |
| 8-2 | 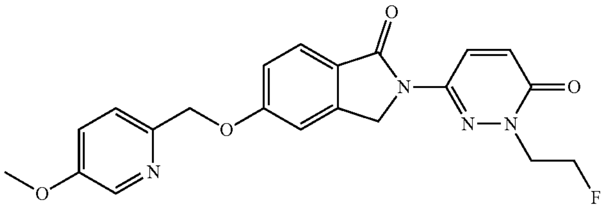 [SMILES: COc1ccc(COc2ccc3c(c2)CN(c2ccc(=O)n(CCF)n2)C3=O)nc1] |

TABLE 1-continued
| Ex. | Structure |
|---|---|
| 9-1 | 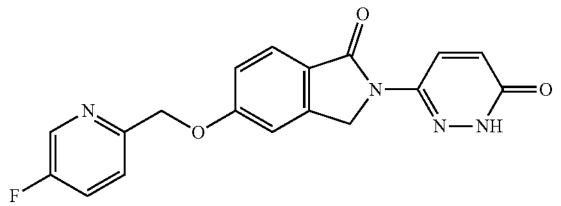 [SMILES: O=C1c2ccc(OCc3ccc(F)cn3)cc2CN1c1ccc(=O)[nH]n1] |
| 9-2 | 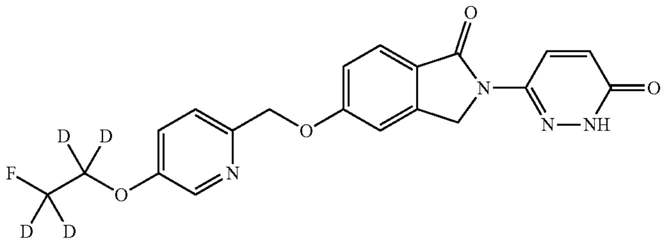 [SMILES: [2H]C([2H])(F)C([2H])([2H])Oc1ccc(COc2ccc3c(c2)CN(c2ccc(=O)[nH]n2)C3=O)nc1] |
| 9-3 | 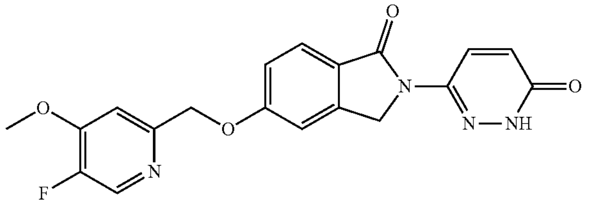 [SMILES: COc1cc(COc2ccc3c(c2)CN(c2ccc(=O)[nH]n2)C3=O)ncc1F] |
| 10-1 | 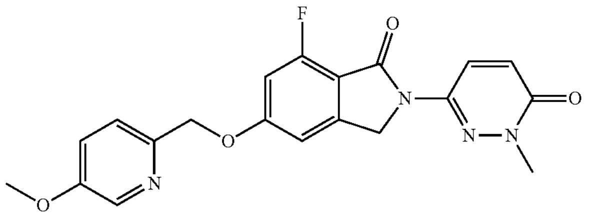 [SMILES: COc1ccc(COc2cc(F)c3c(c2)CN(c2ccc(=O)n(C)n2)C3=O)nc1] |
| 10-2 | 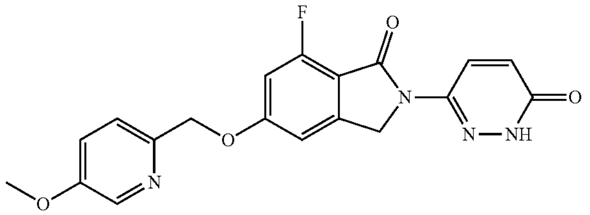 [SMILES: COc1ccc(COc2cc(F)c3c(c2)CN(c2ccc(=O)[nH]n2)C3=O)nc1] |
| 11-1 | 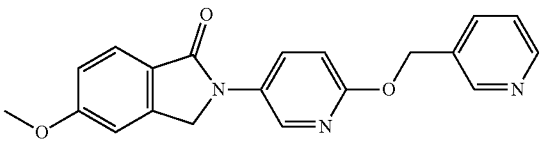 [SMILES: COc1ccc2c(c1)CN(c1ccc(OCc3cccnc3)nc1)C2=O] |
| 12-1 | 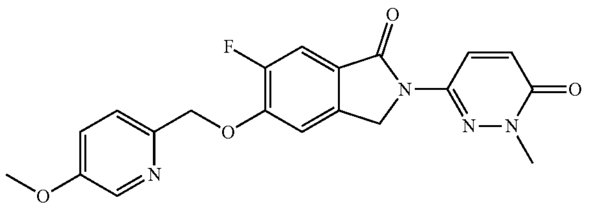 [SMILES: COc1ccc(COc2cc3c(cc2F)C(=O)N(c2ccc(=O)n(C)n2)C3)nc1] |

TABLE 1-continued
| Ex. | Structure |
| --- | --- |
| 12-2 | 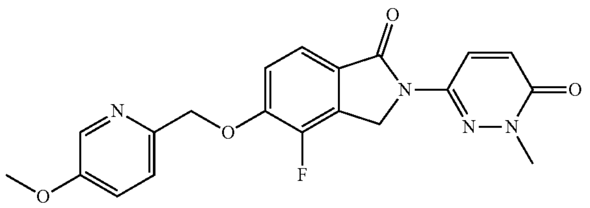 [SMILES: COc1ccc(COc2ccc3c(c2F)CN(c2ccc(=O)n(C)n2)C3=O)nc1] |
| 12-3 | 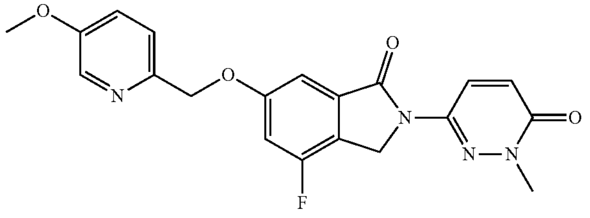 [SMILES: COc1ccc(COc2cc(F)c3c(c2)C(=O)N(c2ccc(=O)n(C)n2)C3)nc1] |
| 12-4 | 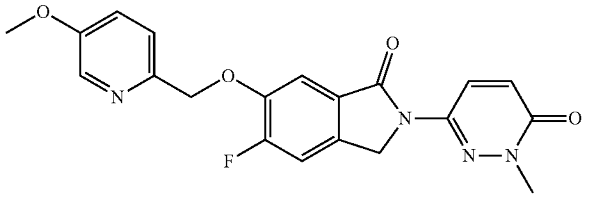 [SMILES: COc1ccc(COc2cc3c(cc2F)CN(c2ccc(=O)n(C)n2)C3=O)nc1] |
| 12-5 | 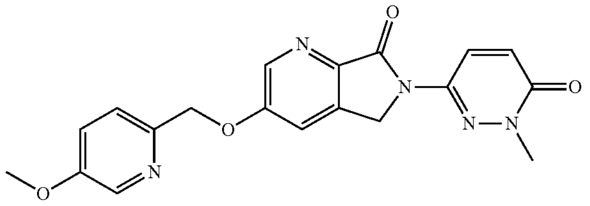 [SMILES: COc1ccc(COc2cnc3c(c2)CN(c2ccc(=O)n(C)n2)C3=O)nc1] |
| 12-6 | 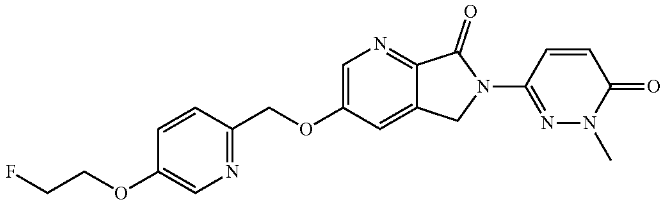 [SMILES: Cn1nc(N2Cc3cc(OCc4ccc(OCCF)cn4)cnc3C2=O)ccc1=O] |
| 12-7 | 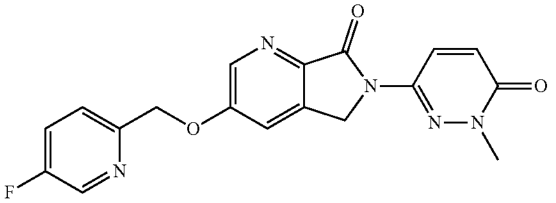 |
| 12-8 | 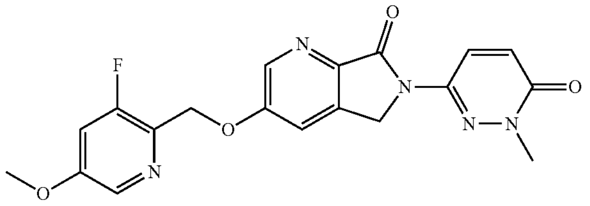 [SMILES: COc1cnc(COc2cnc3c(c2)CN(c2ccc(=O)n(C)n2)C3=O)c(F)c1] |

TABLE 1-continued
| Ex. | Structure |
| --- | --- |
| 12-9 | 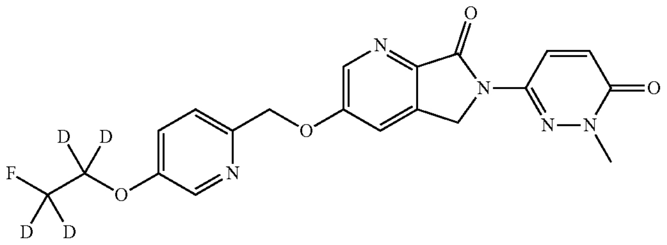 [SMILES: [2H]C([2H])(F)C([2H])([2H])Oc1ccc(COc2cnc3c(c2)CN(c2ccc(=O)n(C)n2)C3=O)nc1] |
| 12-10 | 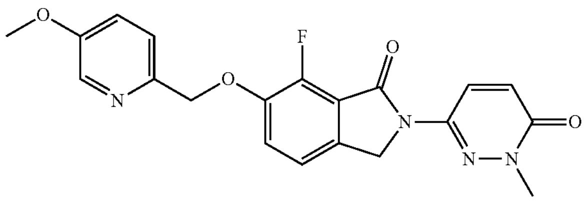 [SMILES: COc1ccc(COc2ccc3c(c2F)C(=O)N(c2ccc(=O)n(C)n2)C3)nc1] |
| 13-1 | 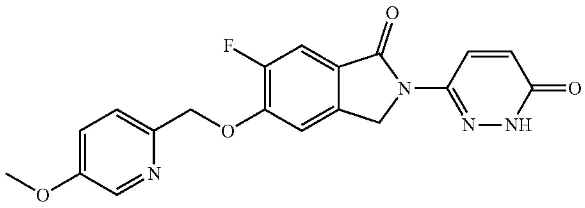 |
| 13-2 | 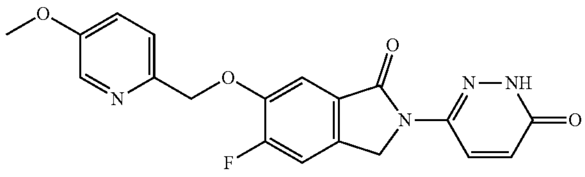 [SMILES: COc1ccc(COc2cc3c(cc2F)CN(c2ccc(=O)[nH]n2)C3=O)nc1] |
| 13-3 | 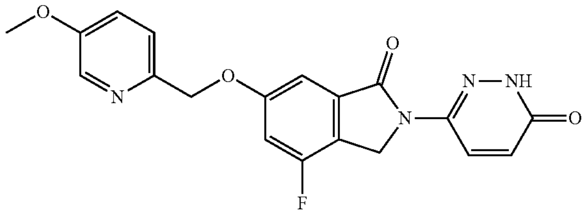 [SMILES: COc1ccc(COc2cc(F)c3c(c2)C(=O)N(c2ccc(=O)[nH]n2)C3)nc1] |
| 14-1 | 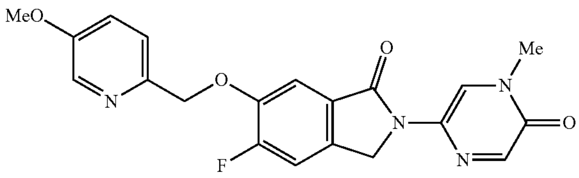 [SMILES: COc1ccc(COc2cc3c(cc2F)CN(c2cn(C)c(=O)cn2)C3=O)nc1] |
| 14-2 | 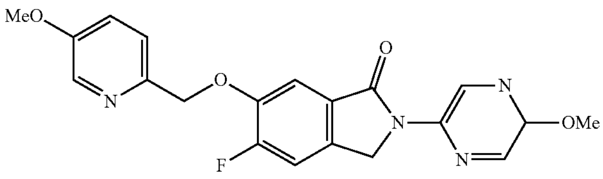 [SMILES: COc1ccc(COc2cc3c(cc2F)CN(C2=CNC(OC)C=N2)C3=O)nc1] |

TABLE 1-continued

| Ex. | Structure |
|---|---|
| 14-3 | 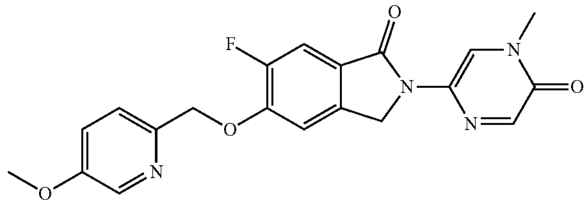 [SMILES: COc1ccc(COc2cc3c(cc2F)C(=O)N(c2cn(C)c(=O)cn2)C3)nc1] |

Diagnostic Methods and Uses

In some embodiments, a method of detecting the presence or absence of a protein susceptible to aggregation in an individual is provided, comprising administering an effective amount of a compound or an imaging agent described herein to an individual, and generating an image of a body part or body area of the individual. Generating an image of a body part or body area of the individual may comprise generating an image to detect the presence or absence of a protein susceptible to aggregation in the image. Thus, the compounds disclosed herein are useful for detecting a disease or condition mediated, at least in part, by a protein susceptible to protein aggregation. In some embodiments, the presence or absence of a protein aggregate corresponds to the presence or absence of a neurodegenerative disease. In some embodiments, the neurodegenerative disease is selected from Alzheimer's disease, amyotrophic lateral sclerosis, Huntington's disease, Parkinson's disease, Prion disease, and spinocerebellar ataxias.

Provided are methods of generating diagnostic images, and of detecting the presence or absence of a protein susceptible to aggregation, using positron emission tomography (PET). PET imaging may be conducted as known to those of skill in the art, or as follows. PET imaging may involve the administration of a positron-emitting radionuclide tracer, for example, a compound or imaging agent described herein, to an individual. The tracer is then given sufficient time to associate with the protein of interest, at which time the individual is placed in a scanning device comprising a ring of scintillation detectors. An emitted positron travels through the individual's tissue for a short (isotope-dependent) distance, until it interacts with an electron. The interaction annihilates both the electron and the positron, producing a pair of photons. The photons are detected by a scintillator in the scanning device. Photons that do not arrive in pairs are ignored.

Also provided are methods of generating diagnostic images, and of detecting the presence or absence of a protein susceptible to aggregation, comprising PET with concurrent computed tomography imaging (PET/CT), with concurrent magnetic resonance imaging (PET/MRI), or single-photon emission computed tomography (SPECT) imaging. In general, computed tomography uses X-rays or gamma rays to detect the structure of the brain, while magnetic resonance imaging uses magnetic fields and radio waves.

Thus, a compound or an imaging agent described herein may be administered by methods known in the art including those described herein. The compound or imaging agent may enter circulation and bind to the protein susceptible to aggregation, or to aggregates thereof. When the compound or imaging agent is labeled with a radioactive isotope, the emitted particles may be detected.

In some embodiments, the compound or imaging agent is administered into the individual's vascular system. The compound or imaging agent may pass through the blood-brain barrier. Thus, generating an image may comprise generating an image of at least part of the individual's brain, for example, the part to which the compound has distributed.

Also provided are methods of generating diagnostic images, and of detecting the presence or absence of a protein susceptible to aggregation, in a biological sample comprising contacting the biological sample with an effective amount of a compound or an imaging agent described herein and generating an image associated with the biological sample. In some embodiments, the contacting and the generating may be conducted in vitro. In some embodiments the contacting is in vivo and the generating is in vitro.

Also provided are methods for detecting the presence or absence of a pathologic process associated with a protein susceptible to protein aggregation, for example huntingtin protein (HTT protein), in an individual comprising: administering an effective amount of a compound or an imaging agent described herein; generating an image to detect the presence or absence of huntingtin protein (HTT protein) in the image; and detecting the presence or absence of a pathologic process, e.g., a neurodegenerative disease. In some embodiments, the HTT protein is present as monomers, oligomers, or aggregates, or a combination thereof. In some embodiments, the protein susceptible to aggregation is huntingtin protein (HTT protein). The HTT protein may be mutant. In some embodiments, the HTT protein is found in the brain, for example, in basal ganglia.

In some embodiments, the body part or body area is selected from head, spinal cord, limb, thorax, and/or abdomen. In some embodiments, the body part or body area is brain. In some embodiments, the HTT protein is found in basal ganglia. In some embodiments, the protein susceptible to aggregation, e.g., HTT protein, is present in the brain, liver, heart, and/or muscle of the individual. In some embodiments, generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof. In some embodiments, generating an image comprises PET imaging. In some embodiments, the protein susceptible to aggregation, e.g., HTT protein, is present in the basal ganglia, cortex, hippocampus, and/or brain stem of the brain of the individual. In some embodiments, the protein susceptible to aggregation, e.g., HTT protein, is present as monomers, oligomers, or aggregates, or a combination thereof.

In some embodiments, the individual has, or is discovered to have, Huntington's disease.

Also provided are methods for detecting the presence or absence of a pathologic process associated with β-amyloid protein in an individual comprising: administering an effective amount of a compound or an imaging agent described herein; generating an image of a body part or body area of the individual; and detecting the presence or absence of the pathologic process. In some embodiments, the individual has, or is discovered to have, Alzheimer's Disease (AD).

Also provided are diagnostic methods of using a compound or an imaging agent described herein to monitor disease progression in a patient by quantifying the change in levels of the protein susceptible to aggregation in the patient.

In some embodiments, provided is a compound having suitable protein aggregate, e.g., HTT protein aggregate or β-amyloid protein aggregate, binding kinetics to function as imaging agents. Thus, a compound described herein may be characterized by one or more of: 1) a high affinity for such protein aggregates; 2) a low affinity for nearby structures; and/or 3) slow dissociation kinetics from such protein aggregates. Dissociation kinetics may be expressed as the dissociation rate constant $k_{diss}$ as defined in the equation below (wherein A and B refer to the protein aggregate and the imaging agent, and $k_{assn}$ is the association rate constant):

$$d[AB]/dt=k_{assn}[A][B]-k_{diss}[AB]$$

In some embodiments, the effective amount of the compound or imaging agent described herein comprises from about 0.1 to about 20 mCi. In some embodiments, the effective amount of the compound or imaging agent described herein comprises about 0.1, about 0.3, about 0.5, about 0.7, about 1, about 3, about 5, about 7, about 10, about 15, or about 20 mCi, or a range of values therebetween. In some embodiments, the effective amount of the compound or imaging agent described herein comprises about 10 mCi.

Suitable radionuclides that may be incorporated in a compound described herein include, but are not limited to, $^{3}H$ (also written as T), $^{11}C$, $^{18}F$, $^{35}S$, $^{123}I$, $^{75}Br$, $^{76}Br$, $^{77}Br$, $^{82}Br$, $^{131}I$, $^{15}O$, $^{13}N$, and $^{211}At$. The radionuclide that is incorporated in the compound will depend on the specific imaging application. In some embodiments including PET imaging, compounds that incorporate a radionuclide selected from $^{11}C$, $^{18}F$, $^{123}I$, $^{131}I$, $^{75}Br$, $^{76}Br$ or $^{77}Br$ may be used. In certain applications incorporation of a chelating radionuclide such as $^{99m}Tc$ may also be useful. In some embodiments, $^{18}F$ may be preferable over $^{11}C$ because with the longer half-life of $^{18}F$, imaging can be carried out long enough to allow a stronger signal to develop. In some embodiments, a compound or imaging agent described herein can be labeled with a positron emitting radionuclide or a gamma emitting radionuclide. Some examples of positron-emitting radionuclides include $^{15}O$, $^{13}N$, $^{11}C$, $^{18}F$, $^{76}Br$, and $^{124}I$, which have half-lives of about 2, 10, 20, 110 minutes, 16 hours, and 4.2 days respectively.

In some embodiments, a compound or an imaging agent described herein may be labelled with $^{3}H$, $^{11}C$, or $^{18}F$. In some embodiments, a compound or an imaging agent described herein may be labelled with a positron emitter selected from $^{11}C$ and $^{18}F$. Methods for the introduction of $^{11}C$ may include, but are not limited to, alkylation with [$^{11}C$]iodomethane or [$^{11}C$]methyl triflate. Carbon-11 has a half-life of approximately 20 minutes, thus $^{11}C$ generally needs to be generated in an on-site cyclotron, and may be produced as [$^{11}C$]carbon dioxide. The [$^{11}C$]carbon dioxide is converted to the chemical species appropriate for the radiosynthesis (generally [$^{11}C$]iodomethane or the like), and the synthesis of the radiopharmaceutical is completed and used on-site in a PET imaging study after the appropriate radiochemical purity and specific activity have been determined. Typical methods of introducing $^{18}F$ include but are not limited to nucleophilic and electrophilic methods. Nucleophilic methods include displacement of a halide, tosylate, or other leaving group with labeled cesium fluoride, potassium fluoride, tetrabutylammonium fluoride, tetramethylammonium fluoride, or potassium fluoride kryptofix-222. Electrophilic reagents that may be suitable for introducing [$^{18}F$] isotopes include labeled diethylaminosulfur trifluoride (DAST), bis(2-methoxyethyl)aminosulfur trifluoride (Deoxofluor), N-fluorobenzenesulfonimide (NFSI), N-fluoropyridinium salts, 1-chloromethyl-4-fluoro-1,4-diazoniabicyclo[2.2.2]octane bis(tetrafluoroborate) (Selectfluor), N-fluoropyridinium triflate, xenon fluoride, 2-pyridinesulfonyl fluoride (PyFluor), 3-pyridinesulfonyl fluoride, 4-pyridinesulfonyl fluoride, 4-chloro-2-pyridinesulfonyl fluoride, ethenesulfonyl fluoride, fluoro-benziodoxole, p-fluorophenylaminosulfur trifluoride, p-nitrophenylaminosulfur trifluoride, or pentafluorophenylaminosulfur trifluoride. General methods for the introduction of positron emitters are described in the literature (e.g., see Miller et al., *Angewandte Chemie International Edition,* 47 (2008), 8998-9033; Jacobson, O. et al., Bioconjugate Chem., 26 (2015), 1-18; Deng, X. et al., *Angewandte Chemie International Edition,* 58(9), (2019), 2580-2605). Methods of introducing tritium can be accomplished according to methods known in the art, such as synthetic methods, recoil, or exchange reactions.

Fluorine-18 has a half-life of approximately 110 minutes, thus synthesis of [$^{18}F$] radiopharmaceuticals need not necessarily have to occur at the site of the cyclotron nor proximal to the PET imaging study center. Fluorine-18 is also thought to exhibit favorable nuclear and physical characteristics, including high positron decay ratio (97%), relatively short half-life (109.7 min), and low positron energy (up to 0.635 MeV). The positron energy may correspond to a short diffusion range (<2.4 mm) in vivo that may provide superior resolution limits of a PET image.

As will be recognized, the steps of the methods described herein need not be performed any particular number of times or in any particular sequence. Additional objects, advantages and novel features of the disclosure will become apparent to those skilled in the art upon examination of the examples provided below, which are intended to be illustrative and are not limiting.

Indications and Treatment Methods

A compound or an imaging agent described herein may be useful for treating a disease or condition mediated, at least in part, by a protein susceptible to aggregation. In some embodiments, a compound or an imaging agent described herein is useful for treating a disease or condition mediated, at least in part, by HTT protein. In some embodiments, treatment of a disease or condition mediated, at least in part, by a protein susceptible to aggregation may comprise administration of a compound or an imaging agent described herein. Treatment may include coadministration of a compound or an imaging agent described herein and one or more other active agents and/or therapies. Thus, in some embodiments, provided is a method of treating or preventing a disease or condition mediated, at least in part, by a protein susceptible to aggregation in a patient in need thereof, comprising administering to the patient a therapeutically effective amount of a compound or an imaging agent described herein.

Exemplary diseases and conditions are as follows.

Huntington's Disease (HD)

Huntington's disease (HD) is an inherited progressive neurodegenerative disorder, characterized by motor, cognitive, and psychiatric deficits as well as neurodegeneration and brain atrophy. Atrophy may begin in the striatum and cortex and extend to other subcortical brain regions. HD belongs to a family of neurodegenerative diseases in which an expanded CAG repeat tract results in long stretches of polyglutamine (polyQ) in an encoded protein. The family also includes dentatorubral-pallidoluysian atrophy (DRPLA), spinal and bulbar muscular atrophy (SBMA) and the spinocerebellar ataxias (SCAs). In HD, the selective neurodegeneration of the γ-aminobutyric acid-releasing spiny-projection neurons of the striatum had been observed, although neuron loss in many other brain regions has also been reported. Symptoms of HD include loss of motor control, psychiatric symptoms, memory and/or cognitive impairment.

HD protein huntingtin (HTT protein) is a 348-kDa multidomain protein that contains a polymorphic glutamine/proline-rich domain at its amino-terminus. The number of CAG repeats in the $IT_{15}$ gene that encodes the varies from 6 to 35 in healthy individuals; repeats of 36 or more define an HD allele. The length of the CAG expansion has been inversely correlated with age of disease onset, with cases of juvenile onset characterized by expansions of more than 60 repeats. The longer polyQ domain is believed to induce conformational changes in the HTT protein, which causes it to form intracellular aggregates that, in many, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

The part of the brain most affected by HD, and thus believed to be most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

Basal ganglia are a group of subcortical nuclei responsible primarily for motor control, as well as other roles such as motor learning, executive functions and behaviors, and emotions. Disruption of the basal ganglia network are believed to contribute to several movement disorders. Normal function of the basal ganglia requires fine tuning of neuronal excitability within each nucleus to determine the degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

The administration of a compound described herein may result in a decrease, for example, at least a 10% decrease (e.g., at least 15%, 20%, 25%, 30%, 35%, 40%, 45%, 50%, 55%, 60%, 65%, 70%, 75%, 80%, 85%, 90% or 100%) in one or more symptoms of a disease or condition described herein. The disease or condition may be a disorder of the nervous system that is secondary to a disease, condition, or therapy having a primary effect outside of the nervous system; an injury to the nervous system caused by physical, mechanical or chemical trauma; autoimmune neural degeneration; neurodegeneration secondary to infection; and/or ocular neurodegeneration. Symptoms of nerve degeneration include, e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

A neurodegenerative disease is a disease or condition in which the function of a subject's nervous system becomes impaired. Examples of neurodegenerative diseases include, e.g., Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion disease, Refsum's disease, Sandhoff disease, Schilder's disease, Subacute combined degeneration of spinal cord secondary to Pernicious Anaemia, Schizophrenia, Spinocerebellar ataxia, Spinal muscular atrophy, Steele-Richardson-Olszewski disease, insulin resistance or Tabes dorsalis.

In some embodiments, the disease or condition is selected from Huntington's disease (HD), dentatorubral-pallidoluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma.

A compound described herein, when administered to a subject, may inhibit neuron degeneration. In some embodiments, inhibiting neuron degeneration may include inhibiting axon or neuron degeneration in a neuron. Such inhibition with respect to the entire neuron or a portion thereof, such as the neuron cell body, axons and dendrites. This can be assessed, for example, by analysis of neurological function according to methods known in the art. The administration of a compound described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or 100%) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the compounds described herein.

Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the disclosure include cerebellar granule neurons, dorsal root ganglion neurons, PNS neurons (e.g. sensory neurons), and cortical neurons. Other examples of cell types that may be subject to treatment according to the disclosure include astrocytes and microglia.

Further, the compounds described herein can be used in the prevention or treatment of memory loss. Types of memory that can be affected by loss, and thus treated according to the disclosure, include episodic memory, semantic memory, short-term memory, and long-term memory.

In some embodiments, the disease or condition is a neurodegenerative disease selected from Alzheimer's disease, amyotrophic lateral sclerosis, Huntington's disease, Parkinson's disease, Prion disease, and spinocerebellar ataxias. In some embodiments, the neurodegenerative disease is classified as a trinucleotide repeat disorder. In some embodiments, the trinucleotide repeat disorder is classified as belonging to Category I, Category II, or Category III.

In some embodiments, the pathologic process is associated with, or caused by, a disease or condition selected from Huntington's disease (HD), dentatorubral-pallidoluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma. In some embodiments, the pathologic process is a neurodegenerative disease selected from Alzheimer's disease, amyotrophic lateral sclerosis, Huntington's disease, Parkinson's disease, Prion disease, and spinocerebellar ataxias. In some embodiments, the neurodegenerative disease is classified as a trinucleotide repeat disorder. In some embodiments, the trinucleotide repeat disorder is classified as belonging to Category I, Category II, or Category III.

In some embodiments, the neurodegenerative disease is Huntington's disease.

Also provided is use of a compound described herein for the manufacture of a medicament for use in diagnosis, prevention, or treatment of a disease or condition described herein. For example, the disease or condition may be Huntington's disease.

Imaging Agents and Pharmaceutical Compositions

An imaging agent will generally comprise a compound described herein labeled with a positron emitting radionuclide. Imaging agents labeled with positron emitting radionuclides are generally administered via intravenous injection shortly after (for example, within one hour of synthesis) due to the short half-life of the radionuclides. The amount of imaging agent required will normally be determined by the prescribing physician. The dose may vary according to various factors, including but not limited to the associative kinetics of the compound, the quantity of emission from the radionuclide used, the half-life of the radionuclide, the body part, body area, and/or tissue to be imaged, and the characteristics of the individual. Those of ordinary skill in the art will appreciate that an effective amount will generally be the amount of labeled compound sufficient to produce emissions in the range of from about 0.1 to about 20 mCi, or about 1 to about 5 mCi. The mass of labeled compound in an effective amount of imaging agent may be about 0.1 to about 500 mg.

Generally, a compound or an imaging agent described herein may be administered to a patient in need thereof via any suitable route. Routes of administration may include, for example, parenteral administration, including subcutaneous, intramuscular, intravenous, by means of, for example a drip patch. Further suitable routes of administration include, but are not limited to, oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

With regard to PET imaging, administration of a compound or an imaging agent described herein to the individual may be intravenous. The pharmaceutical composition may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables. Such solutions may be formulated as 0.01%-10% isotonic solutions, pH 5-7, with appropriate salts.

The compound or imaging agent described herein may be administered parenterally in a sterile medium. Parenteral administration includes subcutaneous injections, intravenous, intramuscular, intrathecal injection or infusion techniques. The compound or imaging agent described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

A pharmaceutical composition, for example, for injection, may comprise a cyclodextrin. The cyclodextrin may be, for example, a hydroxypropyl cyclodextrin or a sulfobutylether cyclodextrin. The cyclodextrin may be, for example, an α-cyclodextrin, a β-cyclodextrin, or a γ-cyclodextrin.

A compound or an imaging agent described herein may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

In some embodiments, the compound or imaging agent described herein is administered as a pharmaceutical composition. Accordingly, provided are pharmaceutical compositions comprising at least one compound or imaging agent described herein, together with at least one pharmaceutically acceptable vehicle chosen from carriers, adjuvants, and excipients. A compound or imaging agent of the present disclosure can be formulated into a pharmaceutical composition using techniques known to those of skill in the art.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound or imaging agent may be sufficient to provide a practical quantity of material for administration per dose of the compound or imaging agent.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENs®; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound or imaging agent described herein.

Effective concentrations of at least one compound or imaging agent described herein are mixed with a suitable pharmaceutically acceptable vehicle. In instances in which the compound or imaging agent exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous buffer, for example, sodium bicarbonate.

Upon mixing or addition of a compound or imaging agent described herein, the resulting mixture may be a solution, suspension, emulsion or the like. The form of the resulting mixture depends upon a number of factors, including the intended mode of administration and the solubility of the compound or imaging agent in the chosen vehicle. The effective concentration sufficient for imaging or treatment may be empirically determined according to known methods in the art.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of the compound or imaging agent described herein. In some embodiments, oral pharmaceutical compositions contain at least 5% (weight %) of the compound or imaging agent. Some embodiments contain from 25% to 50% or from 5% to 75% of the compound or imaging agent.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound or imaging agent described herein can be incorporated into oral liquid preparations such as aqueous or oily suspensions, solutions, emulsions, syrups, or elixirs, for example. Furthermore, pharmaceutical compositions containing the compound or imaging agent described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel® RC-591, tragacanth and sodium alginate; typical wetting agents include lecithin and polysorbate 80; and typical preservatives include methyl paraben and sodium benzoate.

Aqueous suspensions containing the compound or imaging agent in admixture with excipients suitable for the manufacture of aqueous suspensions are provided. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the compound or imaging agent in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of an oil-in-water emulsion. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

The pharmaceutical composition may also be coated by conventional methods, typically with pH or time-dependent coatings, such that the compound or imaging agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

The compound or imaging agent described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound or imaging agent described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Topical pharmaceutical compositions comprising at least one compound, or an isotopically labeled analog, pharmaceutically acceptable salt, solvate, prodrug, stereoisomer, or mixture of stereoisomers thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulfoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, and ethylene glycol monostearate.

The compound or imaging agent described herein may also be formulated for transdermal administration as a transdermal patch.

The compound or imaging agent described herein may also be administered in a liposome delivery system. Liposomes may be classified as small unilamellar vesicles, large unilamellar vesicles, and multilamellar vesicles. Liposomes can be formed from a variety of amphipathic molecules, in particular phospholipids. Constituents of liposomes may include cholesterol, stearylamine and/or phosphatidylcholines. Liposomes are suitable for various routes of administration including topical and injection into various tissues. Thus, intravitreal (e.g., in treatment of glaucoma), intraperitoneal, intravenous, intravascular, intraarticular, and intramuscular administration of liposomes is contemplated.

Other pharmaceutical compositions useful for attaining systemic delivery of the compound or imaging agent include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound or imaging agent described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of the compound or imaging agent described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

The dose of the compound or imaging agent described herein depends upon a variety of factors including the particular pathologic process to be treated or detected, the physiology of the individual, the severity of the symptoms, the route of administration, the frequency of the dosage interval, the particular compound utilized, the efficacy, toxicology profile, pharmacokinetic profile of the compound, and the presence of any deleterious side-effects, among other considerations. The dose under a given set of circumstances generally will be determined by a practitioner on a case-by-case basis based on the above and other factors.

The compound or imaging agent described herein is typically administered at a dosage level and in a manner determined by a practitioner such as a physician. For example, the compound or imaging agent can be administered, in single or multiple doses, at a dosage level of generally 0.001-100 mg/kg, for example, 0.01-100 mg/kg, such as 0.1-70 mg/kg, for example, 0.5-10 mg/kg. The dose can be, for example, for administration once a day or twice a day. Unit dosage forms can contain generally 0.01-1000 mg of the compound or imaging agent described herein, for example, 0.1-50 mg. For intravenous administration, the compound or imaging agent can be administered, in single or multiple dosages, at a dosage level of, for example, 0.001-50 mg/kg, such as 0.001-10 mg/kg, for example, 0.01-1 mg/kg. Unit dosage forms can contain, for example, 0.1-10 mg of the compound or imaging agent.

Kits and Packaging

Also provided herein are kits that include a compound described herein and suitable packaging. In certain embodiments, a kit further includes instructions for use. In some embodiments, a kit includes a compound or an imaging agent described herein and a label and/or instructions for use of the compounds in the treatment of the indications, including the diseases or conditions, described herein.

Also provided herein are articles of manufacture that include a compound or an imaging agent described herein in a suitable container. The container may be a vial, jar, ampoule, preloaded syringe and intravenous bag.

Also provided are packaged pharmaceutical compositions. Such packaged compositions include a pharmaceutical composition comprising a compound or imaging agent described herein, and instructions for using the composition to treat a subject (typically a human patient). In some embodiments, the instructions are for using the pharmaceutical composition to detect a disease or condition described herein. The packaged pharmaceutical composition can include prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound or imaging agent can be administered alone, as mixtures, or in combination with other active agents.

Also provided is use of a compound or imaging agent described herein for the manufacture of a medicament for use in diagnosis, prevention, or treatment of a disease or condition described herein. For example, the disease or condition may be Huntington's disease.

Also provided is use of a compound described herein for the manufacture of an imaging agent for use in diagnosis, prevention, or treatment of a disease or condition described herein. For example, the disease or condition may be Huntington's disease.

Combination Therapy

The methods described herein include methods for detecting, treating or preventing a disease or condition described herein, comprising administering to a subject, simultaneously or sequentially, a compound or imaging agent described herein and one or more additional active agents. For example, the disease or condition may be Huntington's disease. In methods using simultaneous administration, the agents can be present in a combined composition or can be administered separately. When used in combination with one or more additional active agent or agents, a compound or imaging agent described herein may be administered prior to, concurrently with, or following administration of the additional active agent or agents. The administration can be by the same route or by different routes.

Also provided is a pharmaceutical composition comprising a compound or imaging agent described herein and one or more additional active agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. Similarly, also provided is a packaged pharmaceutical composition containing a pharmaceutical composition comprising a compound or imaging agent described herein, and another composition comprising one or more additional active agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. In some embodiments, the active agent is carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, or risperidone.

Also provided are methods for treating or preventing Alzheimer's disease, including treating memory and/or cognitive impairment associated with Alzheimer's disease, comprising administering to a subject, simultaneously or sequentially, a compound or imaging agent described herein and one or more additional agents. In some embodiments, the active agent is Reminyl®, Cognex®, Aricept®, Exelon®, Akatinol®, Neotropin™, Eldepryl®, Estrogen or Clioquinol.

In some embodiments, compounds described herein can be administered with an active agent for treating Parkinson's disease, for example, with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In some embodiments, compounds described herein can be administered with an active agent for treating Alzheimer's disease, for example, with acetylcholinesterase inhibitors (e.g., donepezil, galantamine, and rivastigmine) and/or NMDA receptor antagonists (e.g., memantine).

Synthesis of the Compounds

A compound described herein may be prepared using the methods disclosed herein and routine modifications thereof, which will be apparent given the disclosure herein and methods well known in the art. Conventional and well-known synthetic methods may be used in addition to the teachings herein. The synthesis of a typical compound described herein may be accomplished as described in the following examples. If available, reagents may be purchased commercially, e.g., from Sigma Aldrich or other chemical suppliers.

A compound described herein can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006), Greene's protective groups in organic synthesis. Hoboken, N.J., Wiley-Interscience, and references cited therein.

Furthermore, a compound described herein may contain one or more asymmetric ("chiral") centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromatography, chiral resolving agents, and the like. When enantiomerically pure or enriched compounds are desired, chiral chromatography and/or enantiomerically pure or enriched starting materials may be employed as conventionally used in the art or as described in the Examples.

The starting materials for the following reactions are generally known compounds or can be prepared by known procedures or obvious modifications thereof. For example, many of the starting materials are available from commercial suppliers such as Sigma Aldrich, Alfa Aesar, and the like. Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent," and "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine, and the like). Generally, the term inert, as used herein with respect to a solvent, refers to a material that does not undergo reaction to form the target compound of interest through carbon-carbon bond forming reactions. Unless specified to the contrary, the solvents used in the reactions of the present disclosure are inert organic solvents, and the reactions are carried out under an inert gas, preferably nitrogen or argon.

The term "q.s." means adding a quantity sufficient to achieve a stated function, e.g., to bring a solution to the desired volume (i.e., 100%).

It will also be appreciated that in each of the schemes below, the addition of any substituent may result in the production of a number of isomeric products (including, but not limited to, enantiomers or one or more diastereomers) any or all of which may be isolated and purified using conventional techniques.

Incorporation of a label into a compound or imaging agent described herein may be conducted by reacting an appropriate starting material(s) with a reagent including a radioactive isotope. Methods typically follow the same principles as standard organic chemical reactions, and may be carried out by any method known to those of skill in the art, including those provided in the present disclosure.

Scheme 1 provides exemplary synthetic routes for the synthesis of compounds provided herein (e.g., compounds of Formula I). The compounds of Formula I, or other formulas or compounds disclosed herein, are typically prepared by first preparing, e.g., Compound 1 or Compound 1a, and then attaching the desired substituents using suitable conditions (e.g., nucleophilic addition or cross coupling).

In some embodiments, synthesis of a compound described herein proceeds according to Scheme 1.

Scheme 1

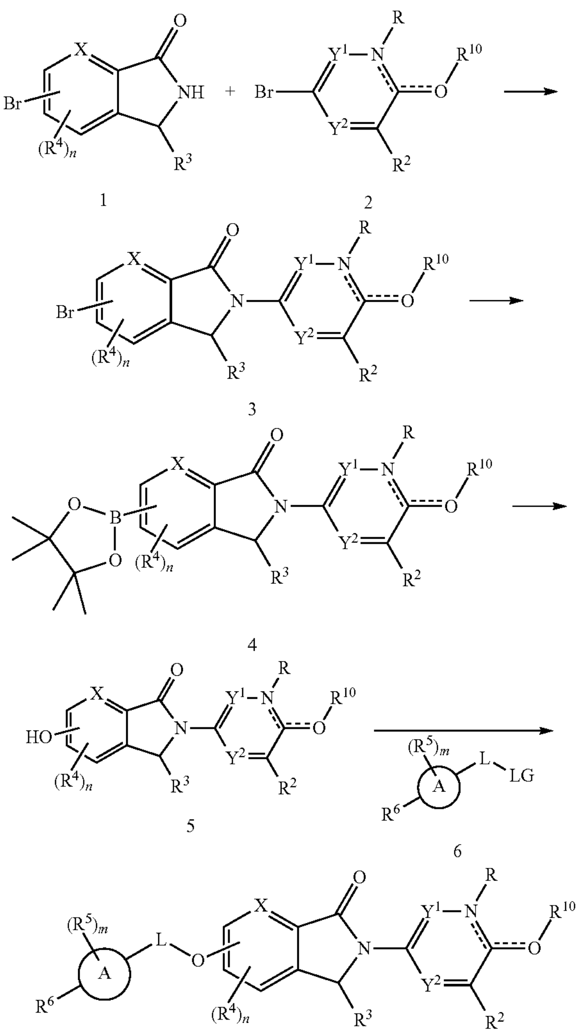

1 2 3 4 5 6 Formula I

In Scheme 1, $R^2$, $R^3$, $R^4$, $R^5$, $R^6$, $R^{10}$, $Y^1$, $Y^2$, L, X, m, n, and ring A are as defined herein. R is $R^1$ as defined herein, or R is a protecting group (e.g., a nitrogen protecting group as described in the Examples below). LG is a leaving group (e.g., halogen, triflate, mesylate, tosylate, or any other suitable leaving group).

In Scheme 1, when X is $CR^{11}$, where $R^{11}$ is as defined herein, compound 1 is prepared using methods known in the art and/or starting from commercially available dihydro isoindolinones and converted to the compound of Formula I by one or more steps. The dihydro isoindolinone 1 is coupled with compound 2 via a transition metal based coupling (e.g., in the presence of a palladium-based reagent such as $Pd_2(dba)_3$ or any other suitable reagent) in the presence of a base (e.g., potassium phosphate, cesium carbonate, or any other suitable base) to provide compound 3. It will be understood that a leaving group in compound 1, 2, or 3 (depicted as bromo in each instance) may be any other suitable leaving group (e.g., a triflate). Compound 3 is converted to a boronate 4 which is then converted to the hydroxy compound 5 using methods described in the Examples section below. The hydroxy compound 5 is O-alkylated with a compound 6 to provide a compound of Formula I. LG may be any suitable leaving group including and not limited to a chloro, iodo, bromo, or triflate group. In some embodiments, where $R^1$ is H in Formula I, a further deprotection step may be required to remove the protecting group on the nitrogen atom.

In some embodiments, synthesis of a compound described herein proceeds according to Scheme 2.

Scheme 2

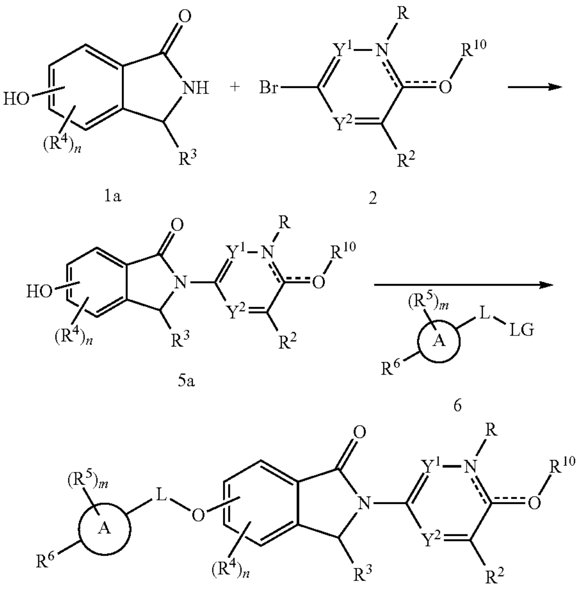

1a 2 5a 6 Formula I (X = CH)

Dihydro isoindolinone 1a may be used as a starting material (e.g., as obtained from a commercial source or by a process known in the art) and coupled with compound 2 to provide a compound 5a, then the hydroxy group of compound 5a may be O-alkylated with a compound 6 to provide a compound of Formula I.

A person of skill in the art will appreciate that any of compounds 1, 2, and 6 may be available from a commercial supplier for a particular embodiment. Alternatively, syntheses of compounds 1, 2, and 6 may be as described herein or as known to those of skill in the art.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

1. General Experimental Procedures

Commercially available reagents and solvents (HPLC grade) were used without further purification. $^1H$ NMR spectra were recorded on a Bruker DRX 500 MHz spectrometer or Bruker DPX 250 MHz spectrometer or a Bruker AVANCE 300 or on a Bruker AVANCE 500 spectrometer in deuterated solvents. Chemical shifts (6) are in parts per million Flash column chromatography refers to automated purification on Biotage Isolera systems using an appropriately sized SNAP or KPNH pre-packed silica columns and the solvents recorded in the experimental section; or on Isco Combiflash Rf systems using appropriately sized pre-packed silica columns and the solvents recorded in the experimental section. Reverse phase MPLC chromatography was performed on Isco Combiflash Rf systems using appropriately sized pre-packed C18 columns and the solvents recorded in the experimental section. Thin-layer chromatography (TLC) analysis was performed with Kieselgel 60 F254 (Merck) plates and visualized using UV light. SCX chromatography was performed with Biotage Isolute Flash SCX-2, loading the sample in methanol and eluting with methanol then 5% ammonia in methanol.

2. Analytical Methods

Acidic-Phase HPLC Methods

Analytical HPLC-MS (METCR1410) was performed on Shimadzu LCMS-2010EV systems using a reverse phase Kinetix Core-Shell C18 column (5 μm, 2.1×50 mm) at a column temp of 40° C., gradient 5-100% B (A=water/0.1% formic acid, B=acetonitrile/0.1% formic acid) over 1.2 min, then 100% B over 0.1 min, injection volume 3 μL, flow=1.2 mL/min. All other aspects of the method were unchanged.

Alternatively, (METCR1278) analytical HPLC-MS was performed on Shimadzu LCMS-2010EV systems using reverse phase Atlantis dC18 columns (3 μm, 2.1×50 mm), gradient 5-100% B (A=water/0.1% formic acid, B=acetonitrile/0.1% formic acid) over 3 minutes, injection volume 3 μL, flow=1.0 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 μm, 2.1 mm×100 mm at a column temp of 40° C., gradient 5-100% B (A=water/0.1% formic acid; B=acetonitrile/0.1% formic acid) over 5.3 min, then 100% B for 0.5 min, flow=0.6 mL/min. UV spectra were recorded at 215 nm using a Waters Acquity PDA detector. Mass spectra were obtained over the range m/z 150 to 850 at a sampling rate of 2 scans per second using a Waters ZQ. Data were integrated and reported using OpenLynx software.

Alternatively, (METCR1704) analytical UHPLC-MS were performed in reverse phase system using a Waters UPLCTM BEHTM C18 column (2.1 mm×50 mm, 1.7 μm; temperature: 40° C.), with an injection volume of 1 μL at a flow rate of 0.9 mL/min and a gradient of 5-100% B (A=0.1% formic acid in water; B=0.1% formic acid in acetonitrile) over 1.1 min, then 100% B for 0.25 min. A second gradient of 100-5% B was then applied over 0.05 min and held for 0.1 min. UV spectra were recorded at 215 nm, spectrum range: 200-400 nm. Mass spectra were obtained using a Waters SQD or QDA detector; ionization mode: electrospray positive or negative. Data were integrated and reported using Waters MassLynx and OpenLynx software.

Alternatively, UHPLC (MET-uHPLC-001) was performed on a Waters Acquity H-Class system using an Acquity UPLC BEH C18 column (1.7 μm, 2.1×75 mm), gradient 5-100% B (A=water/0.1% trifluoroacetic acid, B=acetonitrile/0.1% trifluoroacetic acid) at an ambient column temp (approx. 22° C.) over 6.0 min then 100% B for 2.0 min, flow=0.5 mL/min. UV spectra were recorded at 254 and 215 nm.

Alternatively, UHPLC (MET-uHPLC-002) was performed on a Waters Acquity H-Class system using an Acquity UPLC BEH C18 column (1.7 μm, 2.1×75 mm), gradient 5-100% B (A=water/0.1% trifluoroacetic acid, B=acetonitrile/0.1% trifluoroacetic acid) at an ambient column temp (approx. 22° C.) over 6.0 min then 100% B for 2.0 min, flow=0.4 mL/min. UV spectra were recorded at 254 and 215 nm.

Alternatively, analytical HPLC (MET-uHPLC-003) was performed on a Varian Pro Star 210 system using an XBridge C18 column (3.5 μm, 4.6×150 mm), gradient 5-100% B (A=water/0.1% trifluoroacetic acid, B=acetonitrile/0.1% trifluoroacetic acid) at an ambient column temp (approx. 22° C.) over 20.0 min then 100% B for 5.0 min, flow=1.0 mL/min. UV spectra were recorded at 254 and 215 nm using a Varian Pro Star 330 (PDA) detector.

Alternatively, analytical HPLC (MET-uHPLC-004) was performed on a Varian Pro Star 210 system using a Luna C18(2) column (5 μm, 4.6×250 mm), gradient 5-100% B (A=water/0.1% trifluoroacetic acid, B=acetonitrile/0.1% trifluoroacetic acid) at an ambient column temp (approx. 22° C.) over 20.0 min then 100% B for 5.0 min, flow=1.5 mL/min. UV spectra were recorded at 254 nm using a Varian Pro Star 330 (PDA) detector.

Alternatively, analytical HPLC (MET-uHPLC-005) was performed on a Varian Pro Star 210 system using a Luna C18(2) column (5 μm, 4.6×150 mm), gradient 5-90% B (A=water/0.1% trifluoroacetic acid, B=acetonitrile/0.1% trifluoroacetic acid) at an ambient column temp (approx. 22° C.) over 15.0 min then 90% B for 5.0 min, flow=1.15 mL/min. UV spectra were recorded at 254 and 215 nm using a Varian Pro Star 330 (PDA) detector.

Alternatively, mass spectra and LCMS analyses were obtained using a Waters Acquity SQD (ESI, UP-LCMS) system or an Agilent G6100A SQ LCMS system.

Basic-Phase HPLC Methods

Analytical HPLC-MS (METCR0990), was performed on Hewlett Packard HPLC systems using reverse phase Phenomenex Gemini C18 columns (3 μm, 2.0×50 mm), at a column temp of 60° C.; gradient 1-100% B (A=2 mM ammonium bicarbonate in water buffered to pH=10, B=acetonitrile) over 1.8 min then 100% B for 0.3 min, injection volume 3 μL, flow=1 mL/minute. UV spectra were recorded at 215 nm using a Waters PDA detector. Mass spectra were obtained over the range m/z 150 to 850 at a sampling rate of 2 scans per second using a Waters ZQ. Data were integrated and reported using OpenLynx software.

Analytical HPLC-MS (METCR1600), was performed on Hewlett Packard HPLC systems using reverse phase Phenomenex Gemini C18 columns (3 μm, 2.0×100 mm), gradient 5-100% B (A=2 mM ammonium bicarbonate in water buffered to pH=10, B=acetonitrile) over 5.5 min then 100% B for 0.4 min, injection volume 3 μL, flow=0.5 mL/minute. UV spectra were recorded at 215 nm using a Waters PDA detector. Mass spectra were obtained over the range m/z 150 to 850 at a sampling rate of 2 scans per second using a Waters ZQ. Data were integrated and reported using OpenLynx software.

Alternatively, (MET-uHPLC-AB-2005) analytical UHPLC-MS were performed in reverse phase using a Waters UPLCTM BEHTM C18 column (2.1 mm×30 mm, 1.7 μm; temperature 40° C.), with an injection volume of 1 μL at a flow rate of 1.0 mL/min and a gradient of 1-100% B (A=2 mM ammonium bicarbonate in water, buffered to pH=10; B=acetonitrile) over 1.1 min, then 100% B for 0.25 min. A second gradient of 100-1% B was then applied over 0.05 min and held for 0.4 min. UV spectra were recorded at 215 nm, spectrum range: 200-400 nm. Mass spectra were obtained using a Waters Quattro Premier XE mass detector or a Waters SQD2; ionization mode: electrospray positive or negative. Data were integrated and reported using Waters MassLynx and OpenLynx software.

Alternatively, UHPLC (MET-uHPLC-006) was performed on a Waters Acquity H-Class system using an Acquity UPLC BEH C18 column (1.7 μm, 2.1×75 mm), gradient 5-100% B (10 mM ammonium formate in water buffered to pH=10 with ammonium hydroxide, B=95:5 acetonitrile/water) at an ambient column temp (approx. 22° C.) over 6.0 min then 100% B for 2.0 min, flow=0.4 mL/min. UV spectra were recorded at 254 and 215 nm.

All example compounds display an LC purity of >95% unless stated otherwise.

Preparative HPLC Methods

Preparative HPLC separations were performed on a Varian Prep HPLC system using Varian SD-1 preparative LC pumps and ProStar 325 UV/Vis Detector. An XBridge Prep C18 OBD column (5 μm, 19×250 mm) was used, eluted according to solvent gradient Method 2.

| Method 2 | | | |
|---|---|---|---|
| Time (min) | Flow (mL/min) | % A | % B |
| 0.0 | 5 | 95 | 5 |
| 0.5 | 5 | 95 | 5 |
| 1.0 | 20 | 95 | 5 |
| 4.0 | 20 | 95 | 5 |
| 44.0 | 20 | 0 | 100 |

A = Water with v/v 0.1% formic acid
B = Acetonitrile

Intermediates

Intermediate 1: (5-(Fluoromethoxy)pyridin-2-yl)methanol

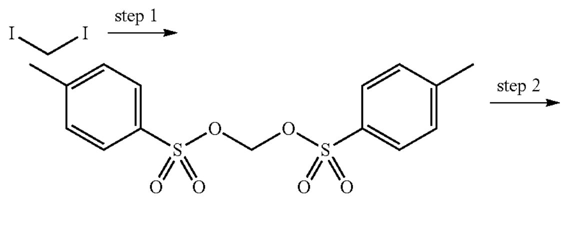

-continued

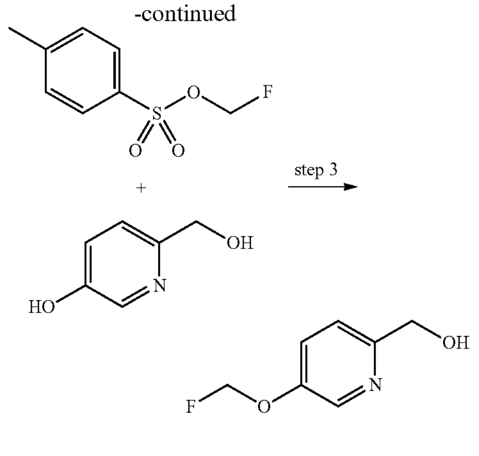

Step 1: Methylene bis(4-methylbenzenesulfonate)

A mixture of silver p-toluenesulfonate (11.5 g, 41.1 mmol) and MeCN (43.4 mL) was treated with diiodomethane (5.00 g, 18.7 mmol), and the mixture was stirred at reflux for 16 h. After this time, the mixture was cooled to ambient temperature, filtered, and the filter cake washed with MeCN (3×20 mL). The filtrate was concentrated in vacuo. DCM (40 mL) was added to the residue, the suspension was filtered, and the filter cake was washed with DCM (3×20 mL). The filtrate was concentrated in vacuo, and the residue obtained was recrystallized from EtOH (30 mL). The isolated product was dried in vacuo to afford the title compound (4.09 g, 62%). $^1$H NMR (300 MHz, $CDCl_3$) 7.59 (d, J=8.4 Hz, 4H), 7.25 (d, J=8.7 Hz, 4H), 5.81 (s, 2H), 2.45 (s, 6H).

Step 2: Fluoromethyl 4-methylbenzenesulfonate

A mixture of methylene bis(4-methylbenzenesulfonate) (4.09 g, 11.5 mmol) and MeCN (26.7 mL) was treated with 1 M TBAF in THF (12.6 mL, 12.6 mmol), and the mixture was stirred at reflux for 2 h. After this time, the solvent was removed in vacuo, and the residue obtained was dissolved in EtOAc (40 mL). The solution was washed with brine (40 mL), dried over sodium sulfate, filtered, and concentrated in vacuo. The residue obtained was purified by FCC (silica, 0-50% EtOAc in heptane) to afford the title compound (609 mg, 26%). $^1$H NMR (300 MHz, $CDCl_3$) 7.84 (d, J=8.4 Hz, 2H), 7.36 (d, J=8.1 Hz, 2H), 5.74 (d, J=51.0 Hz, 2H), 2.64 (s, 3H).

Step 3: (5-(Fluoromethoxy)pyridin-2-yl)methanol

A mixture of 6-(hydroxymethyl)pyridin-3-ol (300 mg, 2.40 mmol), fluoromethyl 4-methylbenzenesulfonate (588 mg, 2.88 mmol), and acetone (9.0 mL) was treated with potassium carbonate (994 mg, 7.19 mmol), and the mixture was heated at 70° C. for 16 h. After this time, the mixture was cooled to ambient temperature and extracted with DCM (3×40 mL). The combined organic layers were dried over sodium sulfate, filtered, and the filtrate was concentrated in vacuo. The residue obtained was purified by FCC (silica, 0-5% MeOH in DCM) to afford the title compound (108 mg, 29%). $^1$H NMR (300 MHz, DMSO-$d_6$) 8.32 (d, J=3.0 Hz, 1H), 7.58 (dd, J=8.7, 2.7 Hz, 1H), 7.46 (d, J=8.7 Hz, 1H), 5.90 (d, J=54.0 Hz, 2H), 5.41 (t, J=5.7 Hz, 1H), 4.52 (d, J=5.7 Hz, 2H).

Intermediate 2: 2((6-(Chloromethyl)pyridin-3-yl)oxy)ethyl-1,1,2,2-$d_4$ 4-methylbenzenesulfonate

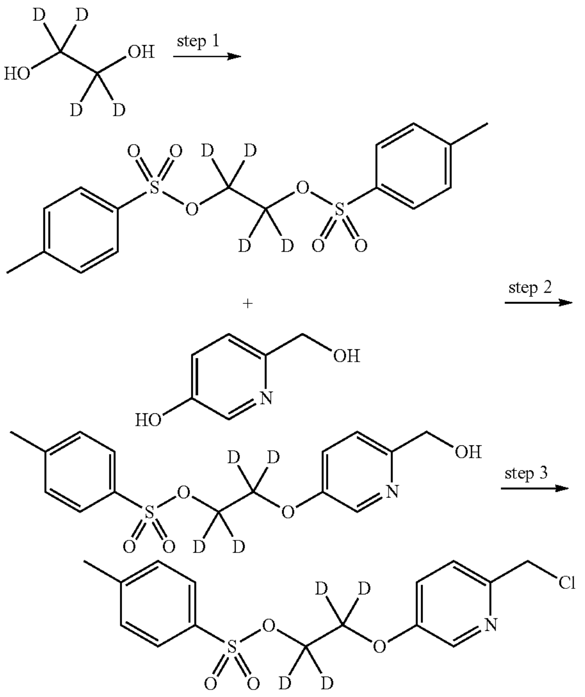

Step 1: Ethane-1,2-diyl-$d_4$ bis(4-methylbenzenesulfonate)

p-Toluenesulfonyl chloride (5.77 g, 30.3 mmol) was added to a mixture of ethylene glycol-$d_4$ (0.673 mL, 12.1 mmol) and triethylamine (8.41 mL, 60.5 mmol) in DCM (80 mL), and the mixture was stirred at room temperature for 16 h. After this time, DCM (40 mL) was added, and the mixture was washed with water (100 mL). The aqueous layer was extracted with DCM (100 mL), and the combined organic layers were dried over sodium sulfate, filtered, and concentrated in vacuo. The residue obtained was purified by FCC (silica, 0-5% EtOAc in DCM) to afford the title compound (3.84 g, 85%). $^1H$ NMR (300 MHz, $CDCl_3$) 7.74 (d, J=8.4 Hz, 4H), 7.34 (d, J=7.8 Hz, 4H), 2.46 (s, 6H). MS ($ES^+$) $(M+H)^+$ 375.

Step 2: 2-((6-(Hydroxymethyl)pyridin-3-yl)oxy)ethyl-1,1,2,2-$d_4$ 4-methylbenzenesulfonate Ethane-1,2-diyl-$d_4$ bis(4-methylbenzenesulfonate) (4.51 g, 11.8 mmol) was added to a mixture of 6-(hydroxymethyl)pyridin-3-ol (492 mg, 3.93 mmol) and cesium carbonate (3.84 g, 11.8 mmol) in MeCN (49.3 mL), and the mixture was stirred at 80° C. for 2.5 h. After this time, the reaction mixture was cooled and filtered through diatomaceous earth. The filter cake was rinsed with EtOAc (2×50 mL), and the filtrate was concentrated in vacuo. The residue obtained was purified by FCC (silica, 0-5% MeOH in DCM) to afford the title compound (450 mg, 34%). $^1H$ NMR (300 MHz, $CDCl_3$) 8.13 (dd, J=2.4, 0.9 Hz, 1H), 7.83-7.80 (m, 2H), 7.35 (d, J=7.8 Hz, 2H), 7.18-7.11 (m, 2H), 4.70 (s, 2H), 3.34 (br s, 1H), 2.46 (s, 3H).

Step 3: 2-((6-(Chloromethyl)pyridin-3-yl)oxy)ethyl-1,1,2,2-$d_4$ 4-methylbenzenesulfonate Thionyl chloride (0.197 mL, 2.70 mmol) was added to a mixture of 2-((6-(hydroxymethyl)pyridin-3-yl)oxy)ethyl-1,1,2,2-$d_4$ 4-methylbenzenesulfonate (450 mg, 1.35 mmol) in DCM (9.4 mL) at 0° C., and the solution was stirred at 0° C. for 1 h. After this time, water (25 mL) was added, the layers were separated, and the aqueous layer was extracted with DCM (2×25 mL). The combined organic layers were dried over sodium sulfate, filtered, and concentrated in vacuo to afford the title compound (475 mg, 99%). $^1H$ NMR (300 MHz, $CDCl_3$) 8.13 (d, J=2.7 Hz, 1H), 7.83-7.80 (m, 2H), 7.37-7.34 (m, 3H), 7.12 (dd, J=8.4, 3.0 Hz, 1H), 4.63 (s, 2H), 2.46 (s, 3H).

Intermediate 3: 2-(Chloromethyl)-5-(2-fluoroethoxy-1,1,2,2-$d_4$)pyridine

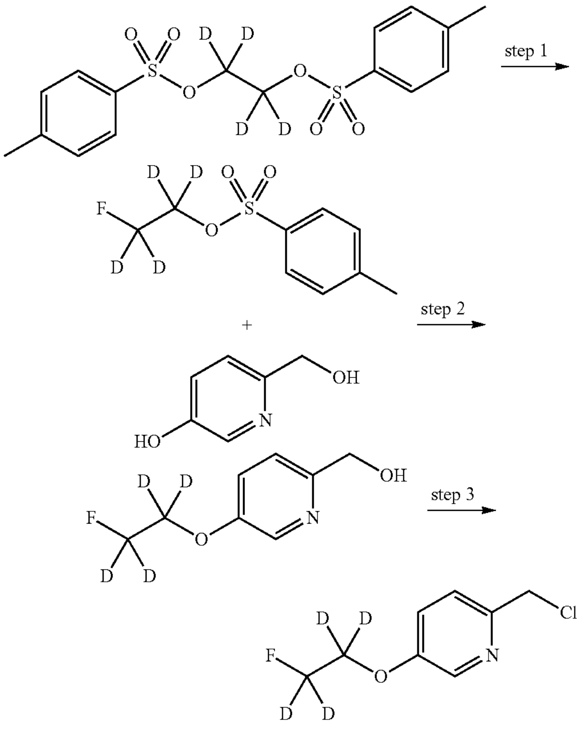

Step 1: 2-Fluoroethyl-1,1,2,2-$d_4$ 4-methylbenzenesulfonate

TBAF, 1.0 M in THF (8.97 mL, 8.97 mmol) was added to ethane-1,2-diyl-$d_4$ bis(4-methyl-benzenesulfonate) (2.80 g, 7.48 mmol) in MeCN (17.4 mL), and the mixture was stirred at reflux for 2 h. After this time, the mixture was cooled, diluted with DCM (100 mL), and washed with water (40 mL). The aqueous layer was extracted with DCM (100 mL), and the combined organic layers were dried over sodium sulfate, filtered, and the filtrate was concentrated in vacuo. The residue obtained was purified by FCC (silica, 0-100% DCM in heptane) to afford the title compound (601 mg, 36%). $^1H$ NMR (300 MHz, $CDCl_3$) 7.36 (d, J=8.1 Hz, 2H), 7.82 (d, J=8.4 Hz, 2H), 2.46 (s, 3H).

Step 2: (5-(2-Fluoroethoxy-1,1,2,2-$d_4$)pyridin-2-yl)methanol

A mixture of 2-fluoroethyl-1,1,2,2-$d_4$ 4-methylbenzenesulfonate (363 mg, 1.60 mmol), 6-(hydroxymethyl)pyridin-3-ol (200 mg, 1.60 mmol) and cesium carbonate (1.56 g, 4.80 mmol) in MeCN (20.0 mL) was stirred at 80° C. for 2.5 h. After this time, the reaction mixture was cooled and filtered through diatomaceous earth. The filter cake was rinsed with EtOAc (2×50 mL), and the filtrate was concentrated in vacuo. The residue obtained was purified by FCC (silica, 0-5% MeOH in DCM) to afford the title compound (133 mg, 47%). $^1$H NMR (300 MHz, $CDCl_3$) 8.29 (d, J=2.7 Hz, 1H), 7.29-7.19 (m, 2H), 4.72 (s, 2H), 3.39 (br s, 1H).

Step 3: 2-(Chloromethyl)-5-(2-fluoroethoxy-1,1,2,2-$d_4$)pyridine

Thionyl chloride (0.139 mL, 1.91 mmol) was added to a mixture of (5-(2-fluoroethoxy-1,1,2,2-$d_4$)pyridin-2-yl)methanol (167 mg, 0.953 mmol) in DCM (6.7 mL), and the mixture was stirred at 0° C. for 1 h. After this time, the mixture was poured into water (25 mL), the layers were separated, and the aqueous layer was extracted with DCM (2×25 mL). The combined organic layers were dried over sodium sulfate, filtered, and concentrated in vacuo to afford the title compound (180 mg, 98%). $^1$H NMR (300 MHz, $CDCl_3$) 8.30 (d, J=2.7 Hz, 1H), 7.48 (d, J=8.7 Hz, 1H), 7.36 (dd, J=8.7, 3.0 Hz, 1H), 4.72 (s, 2H).

Intermediate 4: 4-Chloro-2-(chloromethyl)-5-methoxypyridine

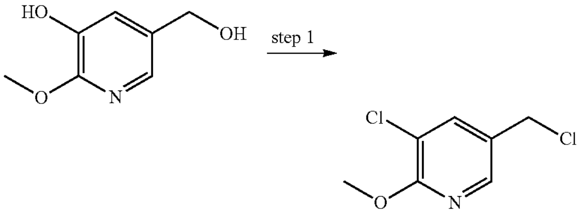

To a solution of 2-(hydroxymethyl)-5-methoxypyridin-4-ol (50 mg, 0.32 mmol) in MeCN (2 mL) was added phosphorus oxychloride (0.090 mL, 0.98 mmol), and the mixture was heated at 70° C. for 22 h. After this time, additional phosphorus oxychloride (0.090 mL, 0.98 mmol) was added, and heating was continued for 20 h. A third portion of phosphorus oxychloride (0.090 mL, 0.98 mmol) was then added, and heating continued for 20 h. After this time, the volatiles were removed under reduced pressure, and the residue obtained was diluted with EtOAc (20 mL) and neutralized with sat. sodium bicarbonate solution. The layers were separated, and the aqueous layer was extracted with EtOAc (10 mL). The combined organic layers were dried over anhydrous sodium sulfate, filtered, and concentrated under reduced pressure. The residue obtained was purified by FCC (silica, 0-10% MeOH in DCM) to afford the title compound (22 mg, 35%). $^1$H NMR (300 MHz, $CDCl_3$) 8.22 (s, 1H), 7.49 (s, 1H), 4.61 (s, 2H), 4.01 (s, 3H). MS (ES$^+$) (M+H)$^+$ 192.

Intermediate 5: 2-(Chloromethyl)-5-(1-fluoroethoxy)pyridine hydrochloride

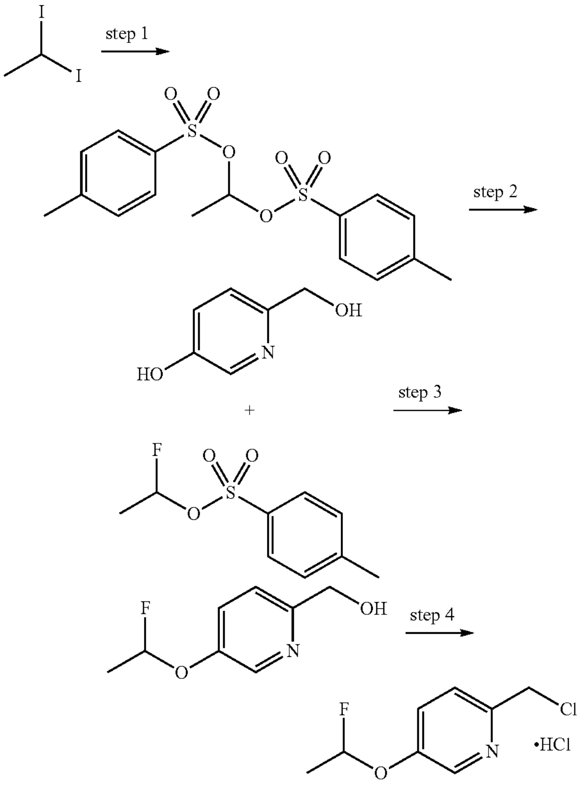

Step 1: Ethane-1,1-diyl bis(4-methylbenzenesulfonate)

A mixture of 1,1-diiodoethane (500 mg, 1.77 mmol) and silver p-toluenesulfonate (990 mg, 3.55 mmol) in MeCN (20 mL) was stirred at rt for 3 d. After this time, the volatiles were removed under vacuum, and the residue obtained was suspended in DCM. The solids were removed by filtration, and the filtrate was concentrated under vacuum at rt to afford the title compound (570 mg, 87%). $^1$H NMR (300 MHz, $CDCl_3$) 7.70 (d, J=8.3 Hz, 4H), 7.31 (d, J=8.1 Hz, 4H), 6.39 (q, J=5.3 Hz, 1H), 2.45 (s, 6H), 1.54 (d, J=5.3 Hz, 3H).

Step 2: 1-Fluoroethyl 4-methylbenzenesulfonate

A mixture of ethane-1,1-diyl bis(4-methylbenzenesulfonate) (550 mg, 1.48 mmol) and TBAF (1 M in THF, 1.63 mL, 1.63 mmol) in THF (30 mL) was stirred at rt for 5 d. After this time, the solvent was removed under reduced pressure, and the residue obtained was purified by FCC (silica, 0-10% EtOAc in hexanes) to afford the title compound (67 mg, 20%). $^1$H NMR (300 MHz, $CDCl_3$) 7.82 (d, J=8.3 Hz, 2H), 7.35 (d, J=8.4 Hz, 2H), 6.23 (dq, J=57.0, 5.0 Hz, 1H), 2.45 (s, 3H), 1.56 (dd, J=20.6, 5.5 Hz, 3H).

Step 3: (5-(1-Fluoroethoxy)pyridin-2-yl)methanol

To a mixture of 6-(hydroxymethyl)pyridin-3-ol (103 mg, 0.825 mmol) and potassium hydrogen carbonate (165 mg, 1.65 mmol) in DMF (10 mL) at rt was added 1-fluoroethyl 4-methylbenzene-sulfonate (60 mg, 0.27 mmol), and the mixture was heated at 100° C. overnight. After this time, the solvent was removed under reduced pressure, and the residue obtained was purified by FCC (silica, 0-50% MeOH in EtOAc) to afford the title compound (20 mg, 42%). $^1$H NMR (300 MHz, $CDCl_3$) 8.38 (d, J=2.5 Hz, 1H), 7.42 (dd, J=8.3, 2.2 Hz, 1H), 7.24 (d, J=8.6 Hz, 1H), 5.94 (dq, J=62.3, 4.8 Hz, 1H), 4.73 (s, 2H), 1.69 (dd, J=20.0, 4.9 Hz, 3H). MS ($ES^+$) $(M+H)^+$ 172.

Step 4: 2-(Chloromethyl)-5-(1-fluoroethoxy)pyridine hydrochloride

To a mixture of (5-(1-fluoroethoxy)pyridin-2-yl)methanol (16 mg, 0.093 mmol) in DCM (5 mL) at rt was added thionyl chloride (111 mg, 0.930 mmol), and the mixture was stirred at rt for 1 h. After this time, the solvent was removed under reduced pressure to afford the title compound (23 mg, >99%). $^1$H NMR (300 MHz, $CD_3OD$) 8.30 (d, J=2.5 Hz, 1H), 7.63-7.50 (m, 2H), 6.14 (dq, J=61.9, 4.8 Hz, 1H), 4.67 (s, 2H), 1.65 (dd, J=20.2, 4.8 Hz, 3H). MS ($ES^+$) $(M+H)^+$ 190.

Intermediate 6: 6-Bromo-2-(2-fluoroethyl)pyridazin-3(2H)-one

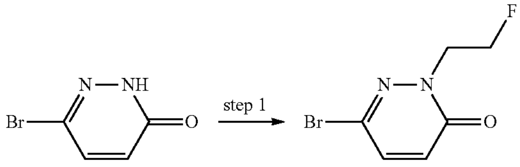 [SMILES: O=c1ccc(Br)n[nH]1 ; O=c1ccc(Br)nn1CCF]

To 6-bromopyridazin-3(2H)-one (50 mg, 0.29 mmol) in a reaction vial was added potassium carbonate (79 mg, 0.57 mmol) followed by DMF (1 mL) and a solution of 1-bromo-2-fluoroethane (58 mg, 0.46 mmol) in 1,4-dioxane (2 mL). The reaction vial was sealed and heated at 130° C. for 1 h. After this time, the reaction mixture was cooled to room temperature and concentrated to dryness under reduced pressure. The residue obtained was purified by FCC (silica, 0-50% EtOAc in hexanes) to afford the title compound (48 mg, 76%). $^1$H NMR (300 MHz, $CDCl_3$) 7.29 (d, J=9.9 Hz, 1H), 6.84 (d, J=9.6 Hz, 1H), 4.79 (dt, J=47.1, 5.0 Hz, 2H), 4.44 (dt, J=24.6, 5.0 Hz, 2H). $^{19}$F NMR (282 MHz, $CDCl_3$) −225.67. MS ($ES^+$) $(M+H)^+$ 221. Intermediate 7: 6-(Chloromethyl)-2-fluoro-3-methoxy-pyridine

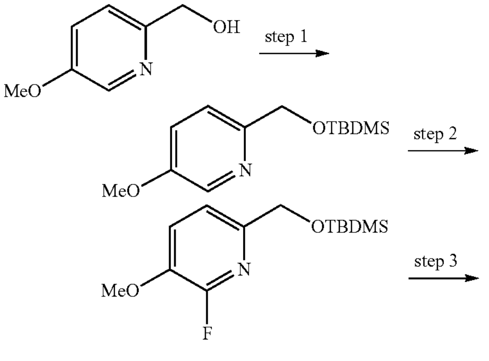

-continued

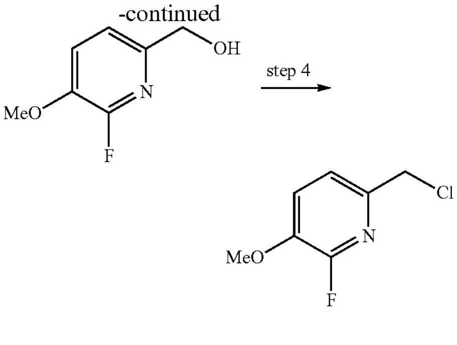

Step 1: tert-Butyl-[(5-methoxy-2-pyridyl)methoxy]-dimethyl-silane (5-Methoxypyridin-2-yl)methanol (750 mg, 5.39 mmol) and imidazole (404 mg, 5.93 mmol) were dissolved in DCM (20 mL) and tert-butyl(chloro)dimethylsilane (2.03 g, 13.5 mmol) was added. The reaction was stirred at rt for 4 h. The reaction mixture was diluted with $H_2O$ (15 mL) and the organic fraction extracted. The aqueous phase was re-extracted with DCM (10 mL) and the combined organics were washed with brine solution (10 mL), dried over $Na_2SO_4$, filtered, and concentrated in vacuo. The crude residue was purified by FCC (silica, 0-100% EtOAc in heptane) to afford the title compound (1.26 g, 83% yield). $^1$H NMR (400 MHz, DMSO) δ 8.19 (d, J=2.5 Hz, 1H), 7.41 (dd, J=8.6, 2.9 Hz, 1H), 7.38-7.31 (m, 1H), 4.68 (s, 2H), 3.81 (s, 3H), 0.90 (s, 9H), 0.07 (s, 6H). Tr(METCR1704)=1.00 min, m/z (ES)+ [M+H]+=254.2, 100%.

Step 2: tert-Butyl-[(6-fluoro-5-methoxy-2-pyridyl) methoxy]-dimethyl-silane

To a solution of tert-butyl-[(5-methoxy-2-pyridyl) methoxy]-dimethyl-silane (400 mg, 1.58 mmol) in anhydrous THF (10 mL) at −78° C. was added 2.5 M butyllithium (0.82 mL, 2.05 mmol), and the reaction mixture was stirred for 1 h. N-fluoro-N-(phenylsulfonyl)benzenesulfonamide (647 mg, 2.05 mmol) was then added, and the reaction mixture was warmed to rt and stirred for 1.5 h. The reaction mixture was diluted with brine solution and EtOAc, and the organic fraction extracted. The combined organics were dried over $Na_2SO_4$, filtered, and concentrated in vacuo. The crude residue was purified by FCC (silica, 0-100% EtOAc in heptane) to afford the title compound (84 mg, 18% yield). $^1$H NMR (400 MHz, DMSO) δ 7.66 (dd, J=10.6, 8.1 Hz, 1H), 7.29 (d, J=8.1 Hz, 1H), 4.60 (s, 2H), 3.86 (s, 3H), 0.90 (s, 9H), 0.08 (s, 6H). Tr(METCR1704)=1.18 min, m/z (ES)+ [M+H]+=272.1, 90%.

Step 3: (6-Fluoro-5-methoxy-2-pyridyl)methanol

To a solution of tert-butyl-[(6-fluoro-5-methoxy-2-pyridyl)methoxy]-dimethyl-silane (84 mg, 0.31 mmol) in THF (2 mL) at rt was added 1 M TBAF in THF (0.31 mL, 0.31 mmol), and the reaction mixture was stirred for 1 h. The reaction mixture was diluted with a saturated ammonium chloride solution (3 mL) and the product extracted with EtOAc (2×5 mL). The combined organics were dried over $Na_2SO_4$, filtered, and concentrated in vacuo. The crude residue was purified by column chromatography (silica, 0-100% EtOAc in heptane) to afford the title compound (40 mg, 77% yield). Tr(METCR1704)=0.45 min, m/z (ES)+ [M+H]+=158.0, 94%.

Step 4: 6-(Chloromethyl)-2-fluoro-3-methoxy-pyridine (6-Fluoro-5-methoxy-2-pyridyl)methanol (40 mg, 0.255 mmol) was dissolved in DCM (2 mL) and thionyl chloride (0.19 mL, 2.55 mmol) was added. The reaction was stirred at rt for 3 h. The reaction mixture was concentrated in vacuo and azeotroped with DCM (×2) and $Et_2O$ to afford the title compound (50 mg, 98% yield). Tr(METCR1704)=0.74 min, m/z (ES)+ [M+H]+=176.0, 177.9, 88%.

Intermediate 8: 2-(Chloromethyl)-4-fluoro-5-methoxy-pyridine

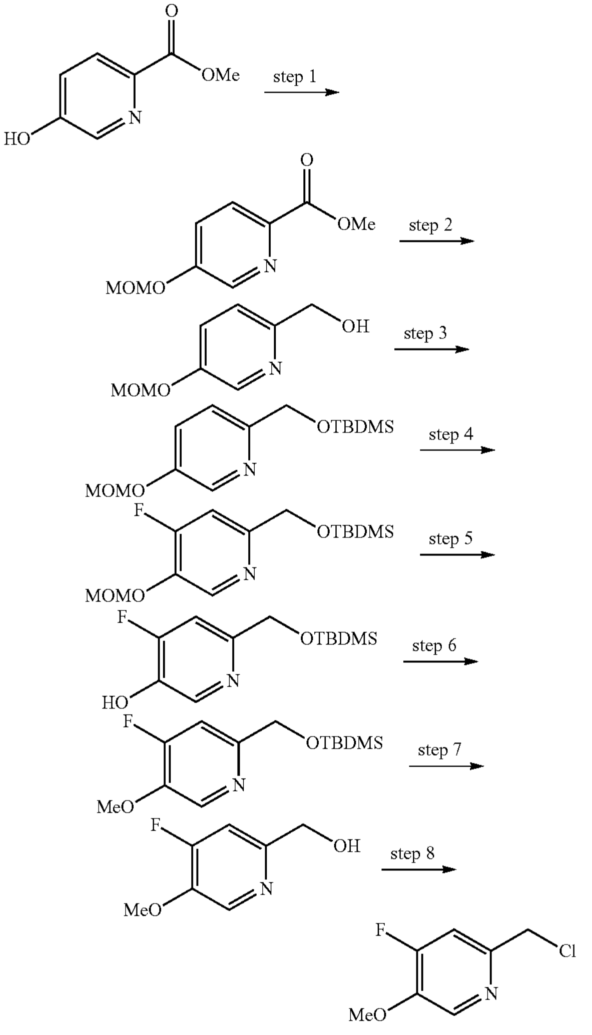

Step 1: Methyl 5-(methoxymethoxy)pyridine-2-carboxylate

To an RBF at rt under $N_2$ containing THF (60 mL) were successively added triethylamine (6.8 mL, 49.0 mmol), methyl 5-hydroxypyridine-2-carboxylate (5.00 g, 32.6 mmol) in one portion, followed by chloro(methoxy)methane (3.7 mL, 49.0 mmol) dropwise over 5 minutes. The mixture was flushed with $N_2$ to evacuate all fumes and the resulting suspension was stirred at rt overnight. The reaction was quenched by pouring onto water (50 mL). After extraction with EtOAc (2×50 mL), the combined organics were washed with brine (50 mL), dried ($MgSO_4$), filtered, and concentrated in vacuo. The crude residue (pale yellow solid) was purified by column chromatography (Biotage Sfar Duo 50 g cartridge, 0-40% EtOAc in heptane, product eluted with 30% EtOAc) to give the title compound (5.50 g, 83% yield). $^1$H NMR (500 MHz, DMSO) δ 8.43 (d, J=2.8 Hz, 1H), 8.04 (d, J=8.7 Hz, 1H), 7.59 (dd, J=8.7, 2.9 Hz, 1H), 5.36 (s, 2H), 3.85 (s, 3H), 3.41 (s, 3H). Tr(METCR1704)=0.55 min, m/z (ES$^+$) [M+H]$^+$=198.0, 97%.

Step 2: [5-(Methoxymethoxy)-2-pyridyl]methanol

A solution of methyl 5-(methoxymethoxy)pyridine-2-carboxylate (5.50 g, 27.9 mmol) in anhydrous toluene (200 mL) under nitrogen was cooled to −78° C. and DIBAL (1 M in heptane, 73 mL, 73 mmol) was added over 45 minutes. The reaction was warmed to 0° C. and stirred for 2 hours. The reaction was re-treated with more DIBAL (1 M in heptane, 11 mL, 11 mmol) at 0° C., and stirring was continued for another 1 hour. The reaction was quenched by addition of water (50 mL). EtOAc was added (200 mL). Following addition of $MgSO_4$, the mixture was filtered, eluted with further EtOAc, and the filtrate was concentrated to give the title compound (2.50 g, 48% yield). $^1$H NMR (500 MHz, DMSO) δ 8.23 (d, J=2.7 Hz, 1H), 7.46 (dd, J=8.6, 2.8 Hz, 1H), 7.39 (d, J=8.6 Hz, 1H), 5.31 (t, J=5.8 Hz, 1H), 5.23 (s, 2H), 4.49 (d, J=5.8 Hz, 2H), 3.38 (s, 3H). Tr(MET-uHPLC-AB-2005)=0.38 min m/z (ES$^+$)(M+H)$^+$ 470, 91%.

Step 3: tert-Butyl-[[5-(methoxymethoxy)-2-pyridyl]methoxy]-dimethyl-silane

[5-(Methoxymethoxy)-2-pyridyl]methanol (2.50 g, 14.8 mmol) and 1H-imidazole (1.1 g, 16.3 mmol) were dissolved in DCM (100 mL) and tert-butyl(chloro)dimethylsilane (2.90 g, 19.2 mmol) was added. The reaction was stirred at rt for 2 hours. More 1H-imidazole (250 mg, 3.7 mmol) and tert-butyl(chloro)dimethylsilane (500 mg, 3.3 mmol) were added, and stirring was continued at rt for another 1.75 hours. The reaction mixture was diluted with water (50 mL). After separation, the aqueous phase was extracted with $CH_2Cl_2$ (2×50 mL) and the combined organics were washed with brine solution (50 mL), dried ($MgSO_4$), filtered, and concentrated in vacuo. The crude residue was purified by column chromatography using Biotage Sfar Duo 2×25 g cartridge, 0-40% EtOAc in heptane to give the title compound (3.5 g, 84%). $^1$H NMR (500 MHz, DMSO) δ 8.25 (d, J=2.7 Hz, 1H), 7.49 (dd, J=8.6, 2.9 Hz, 1H), 7.36 (d, 1H), 5.23 (s, 2H), 4.68 (s, 2H), 3.38 (s, 3H), 0.90 (s, 9H), 0.08 (s, 6H). Tr(METCR1704)=1.03 min, m/z (ES$^+$) [M+H]$^+$=284.2, 100%.

Step 4: tert-Butyl-[[4-fluoro-5-(methoxymethoxy)-2-pyridyl]methoxy]-dimethyl-silane To a solution of tert-butyl-[[5-(methoxymethoxy)-2-pyridyl]methoxy]-dimethyl-silane (2.2 g, 7.06 mmol) in anhydrous THF (35 mL) at −78° C. was added N-butyllithium (2.5 M in hexanes, 3.7 mL, 9.17 mmol), and the reaction mixture was stirred for 1 hour at that temperature. N-fluoro-N-(phenylsulfonyl)benzenesulfonamide (NFSI) (2.89 g, 9.17 mmol) was then added directly as a solid over 10 seconds and the reaction mixture was warmed to room temperature and stirred for 40 minutes. The reaction was quenched by pouring onto brine solution (50 mL). After extraction with EtOAc (2×40 mL), the combined organic extracts were dried ($MgSO_4$), filtered, and concentrated in vacuo. The residue was purified by FCC using Biotage Isolera (Sfar Duo 25 g, 2-30% EtOAc in heptane, loading with DCM) to give the title compound (1.4 g, 55% yield). $^1$H NMR (400 MHz, $CDCl_3$) δ 8.39 (d, J=10.0 Hz, 1H), 7.28-7.25 (m, 1H), 5.21 (s, 2H), 4.75 (d, J=0.7 Hz, 2H), 3.54 (s, 3H), 0.95 (s, 9H), 0.12 (s, 6H). Tr(METCR1704)=1.13 min, m/z ($ES^+$) $[M+H]^+$=302.2, 68%.

Step 5: 6-[[tert-Butyl(dimethyl)silyl]oxymethyl]-4-fluoro-pyridin-3-ol

To a solution of tert-butyl-[[4-fluoro-5-(methoxymethoxy)-2-pyridyl]methoxy]-dimethyl-silane (1013 mg, 3.36 mmol) in DCM (20.26 mL) was added zinc dibromide (1.5 g, 6.72 mmol) and propane-1-thiol (0.61 mL, 6.72 mmol). The mixture was stirred at rt for 3 hours. The reaction was cooled to 0° C. before it was quenched by addition of saturated aqueous $NaHCO_3$ (10 mL). Stirred for 15 minutes at 0° C. Water (25 mL) was added and, after extraction with DCM (3×30 mL), the combined organic extracts were washed with brine (30 mL), dried ($MgSO_4$), filtered, and concentrated to give a dark orange oil. The residue was purified by FCC using Biotage Isolera (Sfar Duo 50 g, 12-80% EtOAc in heptane, loading with DCM) to give the title compound (388 mg, 43% yield). $^1$H NMR (400 MHz, $CDCl_3$) δ 8.24 (d, J=10.3 Hz, 1H), 7.27 (d, J=11.3 Hz, 1H), 4.75 (s, 2H), 0.95 (s, 9H), 0.11 (s, 6H). Tr(METCR1704)=0.91 min, m/z ($ES^+$) $[M+H]^+$=258.2, 94%.

Step 6: tert-Butyl-[(4-fluoro-5-methoxy-2-pyridyl) methoxy]-dimethyl-silane

To a solution of 6-[[tert-butyl(dimethyl)silyl]oxymethyl]-4-fluoro-pyridin-3-ol (385 mg, 1.50 mmol) in DMF (5 mL) was added caesium carbonate (585 mg, 1.80 mmol), followed by iodomethane (0.11 mL, 1.80 mmol). The mixture was heated to 35° C. and stirred at that temperature for 3 hours. After cooling, the reaction was quenched by pouring onto saturated aqueous $NaHCO_3$ (10 mL) and water (10 mL) was added. After extraction with $Et_2O$ (3×20 mL), the combined organic extracts were washed with brine (15 mL), dried ($MgSO_4$), filtered, and concentrated in vacuo. The residue was purified by FCC using Biotage Isolera (10 g, 2-30% EtOAc in heptane, loading with DCM) to give the tile compound (243 mg, 59% yield) as colourless free-flowing oil. $^1$H NMR (400 MHz, $CDCl_3$) δ 8.21 (d, J=10.1 Hz, 1H), 7.26-7.23 (m, 1H), 4.74 (s, 2H), 3.96 (s, 3H), 0.95 (s, 9H), 0.12 (s, 6H). Tr(METCR1704)=1.11 min, m/z ($ES^+$) $[M+H]^+$=272.2, 98%.

Step 7: (4-Fluoro-5-methoxy-2-pyridyl)methanol

To a solution of tert-butyl-[(4-fluoro-5-methoxy-2-pyridyl)methoxy]-dimethyl-silane (98%, 243 mg, 0.877 mmol) in THF (6 mL) at 5° C. was added TBAF (1 M in THF, 1.1 mL, 1.05 mmol), and the solution was stirred at 5-10° C. for 1.5 hours. The reaction was quenched by pouring onto aq. sat $NaHCO_3$ (10 mL). Water (10 mL) and EtOAc (10 mL) were added. Poor separation, therefore brine (5 mL) was added. After separation, the aqueous phase was extracted with EtOAc (2×10 mL). The combined organic extracts were washed with brine (15 mL), dried ($MgSO_4$), filtered, and concentrated in vacuo. The residue was purified by FCC using Biotage Isolera (10 g, 5-30% methanol in DCM, loading with DCM) to give the title compound (125 mg, 86% yield). $^1$H NMR (400 MHz, $CDCl_3$) δ 8.26 (d, J=9.9 Hz, 1H), 7.03 (d, J=11.0 Hz, 1H), 4.69 (d, J=3.8 Hz, 2H), 3.98 (s, 3H), 3.34 (s, 1H). Tr(MET-uHPLC-AB-2005)=0.38 min m/z ($ES^+$) $(M+H)^+$158.1, 95%.

Step 8: 2-(Chloromethyl)-4-fluoro-5-methoxy-pyridine (4-Fluoro-5-methoxy-2-pyridyl)methanol (30 mg, 0.191 mmol) was dissolved in DCM (1.5 mL) and thionyl chloride (0.07 mL, 0.955 mmol) was added. The reaction was stirred at room temperature for 2 h. The reaction mixture was concentrated under a stream of $N_2$. Trituration with $Et_2O$ (2×) and evaporation of the volatiles (under a stream of $N_2$), followed by drying in the vac oven afforded the title compound (33 mg, 95% yield). $^1$H NMR (400 MHz, $CDCl_3$) δ 8.42 (s, 1H), 7.67 (d, J=8.5 Hz, 1H), 5.08 (s, 2H), 4.12 (s, 3H). Tr(METCR1704)=0.66 min, m/z ($ES^+$) $(M+H)^+$=176.0, 178.0, 96%.

Methods

Method 1

Scheme for Method 1

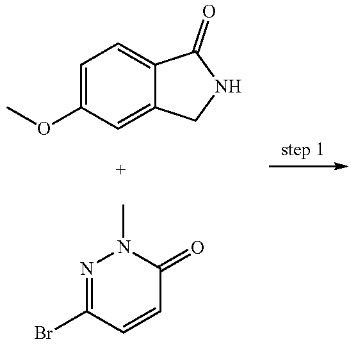

-continued

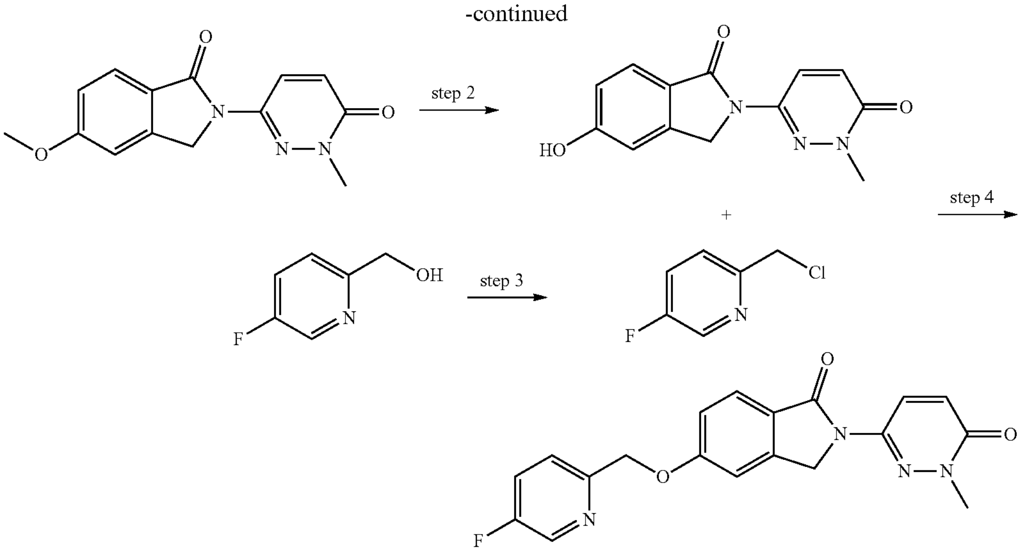

Example 1-1

Step 1: 5-Methoxy-2-(1-methyl-6-oxo-1,6-dihydro-pyridazin-3-yl)isoindolin-1-one

A mixture of 5-methoxy-2,3-dihydroisoindol-1-one (546 mg, 3.35 mmol), 6-bromo-2-methyl-3(2H)-pyridazinone (759 mg, 4.02 mmol), RuPhos (234 mg, 0.502 mmol), cesium carbonate (3.27 g, 10.0 mmol), and $Pd_2(dba)_3$ (153 mg, 0.167 mmol) in 1,4-dioxane (22.8 mL) was heated at 100° C. for 16 h. After this time, the reaction mixture was cooled, and water (50 mL) was added. The solid that formed was collected by filtration and dried in vacuo to give the title compound (691 mg, 76%). $^1H$ NMR (300 MHz, DMSO-$d_6$) 8.58 (d, J=10.2 Hz, 1H), 7.72 (d, J=8.4 Hz, 1H), 7.25 (d, J=1.8 Hz, 1H), 7.11-7.07 (m, 2H), 4.88 (s, 2H), 3.87 (s, 3H), 3.64 (s, 3H).

Step 2: 5-Hydroxy-2-(1-methyl-6-oxo-1,6-dihydro-pyridazin-3-yl)isoindolin-1-one 1.0 M Boron tribromide in DCM (27.6 mL, 27.6 mmol) was added to a solution of 5-methoxy-2-(1-methyl-6-oxo-1,6-dihydropyridazin-3-yl)isoindolin-1-one (691 mg, 2.55 mmol) in 1,2-dichloroethane (276 mL), and the mixture was stirred at reflux for 16 h. After this time, the mixture was cooled, and ice was added, followed by saturated aqueous sodium bicarbonate (30 mL). The solid that formed was collected by filtration and dried in vacuo, then was suspended in methanol (659 mL), and the mixture was stirred at reflux for 1 h. After this time, the solvent was removed in vacuo, water (100 mL) was added, and the mixture was sonicated for 10 min. The product was collected by filtration and dried in vacuo to give the title compound (540 mg, 82%). $^1H$ NMR (300 MHz, DMSO-$d_6$) 10.47 (br s, 1H), 8.58 (d, J=9.9 Hz, 1H), 7.62 (d, J=8.4 Hz, 1H), 7.07 (d, J=9.9 Hz, 1H), 7.00 (s, 1H), 6.91 (d, J=8.4 Hz, 1H), 4.83 (s, 2H), 3.63 (s, 3H).

Step 3: 2-(Chloromethyl)-5-fluoropyridine

Thionyl chloride (0.057 mL, 0.79 mmol) was added to a mixture of (5-fluoropyridin-2-yl)methanol (50 mg, 0.39 mmol) in DCM (2.7 mL), and the mixture was stirred at room temperature for 20 min. After this time, the mixture was poured into water (25 mL) and extracted with DCM (2×25 mL). The combined organic layers were dried over sodium sulfate, filtered, and concentrated in vacuo to give the title compound (57 mg, 99% yield), which was used in the next step without purification.

Step 4: 5-((5-Fluoropyridin-2-yl)methoxy)-2-(1-methyl-6-oxo-1,6-dihydropyridazin-3-yl)isoindolin-1-one A solution of 5-hydroxy-2-(1-methyl-6-oxo-1,6-dihydro-pyridazin-3-yl)isoindolin-1-one (50 mg, 0.19 mmol), 2-(chloromethyl)-5-fluoropyridine (50 mg, 0.34 mmol), and potassium carbonate (81 mg, 0.58 mmol) in DMSO (2 mL) was heated at 70° C. for 20 h. After this time, water (20 mL) was added, and the solid that formed was collected by filtration and triturated in MeOH (10 mL). This material was purified by FCC (silica, 0-5% MeOH in DCM), and the collected product was triturated in MeCN (10 mL) and lyophilized from 1:2 MeCN/water (10 mL) to give the title compound (28 mg, 39%).

Example 1-1: 5-((5-Fluoropyridin-2-yl)methoxy)-2-(1-methyl-6-oxo-1,6-dihydropyridazin-3-yl)isoindolin-1-one $^1H$ NMR (500 MHz, DMSO-$d_6$) 8.61 (d, J=3.0 Hz, 1H), 8.57 (d, J=10.0 Hz, 1H), 7.81 (td, J=8.5, 3.0 Hz, 1H), 7.73 (d, J=9.0 Hz, 1H), 7.66 (dd, J=9.0, 4.5 Hz, 1H), 7.35 (d, J=2.0 Hz, 1H), 7.19 (dd, J=8.5, 2.0 Hz, 1H), 7.08 (d, J=10.0 Hz, 1H), 5.30 (s, 2H), 4.88 (s, 2H), 3.64 (s, 3H). $^{19}F$ NMR (282 MHz, DMSO-$d_6$)-128.32. Tr(MET-uHPLC-001)=4.90 min, ($ES^+$) $(M+H)^+$ 367, 99%.

The following additional compounds were prepared by Method 1:

Example 1-2: 5-Methoxy-2-(pyridin-4-yl)-2,3-dihydro-1H-isoindol-1-one

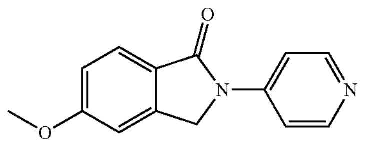 [SMILES: COc1ccc2c(c1)CN(c1ccncc1)C2=O]

$^1$H NMR (500 MHz, DMSO-$d_6$) 8.58-8.47 (m, 2H), 7.91-7.82 (m, 2H), 7.74 (d, J=8.5 Hz, 1H), 7.23 (d, J=1.9 Hz, 1H), 7.11 (dd, J=8.5, 2.3 Hz, 1H), 4.98 (s, 2H), 3.89 (s, 3H). Tr (MET-uHPLC-AB-101)=1.27 min, ($ES^+$) $(M+H)^+$ 241, 99%.

Example 1-3: 5-[(5-Iodopyridin-2-yl)methoxy]-2-(1-methyl-6-oxo-1,6-dihydropyridazin-3-yl)-2,3-dihydro-1H-isoindol-1-one

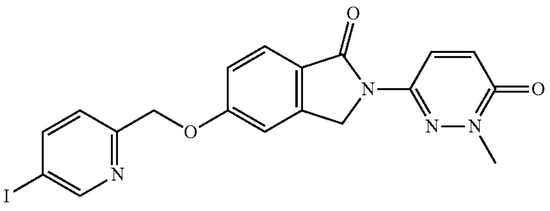

$^1$H NMR (500 MHz, DMSO-$d_6$) 8.83 (d, J=2.1 Hz, 1H), 8.57 (d, J=10.0 Hz, 1H), 8.24 (dd, J=8.2, 2.2 Hz, 1H), 7.73 (d, J=8.5 Hz, 1H), 7.41 (d, J=8.2 Hz, 1H), 7.33 (d, J=2.0 Hz, 1H), 7.18 (dd, J=8.5, 2.2 Hz, 1H), 7.08 (d, J=10.0 Hz, 1H), 5.26 (s, 2H), 4.87 (s, 2H), 3.63 (s, 3H). Tr(MET-uHPLC-AB-101)=3.12 min, (ES+) (M+H)+ 475, 98%.

Example 1-4 (Comparative Example 2): 5-[(5-Methoxypyridin-2-yl)methoxy]-2-(pyridin-4-yl)-2,3-dihydro-1H-isoindol-1-one

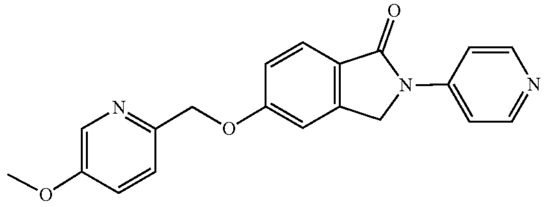 [SMILES: COc1ccc(COc2ccc3c(c2)CN(c2ccncc2)C3=O)nc1]

$^1$H NMR (500 MHz, DMSO-$d_6$) 8.56-8.48 (m, 2H), 8.31 (d, J=2.9 Hz, 1H), 7.90-7.85 (m, 2H), 7.74 (d, J=8.5 Hz, 1H), 7.52 (d, J=8.6 Hz, 1H), 7.44 (dd, J=8.6, 2.9 Hz, 1H), 7.31 (d, J=1.6 Hz, 1H), 7.19 (dd, J=8.5, 2.1 Hz, 1H), 5.24 (s, 2H), 4.97 (s, 2H), 3.84 (s, 3H). Tr(MET-uHPLC-AB-101)=1.59 min, ($ES^+$) $(M+H)^+$ 348, 99%.

Example 1-5: 5-Hydroxy-2-(1-methyl-6-oxo-1,6-dihydropyridazin-3-yl)-2,3-dihydro-1H-isoindol-1-one

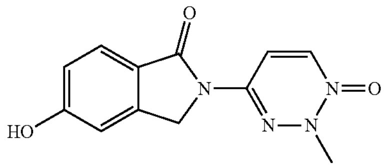

$^1$H NMR (500 MHz, DMSO-$d_6$) 10.46 (s, 1H), 8.58 (d, J=10.0 Hz, 1H), 7.62 (d, J=8.3 Hz, 1H), 7.07 (d, J=10.0 Hz, 1H), 7.01 (s, 1H), 6.91 (dd, J=8.3, 1.6 Hz, 1H), 4.83 (s, 2H), 3.63 (s, 3H). Tr(MET-uHPLC-AB-101)=1.66 min m/z (ES+) (M+H)+ 258.1, 96%.

Example 1-6: 5-[(5-Methoxypyridin-2-yl)methoxy]-2-(1-methyl-6-oxo-1,6-dihydropyridazin-3-yl)-2,3-dihydro-1H-isoindol-1-one

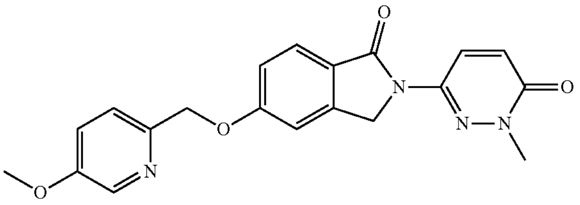 [SMILES: COc1ccc(COc2ccc3c(c2)CN(c2ccc(=O)n(C)n2)C3=O)nc1]

$^1$H NMR (500 MHz, DMSO-$d_6$) 8.57 (d, J=10.0 Hz, 1H), 8.30 (d, J=2.7 Hz, 1H), 7.72 (d, J=8.4 Hz, 1H), 7.51 (d, J=8.6 Hz, 1H), 7.44 (dd, J=8.6, 2.9 Hz, 1H), 7.34 (d, J=2.0 Hz, 1H), 7.17 (dd, J=8.4, 2.2 Hz, 1H), 7.08 (d, J=9.9 Hz, 1H), 5.22 (s, 2H), 4.87 (s, 2H), 3.84 (s, 3H), 3.63 (s, 3H). Tr(MET-HPLC-004)=11.42 min m/z (ES+) (M+H)+ 379.0, 99%.

Example 1-7: 5-[(3-Fluoro-5-methoxypyridin-2-yl)methoxy]-2-(1-methyl-6-oxo-1,6-dihydropyridazin-3-yl)-2,3-dihydro-1H-isoindol-1-one

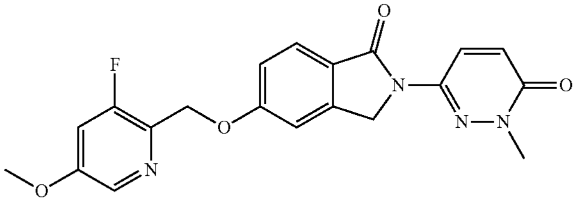 [SMILES: COc1cnc(COc2ccc3c(c2)CN(c2ccc(=O)n(C)n2)C3=O)c(F)c1]

$^1$H NMR (500 MHz, DMSO-$d_6$) 8.57 (d, J=10.0 Hz, 1H), 8.22 (d, J=2.5 Hz, 1H), 7.72 (d, J=8.5 Hz, 1H), 7.53 (dd, J=11.5, 2.5 Hz, 1H), 7.36 (d, J=2.0 Hz, 1H), 7.18 (dd, J=8.5, 2.5 Hz, 1H), 7.08 (d, J=10.0 Hz, 1H), 5.26 (d, J=1.5 Hz, 2H), 4.88 (s, 2H), 3.88 (s, 3H), 3.64 (s, 3H). $^{19}$F NMR (282 MHz, DMSO-$d_6$) −123.35. Tr(MET-uHPLC-001)=4.93 min m/z ($ES^+$) $(M+H)^+$ 397.2, 99%.

Example 1-8: 5-({5-[2-Fluoro(1,1,2,2-$^{2}H_4$)ethoxy]pyridin-2-yl}methoxy)-2-(1-methyl-6-oxo-1,6-dihydropyridazin-3-yl)-2,3-dihydro-1H-isoindol-1-one

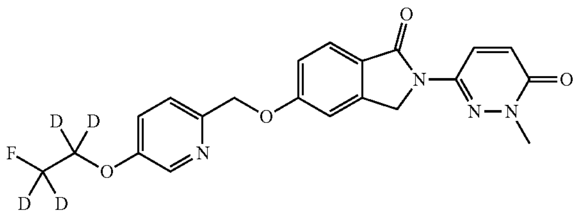 [SMILES: [2H]C([2H])(F)C([2H])([2H])Oc1ccc(COc2ccc3c(c2)CN(c2ccc(=O)n(C)n2)C3=O)nc1]

$^{1}$H NMR (500 MHz, DMSO-$d_6$) 8.57 (d, J=10.0 Hz, 1H), 8.34 (dd, J=3.0, 0.5 Hz, 1H), 7.72 (d, J=8.5 Hz, 1H), 7.52 (d, J=8.5 Hz, 1H), 7.48 (dd, J=8.5, 3.0 Hz, 1H), 7.34 (d, J=2.0 Hz, 1H), 7.18 (dd, J=8.5, 2.0 Hz, 1H), 7.08 (d, J=10.0 Hz, 1H), 5.23 (s, 2H), 4.88 (s, 2H), 3.64 (s, 3H). $^{19}$F NMR (282 MHz, DMSO-$d_6$) −224.24. Tr(MET-uHPLC-001)=3.85 min m/z (ES+) (M+H)+ 415.2, 98%.

Example 1-9: 2-{[6-({[2-(1-Methyl-6-oxo-1,6-dihydropyridazin-3-yl)-1-oxo-2,3-dihydro-1H-isoindol-5-yl]oxy}methyl)pyridin-3-yl]oxy}(1,1,2,2-$^{2}H_4$)ethyl 4-methylbenzene-1-sulfonate

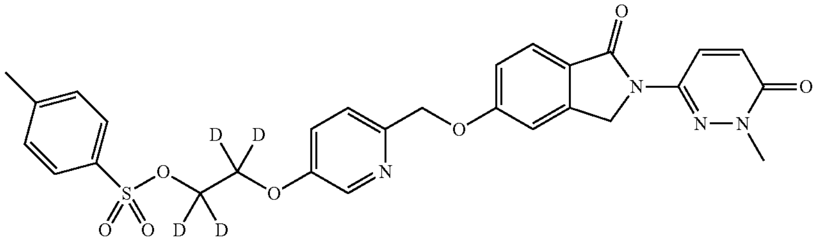 [SMILES: [2H]C([2H])(Oc1ccc(COc2ccc3c(c2)CN(c2ccc(=O)n(C)n2)C3=O)nc1)C([2H])([2H])OS(=O)(=O)c1ccc(C)cc1]

$^{1}$H NMR (500 MHz, DMSO-$d_6$) 8.57 (d, J=10.0 Hz, 1H), 8.19 (d, J=3.0 Hz, 1H), 7.79 (d, J=8.5 Hz, 2H), 7.72 (d, J=8.5 Hz, 1H), 7.49-7.45 (m, 3H), 7.37-7.33 (m, 2H), 7.17 (dd, J=8.5, 2.0 Hz, 1H), 7.07 (d, J=10.0 Hz, 1H), 5.21 (s, 2H), 4.88 (s, 2H), 3.64 (s, 3H), 2.41 (s, 3H). Tr(MET-uHPLC-001)=5.02 min m/z (ES+) (M+H)+ 567.2, 99%.

Example 1-10: 5-{[5-(1-Fluoroethoxy)pyridin-2-yl]methoxy}-2-(1-methyl-6-oxo-1,6-dihydropyridazin-3-yl)-2,3-dihydro-1H-isoindol-1-one

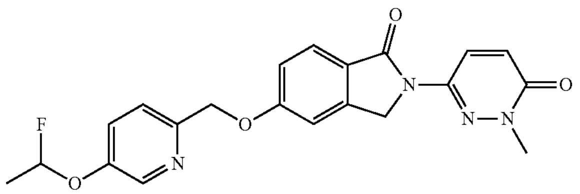 [SMILES: CC(F)Oc1ccc(COc2ccc3c(c2)CN(c2ccc(=O)n(C)n2)C3=O)nc1]

$^{1}$H NMR (500 MHz, DMSO-$d_6$) 8.57 (d, J=10.0 Hz, 1H), 8.41 (d, J=2.7 Hz, 1H), 7.73 (d, J=8.4 Hz, 1H), 7.62 (dd, J=8.3, 2.5 Hz, 1H), 7.58 (d, J=8.5 Hz, 1H), 7.34 (d, J=1.9 Hz, 1H), 7.18 (dd, J=8.5, 2.2 Hz, 1H), 7.08 (d, J=10.0 Hz, 1H), 6.31 (dq, J=62.2, 4.8 Hz, 1H), 5.26 (s, 2H), 4.88 (s, 2H), 3.63 (s, 3H), 1.62 (dd, J=20.5, 4.8 Hz, 3H). $^{19}$F NMR (282 MHz, DMSO-$d_6$) −117.10. Tr(MET-uHPLC-001)=3.34 min m/z (ES+) (M+H)+ 411.1, 99%.

Example 1-11: 5-[(4-Chloro-5-methoxypyridin-2-yl)methoxy]-2-(1-methyl-6-oxo-1,6-dihydropyridazin-3-yl)-2,3-dihydro-1H-isoindol-1-one

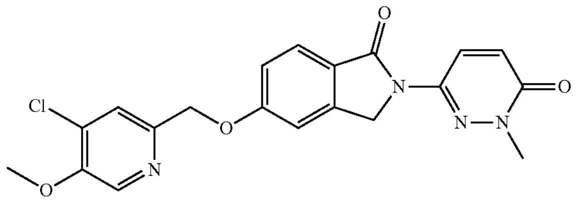

$^{1}$H NMR (500 MHz, $CDCl_3$) 8.74 (d, J=10.5 Hz, 1H), 8.27 (s, 1H), 7.82 (d, J=8.5 Hz, 1H), 7.55 (s, 1H), 7.12 (dd, J=8.5, 2.5 Hz, 1H), 7.07 (d, J=1.5 Hz, 1H), 7.01 (d, J=10.0 Hz, 1H), 5.21 (s, 2H), 4.85 (s, 2H), 4.03 (s, 3H), 3.76 (s, 3H). Tr(MET-uHPLC-001)=5.45 min m/z (ES+) (M+H)+ 413.1, 98%.

Example 1-12: 6-[(5-Methoxypyridin-2-yl)methoxy]-2-(1-methyl-6-oxo-1,6-dihydropyridazin-3-yl)-2,3-dihydro-1H-isoindol-1-one

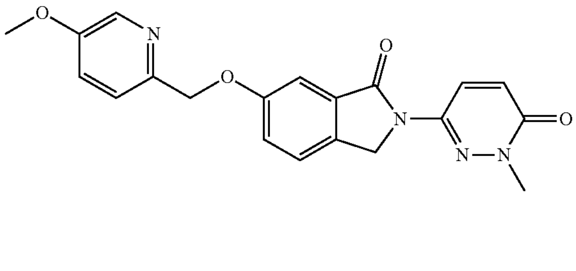 [SMILES: COc1ccc(COc2ccc3c(c2)C(=O)N(c2ccc(=O)n(C)n2)C3)nc1]

$^{1}$H NMR (500 MHz, DMSO-$d_6$) 8.56 (d, J=9.9 Hz, 1H), 8.30 (d, J=2.5 Hz, 1H), 7.60 (d, J=8.5 Hz, 1H), 7.49 (d, J=8.6 Hz, 1H), 7.43 (dd, J=8.5, 2.7 Hz, 1H), 7.36 (d, J=7.3 Hz, 2H), 7.09 (d, J=10.0 Hz, 1H), 5.21 (s, 2H), 4.86 (s, 2H), 3.83 (s, 3H), 3.64 (s, 3H). Tr(MET-uHPLC-001)=4.00 min m/z (ES+) (M+H)+ 379.2, 98%.

Example 1-13: 5-[(6-Fluoro-5-methoxy-2-pyridyl)methoxy]-2-(1-methyl-6-oxo-pyridazin-3-yl)isoindolin-1-one

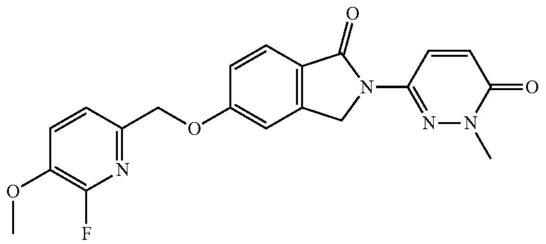 [SMILES: COc1ccc(COc2ccc3c(c2)CN(c2ccc(=O)n(C)n2)C3=O)nc1F]

$^1$H NMR (500 MHz, DMSO-$d_6$) 8.57 (d, J=10.0 Hz, 1H), 7.75-7.66 (m, 2H), 7.48 (d, J=8.1 Hz, 1H), 7.33 (d, J=1.9 Hz, 1H), 7.18 (dd, J=8.5, 2.3 Hz, 1H), 7.08 (d, J=10.0 Hz, 1H), 5.15 (s, 2H), 4.88 (s, 2H), 3.89 (s, 3H), 3.64 (s, 3H). $^{19}$F NMR (471 MHz, DMSO-$d_6$) −85.49 (d, J=10.5 Hz). Tr(MET-uHPLC-AB-101)=2.78 min m/z (ES+)(M+H)+ 397.2, 96%.

Example 1-14: 5-[(4-Fluoro-5-methoxypyridin-2-yl)methoxy]-2-(1-methyl-6-oxo-1,6-dihydropyridazin-3-yl)-2,3-dihydro-1H-isoindol-1-one

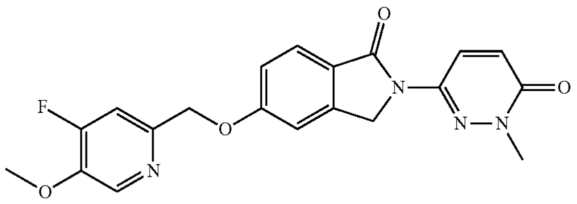 [SMILES: COc1cnc(COc2ccc3c(c2)CN(c2ccc(=O)n(C)n2)C3=O)cc1F]

$^1$H NMR (400 MHz, DMSO-$d_6$) 8.57 (d, J=9.3 Hz, 1H), 8.50 (d, J=9.8 Hz, 1H), 7.71 (d, J=7.6 Hz, 1H), 7.52 (d, J=10.2 Hz, 1H), 7.34 (s, 1H), 7.19 (d, J=6.2 Hz, 1H), 7.07 (d, J=10.1 Hz, 1H), 5.22 (s, 2H), 4.87 (s, 2H), 3.97 (s, 3H), 3.64 (s, 3H). $^{19}$F NMR (376 MHz, DMSO-$d_6$) −125.50. Tr(MET-uHPLC-AB-101)=2.64 min m/z (ES$^+$)(M+H)$^+$ 397.2, 97%.

Method 2

Scheme for Method 2

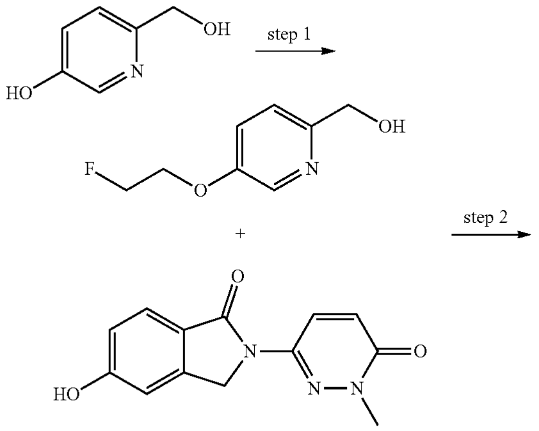

-continued

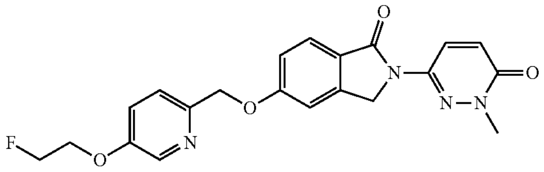

Example 2-1

Step 1: (5-(2-Fluoroethoxy)pyridin-2-yl)methanol

A mixture of 6-(hydroxymethyl)pyridin-3-ol (270 mg, 2.16 mmol) and potassium carbonate (447 mg, 3.23 mmol) in anhydrous MeCN (6 mL) was treated with 1-bromo-2-fluoroethane (0.32 mL, 4.3 mmol), and the resulting reaction mixture was heated at 70° C. for 24 h in a sealed tube. After this time, the reaction mixture was cooled to rt, diluted with water (50 mL), and extracted with EtOAc (3×50 mL). The organic layers were combined, dried over sodium sulfate, filtered, and the filtrate was concentrated under reduced pressure to afford the title compound (202 mg, 55%) as an orange-brown oil that was used in the next step without further purification. $^1$H NMR (300 MHz, DMSO-$d_6$) 8.22 (dd, J=2.7, 0.6 Hz, 1H), 7.45-7.37 (m, 2H), 5.32 (t, J=5.7 Hz, 1H), 4.85-4.82 (m, 1H), 4.69-4.66 (m, 1H), 4.49 (d, J=5.7 Hz, 2H), 4.37-4.34 (m, 1H), 4.27-4.24 (m, 1H). MS (ES$^+$) (M+H)$^+$ 172.

Step 2: 5-{[5-(2-Fluoroethoxy)pyridin-2-yl]methoxy}-2-(1-methyl-6-oxo-1,6-dihydropyridazin-3-yl)-2,3-dihydro-1H-isoindol-1-one To a mixture of 5-hydroxy-2-(1-methyl-6-oxo-1,6-dihydropyridazin-3-yl)isoindolin-1-one (80 mg, 0.31 mmol) and (5-(2-fluoroethoxy)pyridin-2-yl)methanol (106 mg, 0.622 mmol) in toluene (20 mL) was added CMBP (188 mg, 0.777 mmol). The mixture was heated at 120° C. in a sealed tube for 48 h. After this time, the solvent was removed under vacuum, and the residue obtained was purified by FCC (silica, 0-10% MeOH in DCM). The product was repurified by preparative HPLC (water-MeCN) to afford the title compound (31 mg, 24%).

Example 2-1: 5-{[5-(2-Fluoroethoxy)pyridin-2-yl]methoxy}-2-(1-methyl-6-oxo-1,6-dihydro-pyridazin-3-yl)-2,3-dihydro-1H-isoindol-1-one $^1$H NMR (500 MHz, DMSO-$d_6$) 8.58 (d, J=10.0 Hz, 1H), 8.34 (d, J=2.8 Hz, 1H), 7.72 (d, J=8.4 Hz, 1H), 7.52 (d, J=8.5 Hz, 1H), 7.49 (dd, J=8.6, 2.8 Hz, 1H), 7.34 (d, J=1.8 Hz, 1H), 7.18 (dd, J=8.4, 2.1 Hz, 1H), 7.08 (d, J=10.0 Hz, 1H), 5.23 (s, 2H), 4.87 (s, 2H), 4.82-4.71 (m, 2H), 4.38-4.31 (m, 2H), 3.63 (s, 3H). $^{19}$F NMR (282 MHz, DMSO-$d_6$) −222.34. Tr(MET-HPLC-005)=8.78 min, (ES$^+$) (M+H)$^+$411.1, 99%.

The following additional compounds were prepared by Method 2:

Example 2-2: 5-{[5-(Fluoromethoxy)pyridin-2-yl]methoxy}-2-(1-methyl-6-oxo-1,6-dihydropyridazin-3-yl)-2,3-dihydro-1H-isoindol-1-one

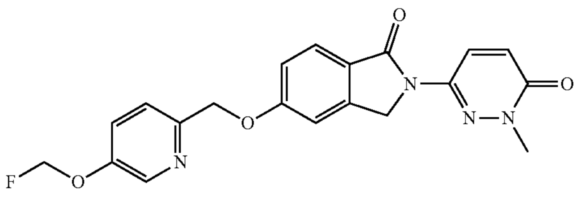 [SMILES: Cn1nc(N2Cc3cc(OCc4ccc(OCF)cn4)ccc3C2=O)ccc1=O]

$^1$H NMR (300 MHz, DMSO-$d_6$) 8.59 (d, J=10.0 Hz, 1H), 8.45 (d, J=2.7 Hz, 1H), 7.73 (d, J=8.5 Hz, 1H), 7.69-7.57 (m, 2H), 7.35 (d, J=1.9 Hz, 1H), 7.18 (dd, J=8.5, 2.3 Hz, 1H), 7.09 (d, J=10.0 Hz, 1H), 5.95 (d, J=53.7 Hz, 2H), 5.27 (s, 2H), 4.88 (s, 2H), 3.64 (s, 3H). $^{19}$F NMR (282 MHz, DMSO-$d_6$) −151.56. Tr(MET-uHPLC-001)=3.84 min, (ES+) (M+H)+ 397.3, 99%.

Example 2-3: 5-[(4-Chloro-5-fluoropyridin-2-yl)methoxy]-2-(1-methyl-6-oxo-1,6-dihydropyridazin-3-yl)-2,3-dihydro-1H-isoindol-1-one

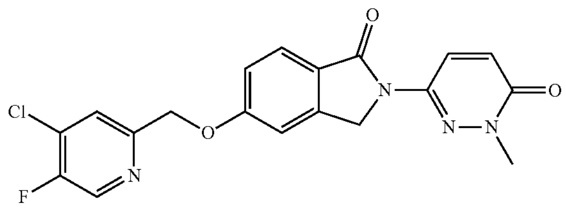 [SMILES: Cn1nc(N2Cc3cc(OCc4cc(Cl)c(F)cn4)ccc3C2=O)ccc1=O]

$^1$H NMR (500 MHz, DMSO-$d_6$) 8.75 (d, J=1.0 Hz, 1H), 8.57 (d, J=9.5 Hz, 1H), 7.90 (d, J=6.0 Hz, 1H), 7.74 (d, J=8.5 Hz, 1H), 7.36 (d, J=2.5 Hz, 1H), 7.22 (dd, J=8.5, 2.5 Hz, 1H), 7.07 (d, J=10.0 Hz, 1H), 5.29 (s, 2H), 4.88 (s, 2H), 3.64 (s, 3H). $^{19}$F NMR (282 MHz, DMSO-$d_6$) −132.59. Tr(MET-uHPLC-001)=5.65 min m/z (ES+) (M+H)+ 401.1, 98%.

Method 3

Scheme for Method 3

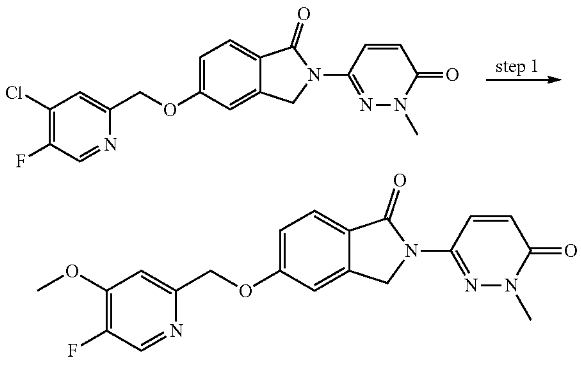

Example 3-1

Step 1: 5-[(5-Fluoro-4-methoxypyridin-2-yl)methoxy]-2-(1-methyl-6-oxo-1,6-dihydropyridazin-3-yl)-2,3-dihydro-1H-isoindol-1-one To a solution of 5-((4-chloro-5-fluoropyridin-2-yl)methoxy)-2-(1-methyl-6-oxo-1,6-dihydropyridazin-3-yl)isoindolin-1-one (68 mg, 0.16 mmol) in MeOH (2.0 mL) and THF (2.0 mL) was added a 25 wt % solution of sodium methoxide in MeOH (0.041 mL, 0.18 mmol), and the reaction mixture was heated at 65° C. for 16 h. After this time, the solvent was removed under reduced pressure, and the residue obtained was triturated in water and purified twice by FCC (silica, 0-15% MeOH in EtOAc). The collected material was purified again by FCC (silica, 0-10% MeOH in DCM) and recrystallized from MeCN to afford the title compound (23 mg, 35%).

Example 3-1: 5-[(5-Fluoro-4-methoxypyridin-2-yl)methoxy]-2-(1-methyl-6-oxo-1,6-di-hydropyridazin-3-yl)-2,3-dihydro-1H-isoindol-1-one $^1$H NMR (500 MHz, DMSO-$d_6$) 8.57 (d, J=10.0 Hz, 1H), 8.44 (d, J=3.0 Hz, 1H), 7.73 (d, J=8.5 Hz, 1H), 7.44 (d, J=7.0 Hz, 1H), 7.36 (d, J=2.0 Hz, 1H), 7.21 (dd, J=8.5, 2.0 Hz, 1H), 7.07 (d, J=10.0 Hz, 1H), 5.22 (s, 2H), 4.89 (s, 2H), 3.96 (s, 3H), 3.64 (s, 3H). $^{19}$F NMR (282 MHz, DMSO-$d_6$) −152.71. Tr(MET-uHPLC-001)=4.42 min, (ES$^+$) (M+H)$^+$ 397.0, 99%.

Method 4

Scheme for Method 4

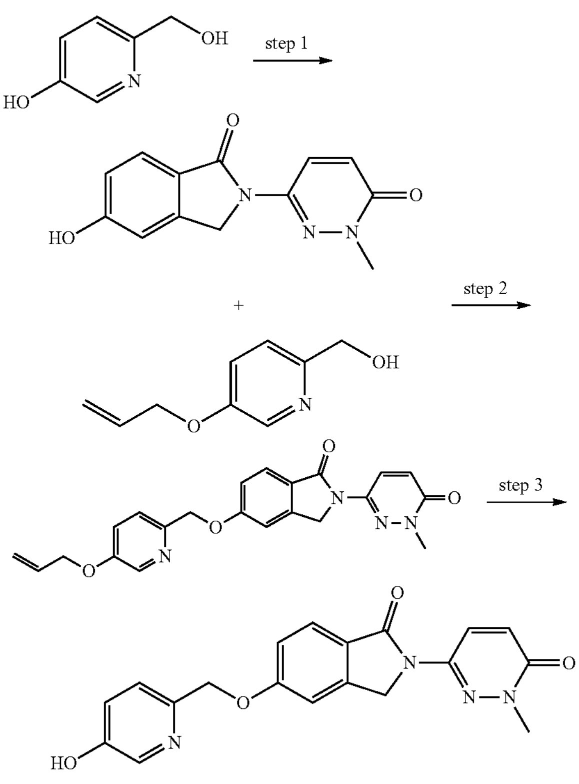

Example 4-1

Step 1: (5-(Allyloxy)pyridin-2-yl)methanol

A solution of potassium carbonate (1.65 g, 11.9 mmol) in water (4 mL) was added dropwise over 15 min to a mixture of 6-(hydroxymethyl)pyridin-3-ol (1.00 g, 7.99 mmol) and allyl bromide (0.80 mL, 9.3 mmol) in acetone (10 mL), and the reaction mixture was heated at 60° C. for 2 h in a sealed tube. After this time, the mixture was cooled to room temperature and extracted with MTBE (3×100 mL). The organic layers were combined, dried over sodium sulfate, filtered, and the filtrate concentrated under reduced pressure to afford the title compound (713 mg, 54%) as a red-brown oil that was used in the next step without further purification. $^1$H NMR (500 MHz, DMSO-$d_6$) 8.19 (dd, J=2.5, 0.5 Hz, 1H), 7.49-7.35 (m, 2H), 6.07-5.99 (m, 1H), 5.40 (dq, J=17.5, 1.5 Hz, 1H), 5.29-5.25 (m, 2H), 4.63 (dt, J=5.0, 1.5 Hz, 2H), 4.48 (d, J=5.5 Hz, 2H).

Step 2: 5-((5-(Allyloxy)pyridin-2-yl)methoxy)-2-(1-methyl-6-oxo-1,6-dihydropyridazin-3-yl)isoindo-lin-1-one CMBP (586 mg, 2.43 mmol) was added to a solution of 5-hydroxy-2-(1-methyl-6-oxo-1,6-dihydropyridazin-3-yl) isoindolin-1-one (250 mg, 0.972 mmol) and (5-(allyloxy) pyridin-2-yl)methanol (321 mg, 1.94 mmol) in toluene (36.0 mL), and the solution was heated at 120° C. for 3 d. After this time, the solvent was removed in vacuo. The residue obtained was suspended in DCM (5 mL) and heptane (5 mL) and filtered. The filter cake was washed with heptane (5 mL), and the filtrate was concentrated in vacuo. The residue obtained was purified by FCC (silica, 0-5% MeOH in DCM). The product obtained was triturated with heptane (5 mL), collected by filtration, and washed with heptane (5 mL) to afford the title compound (45 mg, 12%) as a tan solid. $^1$H NMR (300 MHz, DMSO-$d_6$) 8.58 (d, J=9.9 Hz, 1H), 8.32 (d, J=2.4 Hz, 1H), 7.72 (d, J=8.4 Hz, 1H), 7.51 (d, J=8.7 Hz, 1H), 7.45 (dd, J=8.4, 2.7 Hz, 1H), 7.34 (d, J=1.8 Hz, 1H), 7.18 (dd, J=8.4, 2.1 Hz, 1H), 7.09 (d, J=10.2 Hz, 1H), 6.11-5.99 (m, 1H), 5.42 (dq, J=17.1, 1.5, Hz, 1H), 5.29 (dd, J=10.5, 1.5 Hz, 1H), 5.22 (s, 2H), 4.88 (s, 2H), 4.67 (dt, J=5.1, 1.2 Hz, 2H), 3.64 (s, 3H).

Step 3: 5-[(5-Hydroxypyridin-2-yl)methoxy]-2-(1-methyl-6-oxo-1,6-dihydropyridazin-3-yl)-2,3-di-hydro-1H-isoindol-1-one 1,3-Dimethylbarbituric acid (57 mg, 0.37 mmol) and tetrakis(triphenylphosphine)palladium(O) (10.5 mg, 0.00915 mmol) were added to a solution of 5-((5-(allyloxy)-pyridin-2-yl)methoxy)-2-(1-methyl-6-oxo-1,6-dihydro-pyridazin-3-yl)isoindolin-1-one (74 mg, 0.18 mmol) in MeOH (6.6 mL), and the mixture was stirred at rt for 16 h. After this time, the solvent was removed in vacuo, and DCM (20 mL) was added. The mixture was washed with sat. aq sodium bicarbonate (20 mL), the layers were separated, and the aqueous layer was extracted with DCM (2×30 mL). The combined organic layers were dried over sodium sulfate, filtered, and the filtrate was concentrated in vacuo. The residue obtained was purified by FCC (silica, 0-5% MeOH in DCM), and the product was lyophilized from MeCN (10 mL) and water (10 mL) to afford the title compound (41 mg, 46%).

Example 4-1: 5-[(5-Hydroxypyridin-2-yl)methoxy]-2-(1-methyl-6-oxo-1,6-dihydropyridazin-3-yl)-2,3-dihydro-1H-isoindol-1-one $^1$H NMR (500 MHz, DMSO-$d_6$) 10.01 (br s, 1H), 8.57 (d, J=10.0 Hz, 1H), 8.14 (d, J=3.0 Hz, 1H), 7.71 (d, J=8.5 Hz, 1H), 7.39 (d, J=8.5 Hz, 1H), 7.33 (d, J=2.0 Hz, 1H), 7.20 (dd, J=8.5, 3.0 Hz, 1H), 7.16 (dd, J=8.0, 2.0 Hz, 1H), 7.08 (d, J=10.0 Hz, 1H), 5.16 (s, 2H), 4.87 (s, 2H), 3.64 (s, 3H). Tr(MET-HPLC-003)=10.48 min, ($ES^+$) $(M+H)^+$ 365.2, 99%.

Method 5

Scheme for Method 5

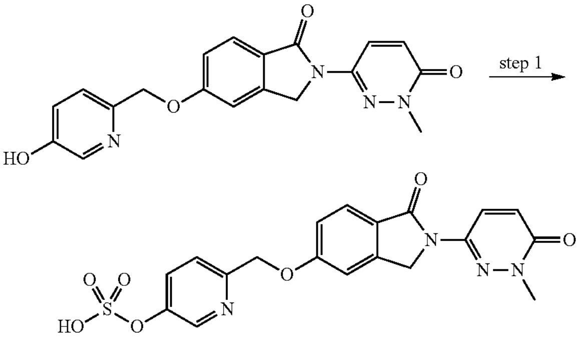

Example 5-1

Step 1: [6-({[2-(1-Methyl-6-oxo-1,6-dihydro-pyridazin-3-yl)-1-oxo-2,3-dihydro-1H-isoindol-5-yl] oxy}methyl)pyridin-3-yl]oxidanesulfonic acid Chlorosulfonic acid (0.091 mL, 1.4 mmol) was added to a mixture of 5-((5-hydroxypyridin-2-yl)methoxy)-2-(1-methyl-6-oxo-1,6-dihydropyridazin-3-yl)isoindolin-1-one (50 mg, 0.14 mmol) in pyridine (6.3 mL) at −15° C. After complete addition, the mixture was allowed to warm to rt and stir for 2 d. After this time, the solvent was removed in vacuo, and water (5.0 mL) was added. The mixture was allowed to age for 2.5 d. After this time, the solid that formed was collected by filtration, washed with water (5.0 mL), and dried in vacuo. The dried solid was triturated with DCM (7.9 mL) and then purified by reverse phase chromatography (MPLC, water-MeCN). The product obtained was lyophilized, and then triturated with water (15.0 mL) for 2 h, collected by filtration, and dried under vacuum to afford the title compound (27 mg, 44%).

Example 5-1: [6-({[2-(1-Methyl-6-oxo-1,6-dihydro-pyridazin-3-yl)-1-oxo-2,3-dihydro-1H-isoindol-5-yl] oxy}methyl)pyridin-3-yl]oxidanesulfonic acid $^1$H NMR (300 MHz, DMSO-$d_6$) 8.58 (d, J=9.9 Hz, 1H), 8.44 (d, J=2.4 Hz, 1H), 7.79-7.72 (m, 2H), 7.59 (d, J=8.7 Hz, 1H), 7.36 (s, 1H), 7.20 (dd, J=8.7, 2.1 Hz, 1H), 7.08 (d, J=10.2 Hz, 1H), 5.29 (s, 2H), 4.87 (s, 2H), 3.64 (s, 3H). Tr(MET-uHPLC-001)=2.90 min, ($ES^-$) $(M-H)^-$ 443.3, 98%.

Method 6

Scheme for Method 6

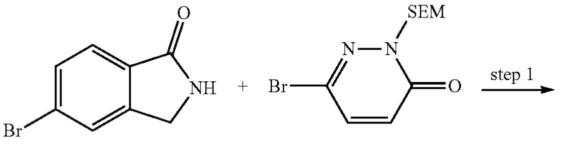

-continued

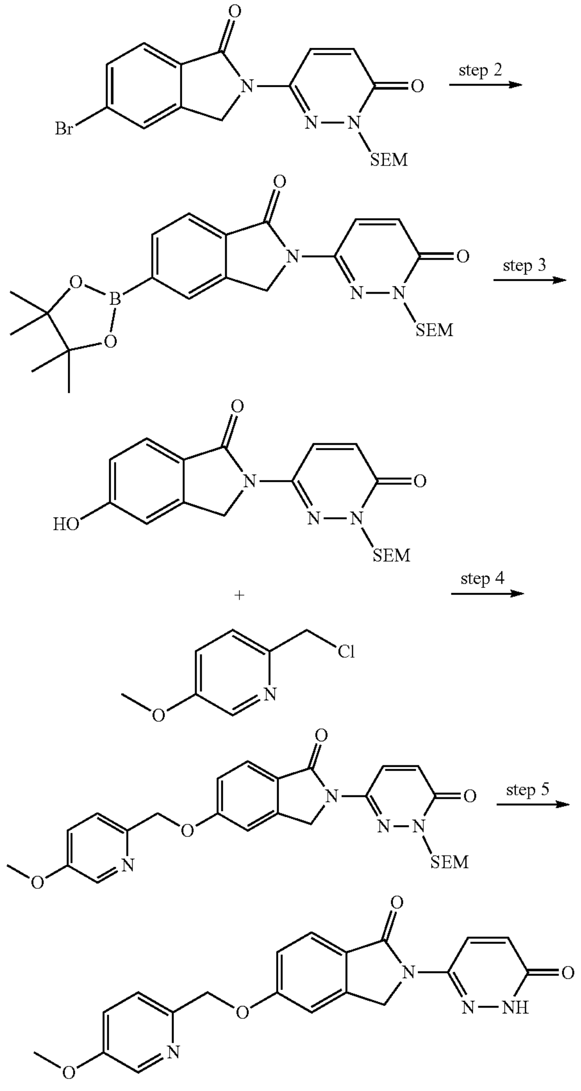

Example 6-1

Step 1: 5-Bromo-2-(6-oxo-1-((2-(trlinethylsilypethoxy)methyl)-1,6-dihydropyridazin-3-yl)isoindolin-1-one In a sealed tube, a mixture of 5-bromoisoindolin-1-one (700 mg, 3.30 mmol), 6-bromo-2-((2-(trimethylsilyl)ethoxy)methyl)pyridazin-3(2H)-one (1.21 g, 3.96 mmol), RuPhos (231 mg, 0.495 mmol), cesium carbonate (3.23 g, 9.90 mmol), and $Pd_2(dba)_3$ (151 mg, 0.165 mmol) in 1,4-dioxane (16.9 mL) was heated at 100° C. for 16 h under nitrogen. After this time, the reaction mixture was combined with other batches, diluted with water (250 mL), and extracted with EtOAc (3×250 mL). The combined organic layers were washed with brine, dried over sodium sulfate, filtered, and concentrated under reduced pressure. The residue obtained was purified by FCC (silica, 0-40% EtOAc in DCM) to afford the title compound (1.438 g, >99%). $^1$H NMR (300 MHz, DMSO-$d_6$) 8.62 (d, J=9.9 Hz, 1H), 8.01 (s, 1H), 7.78-7.77 (m, 2H), 7.17 (d, J=9.9 Hz, 1H), 5.35 (s, 2H), 4.95 (s, 2H), 3.72 (t, J=8.1 Hz, 2H), 0.91 (t, J=8.1 Hz, 2H), 0.02 (s, 9H); MS (ES$^+$) (M+H)$^+$ 437.

Step 2: 2-(6-Oxo-1-((2-(trlinethylsilypethoxy)methyl)-1,6-dihydropyridazin-3-yl)-5-(4,4,5,5-tetramethyl-1,3,2-dioxaborolan-2-yl)isoindolin-1-one $Pd(dppf)Cl_2$ (134 mg, 0.165 mmol) was added to a mixture of 5-bromo-2-(6-((2-(trimethylsilyl)ethoxy)methoxy)pyridazin-3-yl)isoindolin-1-one (718 mg, 1.65 mmol), bis(pinacolato)diboron (627 mg, 2.47 mmol), potassium acetate (404 mg, 4.11 mmol), and 1,4-dioxane (14 mL) in a microwave vial. The suspension was sparged with argon, and the vial was sealed and heated at 90° C. for 2 h. After this time, the reaction mixture was combined with another batch and concentrated under reduced pressure. The residue obtained was partitioned between EtOAc (100 mL) and water (100 mL). The layers were separated, and the aqueous layer was extracted with EtOAc (2×100 mL). The combined organic layers were dried over sodium sulfate, filtered, and concentrated to afford the title compound (2.947 g) which was used in the next step without purification.

Step 3: 5-Hydroxy-2-(6-oxo-1-((2-(trlinethylsilypethoxy)methyl)-1,6-dihydropyridazin-3-yl)iso-indolin-1-one A suspension of sodium perborate tetrahydrate (1.27 g, 8.23 mmol) in water (21 mL) was added to a suspension of crude 2-(6-oxo-1-((2-(trimethylsilyl)ethoxy)methyl)-1,6-dihydropyridazin-3-yl)-5-(4,4,5,5-tetramethyl-1,3,2-dioxaborolan-2-yl)isoindolin-1-one (est. 3.29 mmol) in THF (41 mL). The reaction mixture was stirred at room temperature for 16 h. After this time, aq sat ammonium chloride (75 mL) was added, and the mixture was concentrated under reduced pressure. The residue obtained was diluted with MeOH, and the pH was adjusted to 3 with 2 N HCl. The MeOH was removed under reduced pressure, and the residue obtained was suspended in water and aged at room temperature for 16 h. The resulting solids were collected by filtration, rinsed with water, and dried. The material was purified by FCC (silica, 0-40% EtOAc in DCM, then 0-10% MeOH in DCM) to afford the title compound (499 mg, 40%). $^1$H NMR (300 MHz, DMSO-$d_6$) 10.49 (s, 1H), 8.61 (d, J=10.2 Hz, 1H), 7.63 (d, J=8.4 Hz, 1H), 7.11 (d, J=10.2 Hz, 1H), 7.01 (s, 1H), 6.91 (dd, J=8.4, 2.1 Hz, 1H), 5.31 (s, 2H), 4.82 (s, 2H), 3.70 (t, J=7.8 Hz, 2H), 0.89 (t, J=8.1 Hz, 2H), 0.01 (s, 9H). MS (ES$^+$) (M+H)$^+$ 374.

Step 4: 5-((5-Methoxypyridin-2-yl)methoxy)-2-(6-oxo-1-((2-(trimethylsilyl)ethoxy)methyl)-1,6-dihydropyridazin-3-yl)isoindolin-1-one Potassium carbonate (554 mg, 4.01 mmol) was added to a mixture of 5-hydroxy-2-(6-oxo-1-((2-(trimethylsilyl)ethoxy)methyl)-1,6-dihydropyridazin-3-yl)isoindolin-1-one (499 mg, 1.34 mmol) and 2-(chloromethyl)-5-methoxypyridine (253 mg, 1.60 mmol) in DMF (17 mL), and the mixture was heated at 70° C. for 1 h. After this time, the solvent was removed under reduced pressure, and the residue obtained was dissolved in 80:20 DCM/MeOH, and filtered. The filtrate was concentrated under reduced pressure, and the crude product mixture was purified by FCC (silica, 20-80% EtOAc in DCM, then 0-20% MeOH in DCM) to afford the title compound (494 mg, 75%). $^1$H NMR (300 MHz, DMSO-$d_6$) 8.63 (d, J=10.2 Hz, 1H), 8.33 (d, J=2.7 Hz, 1H), 7.75 (d, J=8.4 Hz, 1H), 7.54 (d, J=8.7 Hz, 1H), 7.46 (dd, J=8.4, 2.7 Hz, 1H), 7.37 (s, 1H), 7.20 (dd, J=8.4, 1.8 Hz, 1H), 7.14 (d, J=9.9 Hz, 1H), 5.34 (s, 2H), 5.24 (s, 2H), 4.89

(s, 2H), 3.86 (s, 3H), 3.72 (t, J=7.8 Hz, 2H), 0.91 (t, J=8.1 Hz, 2H), 0.02 (s, 9H). MS ($ES^+$) $(M+H)^+$ 495.

Step 5: 5-[(5-Methoxypyridin-2-yl)methoxy]-2-(6-oxo-1,6-dihydropyridazin-3-yl)-2,3-dihydro-1H-isoindol-1-one TFA (1.9 mL) was added to a solution of 5-((5-methoxypyridin-2-yl)methoxy)-2-(6-((2-(trimethyl-silyl)ethoxy)methoxy)pyridazin-3-yl)isoindolin-1-one (494 mg, 0.999 mmol) in DCM (5.7 mL), and the mixture was stirred at room temperature for 2 h. After this time, heptane (73 mL) was added, and the volatiles were removed under reduced pressure. The residue obtained was solvent exchanged with EtOAc (14 mL) and heptane (73 mL), and the residue was triturated in 50:50 water/MeOH (145 mL) for 1 h at rt. The mixture was left to age over 3 days, and the solid was collected by filtration, and washed with water (28 mL), MeOH (14 mL), and heptane (27 mL). The resulting solid was purified by FCC (silica, 0-20% MeOH in EtOAc, then 0-20% MeOH in DCM). The product obtained was combined with previous batches and purified by reverse phase chromatography (MPLC, MeCN-water, 0.1% v/v TFA). The clean fractions obtained were poured into sat. sodium bicarbonate. The pH of the solution was adjusted to 6 with 2 N HCl, and the resulting precipitate was collected by filtration, and washed with water and MeCN to afford the title compound (264 mg).

Example 6-1: 5-[(5-Methoxypyridin-2-yl)methoxy]-2-(6-oxo-1,6-dihydropyridazin-3-yl)-2,3-dihydro-1H-isoindol-1-one $^1H$ NMR (500 MHz, DMSO-$d_6$) 12.77 (s, 1H), 8.56 (d, J=10.5 Hz, 1H), 8.30 (d, J=3.0 Hz, 1H), 7.71 (d, J=8.5 Hz, 1H), 7.51 (d, J=8.5 Hz, 1H), 7.44 (dd, J=9.0, 3.0 Hz, 1H), 7.33 (d, J=2.0 Hz, 1H), 7.17 (dd, J=8.5, 2.0 Hz, 1H), 7.01 (d, J=10.5 Hz, 1H), 5.22 (s, 2H), 4.86 (s, 2H), 3.84 (s, 3H). Tr(MET-uHPLC-001)=3.36 min, ($ES^+$) $(M+H)^+$ 365.1, 100%.

Method 7

Scheme for Method 7

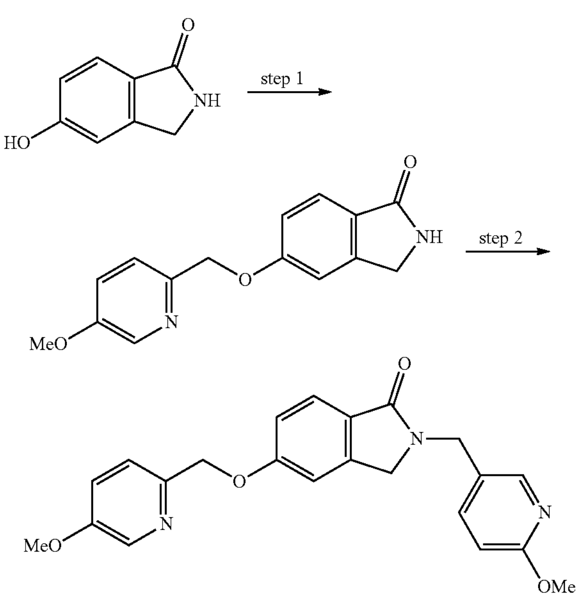

Step 1: 5-[(5-Methoxy-2-pyridyl)methoxy]isoindolin-1-one (5-Methoxypyridin-2-yl)methanol (100 mg, 0.719 mmol) was dissolved in DCM (2 mL). Thionyl chloride (0.104 mL, 1.44 mmol) was added and the reaction mixture was stirred under $N_2$ for 1 h. The reaction mixture was concentrated in vacuo and the residue was co-distilled with DCM (3×10 mL) and concentrated in vacuo to give 2-(chloromethyl)-5-methoxy-pyridine which was used without further purification.

5-Hydroxyisoindolin-1-one (100 mg, 0.670 mmol), KI (111 mg, 0.670 mmol), and $Cs_2CO_3$ (0.107 mL, 1.34 mmol) were dissolved in DMF (6 mL), and the reaction mixture was stirred at room temperature for 10 min. 2-(Chloromethyl)-5-methoxy-pyridine (116 mg, 0.738 mmol) was added, and the reaction mixture was stirred at room temperature overnight. DMF was removed in vacuo and the residue was triturated with $H_2O$ (10 mL) and with EtOH (10 mL) to give the title compound (140 mg, 77% yield). $^1H$ NMR (500 MHz, DMSO-$d_6$) 8.29 (d, J=2.8 Hz, 2H), 7.56 (d, J=8.4 Hz, 1H), 7.49 (d, J=8.6 Hz, 1H), 7.43 (dd, J=8.6, 2.9 Hz, 1H), 7.20 (d, J=1.9 Hz, 1H), 7.09 (dd, J=8.4, 2.2 Hz, 1H), 5.18 (s, 2H), 4.30 (s, 2H), 3.84 (s, 3H). Tr(METCR1600)=3.07 min, ($ES^+$) $(M+H)^+$ 271.1, 100%.

Step 2: 5-[(5-Methoxy-2-pyridyl)methoxy]-2-[(6-methoxy-3-pyridyl)methyl]isoindolin-1-one NaH (60% in oil, 41 mg, 1.04 mmol) and THF (6 mL) were added to a solution of 5-[(5-methoxy-2-pyridyl)methoxy]isoindolin-1-one (140 mg, 0.518 mmol), and the reaction mixture was heated to 70° C. under reflux for 1 h. The reaction mixture was then cooled to room temperature and 5-(chloromethyl)-2-methoxy-pyridine (prepared as for step 1) (98 mg, 0.622 mmol) in 2:1 THF:DMF (6 mL) was added. The reaction mixture was stirred overnight at room temperature. Additional NaH (60% in oil, 41 mg, 1.036 mmol) was added to the reaction mixture which was then heated under reflux for 30 min. The reaction mixture was cooled to room temperature, 5-(chloromethyl)-2-methoxy-pyridine (98 mg, 0.622 mmol) was added and the reaction mixture stirred for 3 days. The mixture was diluted with EtOAc (25 mL) and washed with $H_2O$ (2×15 mL). The combined organic layers were dried over $Na_2SO_4$, filtered, and concentrated. The crude product was purified by preparative HPLC (MeCN-Water, 2 mM $NH_4HCO_3$) to give the title compound (11.5 mg, 5%).

Example 7-1

5-[(5-Methoxypyridin-2-yl)methoxy]-2-[(6-methoxypyridin-3-yl)methyl]-2,3-dihydro-1H-isoindol-1-one $^1H$ NMR (500 MHz, DMSO-$d_6$) 8.28 (d, J=2.9 Hz, 1H), 8.12 (d, J=2.3 Hz, 1H), 7.63-7.58 (m, 2H), 7.47 (d, J=8.6 Hz, 1H), 7.42 (dd, J=8.6, 2.9 Hz, 1H), 7.19 (d, J=2.0 Hz, 1H), 7.11 (dd, J=8.4, 2.2 Hz, 1H), 6.79 (d, J=8.5 Hz, 1H), 5.16 (s, 2H), 4.63 (s, 2H), 4.30 (s, 2H), 3.83 (s, 3H), 3.83 (s, 3H). Tr(MET-uHPLC-AB-101)=2.49 min, ($ES^+$) $(M+H)^+$ 392, 96%.

Method 8

Scheme for Method 8

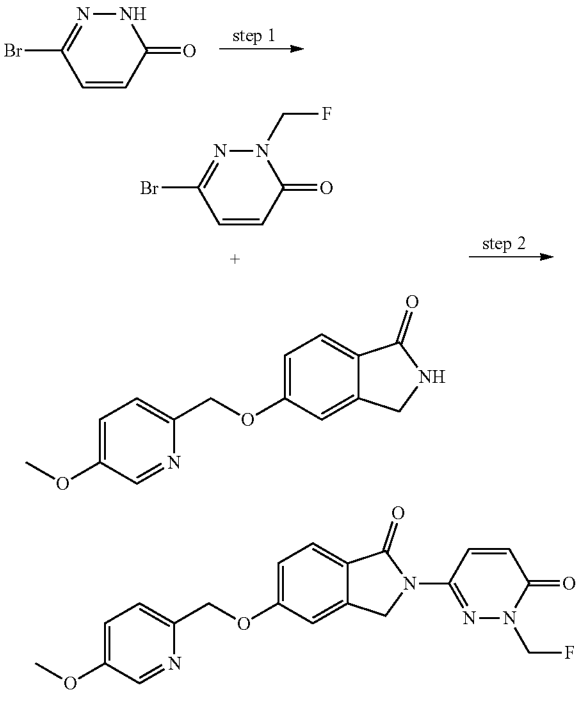

Example 8-1

Step 1: 6-Bromo-2-(fluoromethyl)pyridazin-3(2H)-one

To a solution of 6-bromopyridazin-3(2H)-one (150 mg, 0.857 mmol) in 1,4-dioxane (5 mL) in a reaction vial, was added potassium carbonate (237 mg, 1.71 mmol) followed by DMF (3 mL). The reaction vial was sealed, and a cold solution of bromofluoromethane (2.0 M in MeCN, 0.69 mL, 1.4 mmol) was added. The mixture was heated at 150° C. for 1.5 h. After this time, the mixture was cooled to rt and concentrated to dryness under reduced pressure. The residue obtained was adsorbed onto silica gel and purified by FCC (silica, 0-50% EtOAc in hexanes) to afford the title compound (90 mg, 51%). $^{1}$H NMR (300 MHz, $CDCl_3$) 7.30 (d, J=9.6 Hz, 1H), 6.87 (d, J=9.6 Hz, 1H), 5.98 (d, J=50.7 Hz, 2H). $^{19}$F NMR (282 MHz, $CDCl_3$) −176.17. MS (ES+) (M+H)+ 207.0.

Step 2: 2-(1-(Fluoromethyl)-6-oxo-1,6-dihydropyridazin-3-yl)-5-((5-methoxypyridin-2-yl)methoxy)-isoindolin-1-one A mixture of 5-((5-methoxypyridin-2-yl)methoxy)isoindolin-1-one (35 mg, 0.13 mmol), 6-bromo-2-(fluoromethyl)pyridazin-3(2H)-one (32 mg, 0.16 mmol), RuPhos (9 mg, 0.02 mmol), and cesium carbonate (127 mg, 0.390 mmol) in 1,4-dioxane (2 mL) was purged with nitrogen for 2 min, and $Pd_2(dba)_3$ (6.70 mg, 0.00732 mmol) was added. The reaction vial was sealed and heated at 110° C. for 4 h. After this time, the reaction mixture was concentrated to dryness, and the residue obtained was purified by FCC (silica, 0-40% MeOH in EtOAc). The product was triturated in ethyl acetate, and the solids were collected by filtration and dried under vacuum at 50° C. for 3 h to afford the title compound (46 mg, 90%).

Example 8-1: 2-(1-(Fluoromethyl)-6-oxo-1,6-dihydropyridazin-3-yl)-5-((5-methoxypyridin-2-yl)methoxy)isoindolin-1-one $^{1}$H NMR (500 MHz, DMSO-$d_6$) 8.68 (d, J=10.0 Hz, 1H), 8.31 (d, J=2.5 Hz, 1H), 7.74 (d, J=8.5 Hz, 1H), 7.52 (d, J=8.5 Hz, 1H), 7.44 (dd, J=9.0, 3.0 Hz, 1H), 7.35 (d, J=2.0 Hz, 1H), 7.19-7.17 (m, 2H), 5.98 (d, J=51.5 Hz, 2H), 5.22 (s, 2H), 4.88 (s, 2H), 3.84 (s, 3H). $^{19}$F NMR (282 MHz, DMSO-$d_6$) −174.59. Tr(MET-uHPLC-001)=2.81 min, ($ES^+$) $(M+H)^+$ 397.0, 100%.

The following additional compounds were prepared by Method 8:

Example 8-2: 2-[1-(2-Fluoroethyl)-6-oxo-1,6-dihydropyridazin-3-yl]-5-[(5-methoxypyridin-2-yl)methoxy]-2,3-dihydro-1H-isoindol-1-one

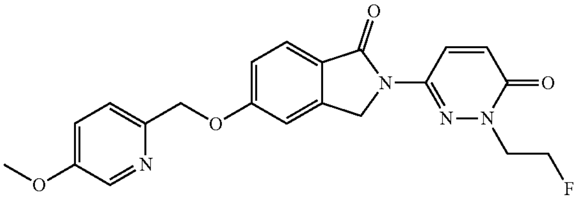 [SMILES: COc1ccc(COc2ccc3c(c2)CN(c2ccc(=O)n(CCF)n2)C3=O)nc1]

$^{1}$H NMR (500 MHz, DMSO-$d_6$) 8.59 (d, J=10.0 Hz, 1H), 8.31 (d, J=3.0 Hz, 1H), 7.73 (d, J=8.5 Hz, 1H), 7.52 (d, J=8.5 Hz, 1H), 7.44 (dd, J=8.5, 3.0 Hz, 1H), 7.34 (d, J=2.0 Hz, 1H), 7.18 (dd, J=8.5, 2.0 Hz, 1H), 7.11 (d, J=10.0 Hz, 1H), 5.22 (s, 2H), 4.89 (s, 2H), 4.82 (dt, J=47.0, 5.0 Hz, 2H), 4.35 (dt, J=26.5, 5.0 Hz, 2H), 3.84 (s, 3H). $^{19}$F NMR (282 MHz, DMSO-$d_6$) −224.07. Tr(MET-uHPLC-001)=2.75 min m/z ($ES^+$) $(M+H)^+$ 411.1, 100%.

Method 9

Scheme for Method 9

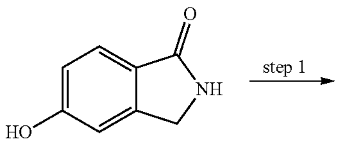

-continued

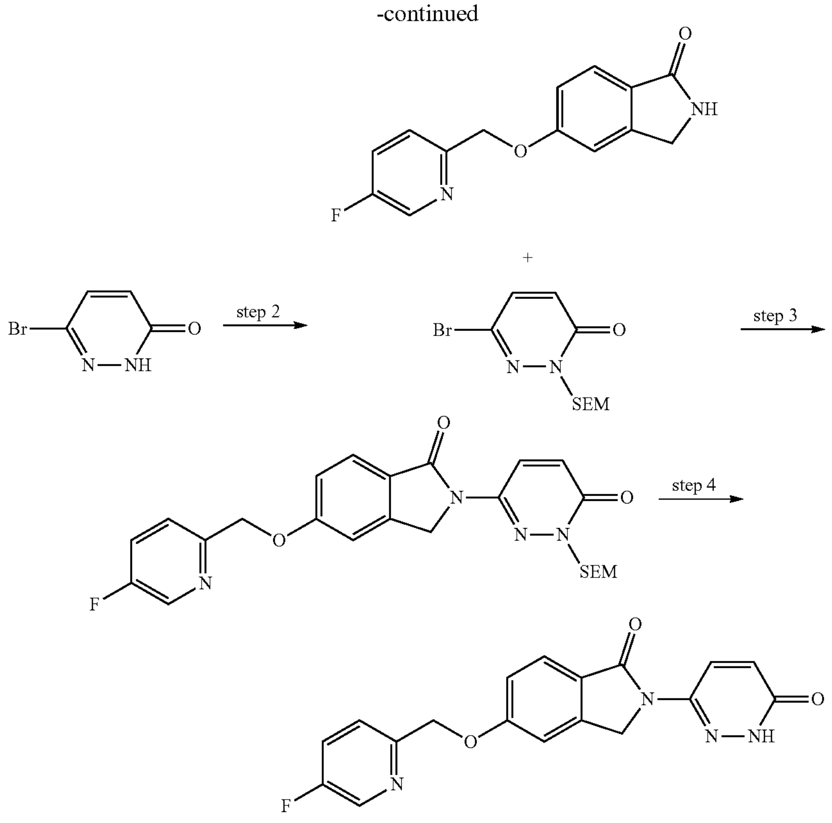

Example 9-1

Step 1: 5-[(5-Fluoro-2-pyridyl)methoxy]isoindolin-1-one

5-Hydroxy-2,3-dihydro-1H-isoindol-1-one (400 mg, 2.68 mmol), 2-(chloromethyl)-5-fluoro-pyridine (468 mg, 3.22 mmol), and potassium carbonate (1.11 g, 8.05 mmol) were combined in DMF (50 mL) and stirred at 70° C. for 3 h. The reaction mixture was concentrated and partitioned between DCM (30 mL) and water (10 mL). The resulting precipitate was collected and dried by vacuum filtration to afford the title compound (667 mg, 92% yield). $^1H$ NMR (500 MHz, DMSO-$d_6$) 8.60 (d, J=2.9 Hz, 1H), 8.34 (s, 1H), 7.80 (td, J=8.7, 2.9 Hz, 1H), 7.64 (dd, J=8.7, 4.5 Hz, 1H), 7.59 (d, J=8.4 Hz, 1H), 7.22 (d, J=1.9 Hz, 1H), 7.12 (dd, J=8.4, 2.3 Hz, 1H), 5.26 (s, 2H), 4.31 (s, 2H). $^{19}F$ NMR (471 MHz, DMSO-$d_6$) −128.46 (dd, J=8.8, 4.5 Hz). Tr(METCR1410)=0.94 min, ($ES^+$) $(M+H)^+$ 259.0, 96%.

Step 2: 2-[(6-Bromopyridazin-3-yl)oxymethoxy]ethyl-trimethyl-silane 2-(Chloromethoxy)ethyl-trimethyl-silane (8.0 mL, 45.7 mmol) was added to a solution of 3-bromo-1H-pyridazin-6-one (4.00 g, 22.9 mmol) and potassium carbonate (9.48 g, 68.6 mmol) in DMF (80 mL) at room temperature. The reaction was stirred at room temperature for 20 h. The reaction mixture was re-treated with 2-(chloromethoxy)ethyl-trimethyl-silane (4.9 mL, 27.4 mmol), stirred for a further 2 h, and concentrated to dryness. DCM (75 mL) was added and the organic phase was washed with water (2×50 mL) and brine (30 mL). The organic phase was dried over $Na_2SO_4$, filtered, and concentrated in vacuo. The crude residue was purified by column chromatography (silica, 0-100% EtOAc in heptane) to give the title compound (4.27 g, 61% yield). $^1H$ NMR (400 MHz, DMSO-$d_6$) 7.62 (d, J=9.7 Hz, 1H), 6.97 (d, J=9.7 Hz, 1H), 5.28 (s, 2H), 3.68-3.58 (m, 2H), 0.91-0.82 (m, 2H), −0.04 (s, 9H). Tr(METCR1410)=1.31 min, ($ES^+$) $(M+H)^+$ 356.8, 358.7, 100%.

Step 3: 5-[(5-Fluoro-2-pyridyl)methoxy]-2-[6-oxo-1-(2-trimethylsilylethoxymethyppyridazin-3-yl]isoindolin-1-one A solution of 5-[(5-fluoro-2-pyridyl)methoxy]isoindolin-1-one (200 mg, 0.774 mmol) and 6-bromo-2-(2-trimethylsilylethoxymethyl)pyridazin-3-one (260 mg, 0.852 mmol) in 1,4-dioxane (15 mL) was degassed in a pressure tube for 5 min, then RuPhos (11 mg, 0.0232 mmol) and $Pd_2(dba)_3$ (21 mg, 0.023 mmol) were added. The reaction was degassed for a further 5 min, and $Cs_2CO_3$ (0.30 g, 0.929 mmol) was added. The reaction was degassed for 5 min and stirred at 100° C. for 2 h. The cooled reaction mixture was re-treated with 5-[(5-fluoro-2-pyridyl)methoxy]isoindolin-1-one (50 mg, 0.19 mmol) and stirred overnight. The cooled reaction mixture was filtered and the filtrate concentrated. The residue was suspended in DCM (20 mL) and washed (10 mL). The organic phase was dried using a separator cartridge and concentrated in vacuo. The crude residue was purified by column chromatography (silica, 0-100% EtOAc in heptane) to give the title compound (281 mg, 74% yield). $^1H$ NMR (500 MHz, DMSO-$d_6$) 8.65-8.57 (m, 2H), 7.80 (td, J=8.7, 2.9 Hz, 1H), 7.74 (d, J=8.5 Hz, 1H), 7.66 (dd, J=8.7, 4.5 Hz, 1H), 7.35 (d, J=1.9 Hz, 1H), 7.20 (dd, J=8.5, 2.3 Hz, 1H), 7.12 (d, J=10.1 Hz, 1H), 5.38-5.24 (m, 4H), 4.87 (s, 2H), 3.74-3.66 (m, 2H), 0.92-0.87 (m, 2H), −0.03 (s, 9H). Tr(METCR1410)=1.38 min, ($ES^+$) $(M+H)^+$ 483.0, 100%.

Step 4: 5-[(5-Fluoro-2-pyridyl)methoxy]-2-(6-oxo-1H-pyridazin-3-yl)isoindolin-1-one TFA (1.1 mL, 14.6 mmol) was added to a solution of 5-[(5-fluoro-2-pyridyl)methoxy]-2-[6-oxo-1-(2-trimethylsilylethoxymethyl)pyridazin-3-yl]isoindolin-1-one (100%, 281 mg, 0.582 mmol) in DCM (9 mL), and the reaction was stirred at room temperature for 2.5 hours. The reaction mixture was concentrated in vacuo, redissolved in DCM, and concentrated again (×3). The crude residue was partitioned between DCM (3 mL) and sat. $NaHCO_3$ solution (2 mL), and the organic fraction separated and dried using a separator cartridge. The dried organic fraction was concentrated in vacuo to afford the title compound (24 mg, 11% yield).

Example 9-1: 5-[(5-Fluoro-2-pyridyl)methoxy]-2-(6-oxo-1H-pyridazin-3-yl)isoindolin-1-one $^1H$ NMR (500 MHz, DMSO-$d_6$) 12.78 (s, 1H), 8.61 (d, J=2.9 Hz, 1H), 8.60-8.53 (m, 1H), 7.81 (td, J=8.8, 2.9 Hz, 1H), 7.73 (d, J=8.5 Hz, 1H), 7.67 (dt, J=8.8, 4.6 Hz, 1H), 7.36 (d, J=1.9 Hz, 1H), 7.24-7.16 (m, 1H), 7.05 (m, 1H), 5.31 (s, 2H), 4.87 (m, 2H). $^{19}F$ NMR (471 MHz, DMSO-$d_6$) −128.31 (ddd, J=13.3, 8.8, 4.6 Hz). Tr(MET-uHPLC-AB-101)=2.26 min m/z ($ES^+$)$(M+H)^+$ 353.1, 99%.

The following additional compounds were prepared by Method 9:

Example 9-2: 5-((5-(2-Fluoroethoxy-1,1,2,2-$^2H_4$)pyridin-2-yl)methoxy)-2-(6-oxo-1,6-dihydropyridazin-3-yl)isoindolin-1-one

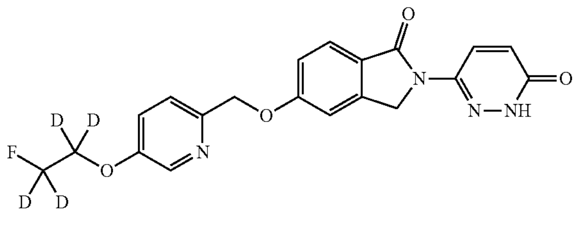 [SMILES: [2H]C([2H])(F)C([2H])([2H])Oc1ccc(COc2ccc3c(c2)CN(c2ccc(=O)[nH]n2)C3=O)nc1]

$^1H$ NMR (500 MHz, DMSO-$d_6$) 12.77 (s, 1H), 8.56 (d, J=10.5 Hz, 1H), 8.34 (d, J=2.5 Hz, 1H), 7.72 (d, J=8.5 Hz, 1H), 7.52 (d, J=8.5 Hz, 1H), 7.48 (dd, J=8.5, 2.5 Hz, 1H), 7.34 (d, J=2.0 Hz, 1H), 7.17 (dd, J=8.5, 2.0 Hz, 1H), 7.02 (d, J=10.5 Hz, 1H), 5.23 (s, 2H), 4.86 (s, 2H). $^{19}F$ NMR (282 MHz, DMSO-$d_6$) −224.22. Tr(MET-uHPLC-006)=3.83 min m/z ($ES^+$) $(M+H)^+$ 401.1, 99%.

Example 9-3: 5-((5-Fluoro-4-methoxypyridin-2-yl)methoxy)-2-(6-oxo-1,6-dihydropyridazin-3-yl)isoindolin-1-one

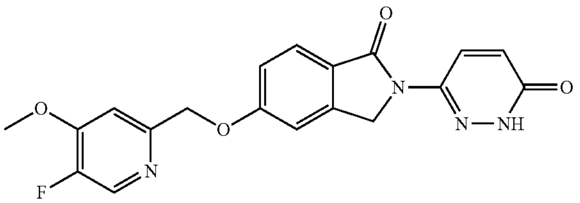 [SMILES: COc1cc(COc2ccc3c(c2)CN(c2ccc(=O)[nH]n2)C3=O)ncc1F]

$^1H$ NMR (500 MHz, DMSO-$d_6$) 12.77 (s, 1H), 8.57 (d, J=10.2 Hz, 1H), 8.43 (d, J=3.2 Hz, 1H), 7.73 (d, J=8.4 Hz, 1H), 7.44 (d, J=7.0 Hz, 1H), 7.36 (d, J=1.6 Hz, 1H), 7.21 (dd, J=8.4, 2.1 Hz, 1H), 7.02 (d, J=10.1 Hz, 1H), 5.22 (s, 2H), 4.87 (s, 2H), 3.95 (s, 3H). $^{19}F$ NMR (282 MHz, DMSO-$d_6$) −152.73. Tr(MET-uHPLC-006)=3.88 min m/z (ES+) (M+H)+ 383.1, 99%.

Method 10

Scheme for Method 10

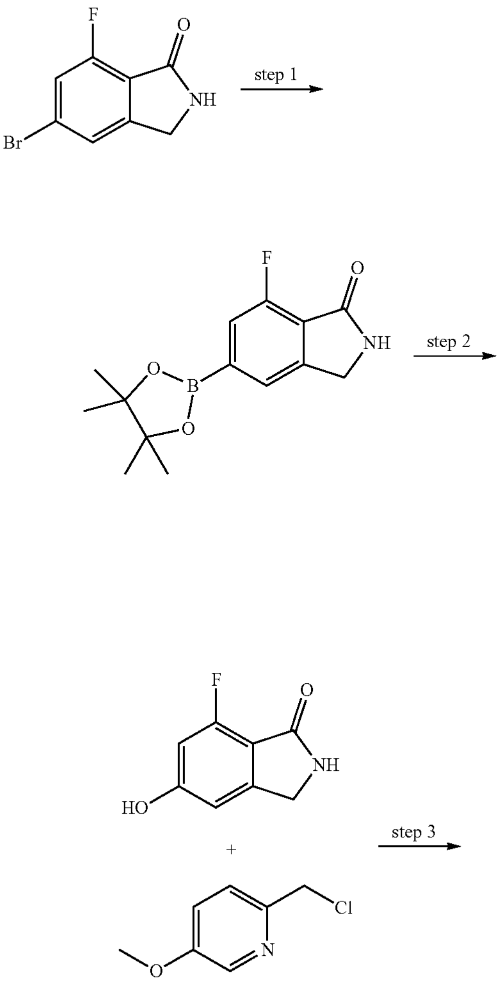

-continued

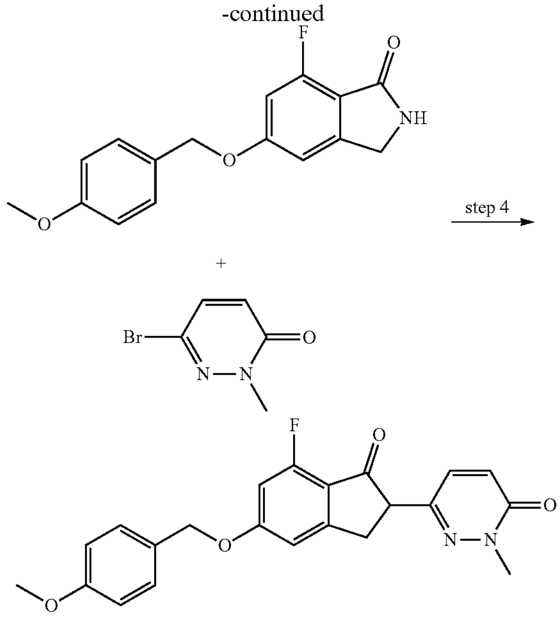

Example 10-1

Step 1: 7-Fluoro-5-(4,4,5,5-tetramethyl-1,3,2-dioxaborolan-2-yl)isoindolin-1-one A mixture of 5-bromo-7-fluoroisoindolin-1-one (500 mg, 2.17 mmol), bis(pinacolato)diboron (828 mg, 3.26 mmol), potassium acetate (533 mg, 5.43 mmol), and $Pd(dppf)Cl_2$ (159 mg, 0.217 mmol) in 1,4-dioxane (15.7 mL) was heated at 90° C. for 2 h. After this time, the reaction mixture was cooled, poured into water (50 mL), and extracted with DCM (3x30 mL). The combined organic layers were dried over sodium sulfate, filtered, and concentrated in vacuo to afford the title compound (870 mg, >99%). $^1$H NMR (300 MHz, $CDCl_3$) 7.67 (s, 1H), 7.52 (d, J=9.6 Hz, 1H), 6.53 (br s, 1H), 4.45 (s, 2H), 1.24 (s, 12H). MS ($ES^+$) $(M+H)^+$ 278.

Step 2: 7-Fluoro-5-hydroxyisoindolin-1-one

A solution of sodium perborate tetrahydrate (580 mg, 3.77 mmol) in water (53.6 mL) was added to a solution of 7-fluoro-5-(4,4,5,5-tetramethyl-1,3,2-dioxaborolan-2-yl)isoindolin-1-one (870 mg, 3.14 mmol) in THF (53.7 mL), and the mixture was stirred at rt for 1 h. After this time, sat. aq ammonium chloride (200 mL) was added, and the volatiles were removed in vacuo. The remaining aqueous mixture was extracted with 3:1 chloroform/IPA (3x100 mL), and the combined organic layers were dried over sodium sulfate, filtered, and concentrated in vacuo. The residue obtained was purified by FCC (silica, 0-10% MeOH in DCM) to afford the title compound (111 mg, 31%). $^1$H NMR (300 MHz, DMSO-$d_6$) 10.56 (br s, 1H), 8.22 (br s, 1H), 6.73 (d, J=1.5 Hz, 1H), 6.55 (dd, J=11.7, 1.8 Hz, 1H), 4.27 (s, 2H). MS ($ES^+$) $(M+H)^+$ 168.

Step 3: 7-Fluoro-5-((5-methoxypyridin-2-yl)methoxy)isoindolin-1-one

Potassium carbonate (521 mg, 3.77 mmol) was added to a solution of 7-fluoro-5-hydroxyisoindolin-1-one (210 mg, 1.26 mmol) and 2-(chloromethyl)-5-methoxypyridine (198 mg, 1.26 mmol) in DMF (9.7 mL), and the mixture was stirred at rt for 16 h. After this time, water (100 mL) was added, and the mixture was extracted with DCM (2x100 mL). The combined organic layers were dried over sodium sulfate, filtered, and the filtrate was concentrated in vacuo. The residue obtained was purified by FCC (silica, 0-5% MeOH in DCM) to afford the title compound (200 mg, 55%). $^1$HNMR (300 MHz, DMSO-$d_6$) 8.37 (br s, 1H), 8.30 (d, J=2.4 Hz, 1H), 7.51 (d, J=8.4 Hz, 1H), 7.44 (dd, J=8.7, 3.0 Hz, 1H), 7.05 (d, J=1.8 Hz, 1H), 6.94 (dd, J=11.4, 1.8 Hz, 1H), 5.18 (s, 2H), 4.32 (s, 2H), 3.84 (s, 3H).

Step 4: 7-Fluoro-5-[(5-methoxypyridin-2-yl)methoxy]-2-(1-methyl-6-oxo-1,6-dihydropyridazin-3-yl)-2,3-dihydro-1H-isoindol-1-one A mixture of 7-fluoro-5-((5-methoxypyridin-2-yl)methoxy)isoindolin-1-one (100 mg, 0.347 mmol), 6-bromo-2-methyl-3(2H)-pyridazinone (79 mg, 0.42 mmol), RuPhos (24 mg, 0.052 mmol), cesium carbonate (339 mg, 1.04 mmol), and $Pd_2(dba)_3$ (16 mg, 0.017 mmol) in 1,4-dioxane (11.1 mL) was heated at 100° C. for 16 h. After this time, the reaction mixture was cooled, combined with water (50 mL), and extracted with DCM (3x100 mL). The combined organic layers were dried over sodium sulfate, filtered, and the filtrate was concentrated in vacuo. The residue obtained was purified by FCC (silica, 0-5% MeOH in DCM) to afford the title compound (81 mg, 59%).

Example 10-1: 7-Fluoro-5-[(5-methoxypyridin-2-yl)methoxy]-2-(1-methyl-6-oxo-1,6-di-hydropyridazin-3-yl)-2,3-dihydro-1H-isoindol-1-one $^1$H NMR (500 MHz, DMSO-$d_6$) 8.50 (d, J=10.0 Hz, 1H), 8.31 (d, J=2.5 Hz, 1H), 7.53 (d, J=8.5 Hz, 1H), 7.45 (dd, J=8.5, 2.5 Hz, 1H), 7.19 (s, 1H), 7.09-7.05 (m, 2H), 5.22 (s, 2H), 4.88 (s, 2H), 3.85 (s, 3H), 3.63 (s, 3H). $^{19}$F NMR (282 MHz, DMSO-$d_6$) −116.43. Tr(MET-uHPLC-001)=3.65 min, ($ES^+$) $(M+H)^+$ 397.1, 100%.

The following additional compounds were prepared by Method 10:

Example 10-2: 7-Fluoro-5-[(5-methoxypyridin-2-yl)methoxy]-2-(6-oxo-1,6-dihydropyridazin-3-yl)-2,3-dihydro-1H-isoindol-1-one

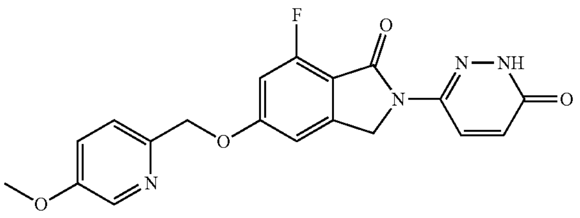 [SMILES: COc1ccc(COc2cc(F)c3c(c2)CN(c2ccc(=O)[nH]n2)C3=O)nc1]

$^1$H NMR (500 MHz, DMSO-$d_6$) 12.80 (s, 1H), 8.49 (d, J=10.0 Hz, 1H), 8.31 (d, J=2.5 Hz, 1H), 7.52 (d, J=8.5 Hz, 1H), 7.45 (dd, J=9.0, 3.0 Hz, 1H), 7.18 (d, J=2.0 Hz, 1H), 7.05 (dd, J=11.5, 2.0 Hz, 1H), 7.02 (dd, J=10.0, 1.5 Hz, 1H), 5.22 (s, 2H), 4.86 (s, 2H), 3.84 (s, 3H). $^{19}$F NMR (282 MHz, DMSO-$d_6$) −116.59. Tr(MET-uHPLC-001)=2.50 min m/z ($ES^+$) $(M+H)^+$ 383.1, 100%.

Method 11

Scheme for Method 11

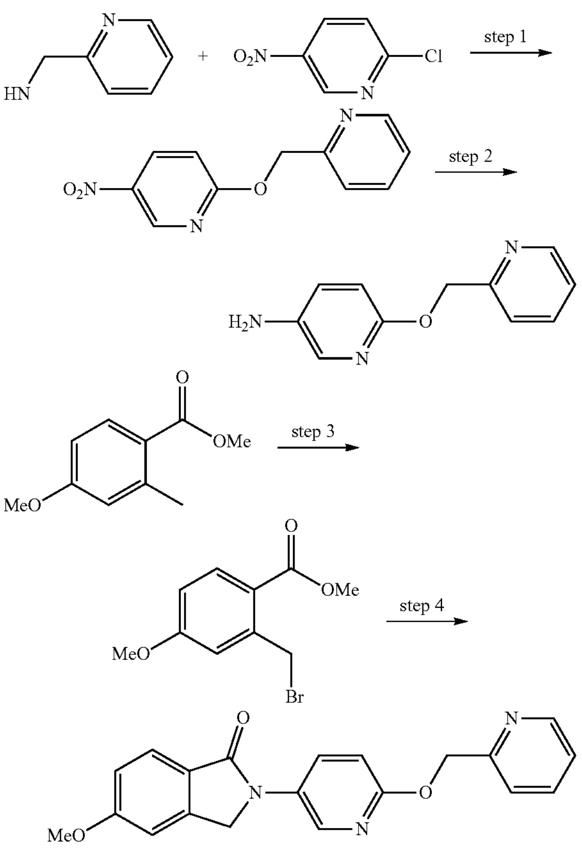

Step 1: 5-Nitro-2-[(pyridin-2-yl)methoxy]pyridine

Pyridin-3-ylmethanol (0.31 mL, 3.15 mmol) was added dropwise to a suspension of sodium hydride (132 mg, 3.31 mmol) in tetrahydrofuran (10 mL) under nitrogen with ice cooling. The mixture was left stirring for 10 min. A solution of 2-chloro-5-nitropyridine (500 mg, 3.15 mmol) in tetrahydrofuran (5 mL) was then added slowly. The mixture was left stirring with ice cooling for 1 h. The mixture was quenched using water (1 mL), diluted with further water (30 mL), and extracted with ethyl acetate (2×30 mL). The combined organic extracts were dried over $Na_2SO_4$, filtered, and concentrated to afford the title compound (737 mg, quant. yield). $^1$H NMR (250 MHz, DMSO-$d_6$) 9.18-9.07 (m, 1H), 8.71 (d, J=1.7 Hz, 1H), 8.56 (dd, J=4.8, 1.6 Hz, 1H), 8.52 (dd, J=9.1, 2.9 Hz, 1H), 7.91 (dt, J=7.8, 2.0 Hz, 1H), 7.48-7.39 (m, 1H), 7.12 (dd, J=9.1, 0.5 Hz, 1H), 5.53 (s, 2H). Tr(METCR1278)=1.16 min, (ES$^+$) (M+H)$^+$ 232, 100%.

Step 2: 6-[(Pyridin-2-yl)methoxy]pyridin-3-amine

A stirred suspension of 5-nitro-2-[(pyridin-2-yl)methoxy] pyridine (729 mg, 3.15 mmol) in ethanol (15 mL) was heated to 70° C. Ammonium chloride (1.65 g, 31.5 mmol) in water (5 mL) was then added, followed by iron powder (0.704 g, 12.6 mmol) in one portion. The reaction was stirred for 1 h at 80° C. The mixture was then filtered through glass fibre filter and the inorganics were washed with ethyl acetate (20 mL) and water (20 mL). The filtrate was then partitioned between ethyl acetate (80 mL) and water (80 mL). The aqueous extract was then further extracted with ethyl acetate (80 mL). The combined organic extracts were dried ($Na_2SO_4$), filtered, and concentrated to afford the title compound (0.62 g, 98% yield). $^1$H NMR (500 MHz, DMSO-$d_6$) 8.62 (d, J=1.7 Hz, 1H), 8.50 (dd, J=4.8, 1.5 Hz, 1H), 7.81 (d, J=7.8 Hz, 1H), 7.50 (d, J=2.6 Hz, 1H), 7.38 (dd, J=7.8, 4.8 Hz, 1H), 7.02 (dd, J=8.7, 2.9 Hz, 1H), 6.62 (d, J=8.6 Hz, 1H), 5.23 (s, 2H), 4.79 (s, 2H). Tr(METCR1278)=solvent front, (ES$^+$) (M+H)$^+$ 202.

Step 3: Ethyl 2-(bromomethyl)-4-methoxybenzoate

Ethyl 4-methoxy-2-methylbenzoate (900 mg, 4.63 mmol) and NBS (907 mg, 5.10 mmol) were dissolved in DCE (35 mL). AIBN (76 mg, 0.46 mmol) was added to the reaction mixture and the resulting solution heated to reflux for 2 h. The reaction mixture was cooled and concentrated. Column chromatography of the crude residue (silica, 2-20% EtOAc-heptane) afforded the title compound (806 mg, 64%). $^1$H NMR (500 MHz, $CDCl_3$) 7.99 (d, J=8.75 Hz, 1H), 6.96 (d, J=2.63 Hz, 1H), 6.86 (dd, J=2.64, 8.76 Hz, 1H), 4.96 (s, 2H), 4.37 (q, J=7.13 Hz, 2H), 3.86 (s, 3H), 1.41 (t, J=7.14 Hz, 3H). Tr(METCR1278)=2.17 min, (ES$^+$) (M+H)$^+$ 273, 275, 99%.

Step 4: 5-Methoxy-2-{6-[(pyridin-3-yl)methoxy] pyridin-3-yl}-2,3-dihydro-1H-isoindol-1-one N,N-Diethylisopropylamine (0.038 mL, 0.22 mmol) was added to 6-(pyridin-3-ylmethoxy)pyridin-3-amine (37 mg, 0.18 mmol) and ethyl 2-(bromomethyl)-4-methoxybenzoate (50 mg, 0.18 mmol) in ethanol (2 mL), was added under nitrogen. The mixture was heated at 110° C. in a sealed tube overnight. The mixture was then diluted with water (4 mL) and filtered. The collected solid was then purified by FCC (silica, 0-5% methanol in dichloromethane) then purified by preparative HPLC (water-acetonitrile) to afford the title compound (6.1 mg, 10% yield).

Example 11-1: 5-Methoxy-2-{6-[(pyridin-3-yl) methoxy]pyridin-3-yl}-2,3-dihydro-1H-isoindol-1-one $^1$H NMR (500 MHz, DMSO-$d_6$) 8.69 (d, J=1.7 Hz, 1H), 8.61-8.48 (m, 2H), 8.30 (dd, J=9.0, 2.8 Hz, 1H), 7.88 (dt, J=7.8, 2.0 Hz, 1H), 7.69 (d, J=8.4 Hz, 1H), 7.42 (dd, J=7.8, 4.8 Hz, 1H), 7.21 (d, J=1.9 Hz, 1H), 7.09 (dd, J=8.4, 2.3 Hz, 1H), 7.00 (d, J=9.0 Hz, 1H), 5.40 (s, 2H), 4.96 (s, 2H), 3.87 (s, 3H). Tr(MET-uHPLC-AB-101)=1.87 min, (ES$^+$) (M+H)$^+$ 348, 97%

Method 12

Scheme for Method 12

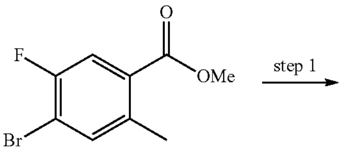

-continued

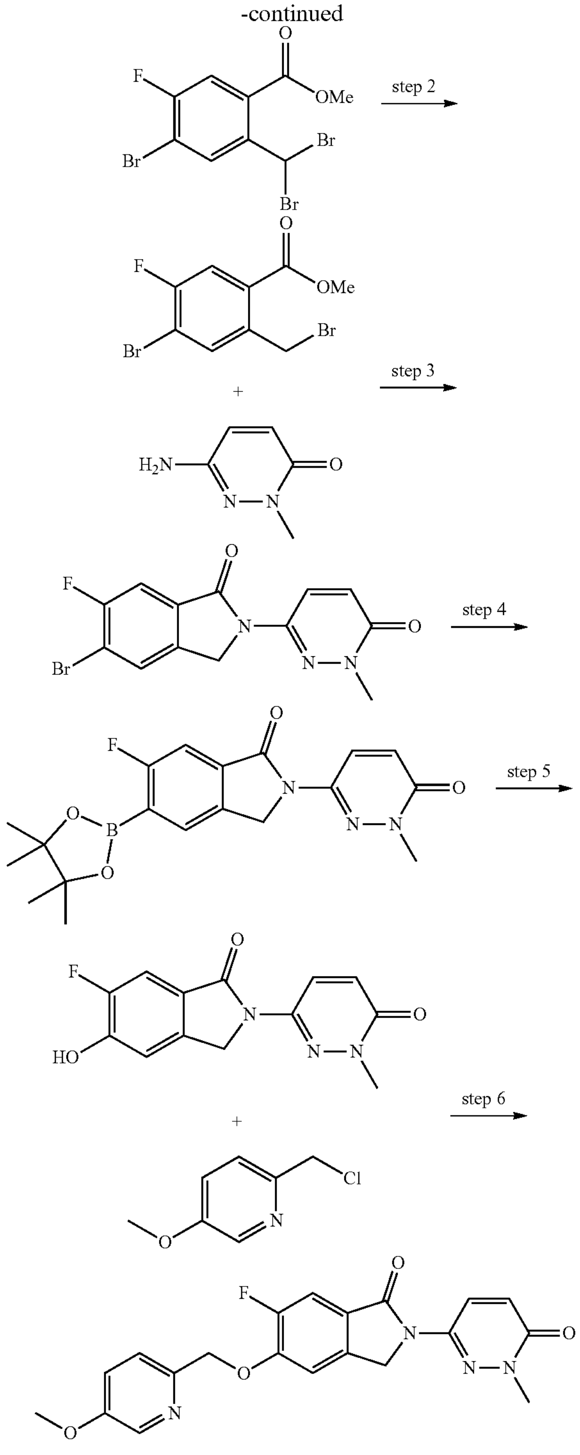

Example 12-1

Step 1: Methyl 4-bromo-2-(dibromomethyl)-5-fluorobenzoate

To a solution of methyl 4-bromo-5-fluoro-2-methylbenzoate (600 mg, 2.43 mmol) in carbon tetrachloride (40 mL) was added NBS (1.08 g, 6.07 mmol) and AIBN (8 mg, 0.05 mmol), and the mixture was stirred at 80° C. overnight. After this time, the volatiles were removed under reduced pressure, and the residue obtained was purified by FCC (silica, 0-5% EtOAc in hexanes) to afford the title compound (720 mg, 73%). $^1$H NMR (300 MHz, $CDCl_3$) 8.37 (d, J=6.5 Hz, 1H), 7.97 (s, 1H), 7.65 (d, J=8.8 Hz, 1H), 3.96 (s, 3H).

Step 2: Methyl 4-bromo-2-(bromomethyl)-5-fluorobenzoate

To a solution of methyl 4-bromo-2-(dibromomethyl)-5-fluorobenzoate (670 mg, 1.65 mmol) and DIPEA (91 mg, 6.6 mmol) in THF (70 mL) was added diethyl phosphonate (856 mg, 6.62 mmol), and the mixture was stirred at rt for 18 h. After this time, the volatiles were removed under reduced pressure, and the residue obtained was purified by FCC (silica, 0-5% EtOAc in hexanes) to afford the title compound (346 mg, 64%). $^1$H NMR (300 MHz, $CDCl_3$) 7.77-7.66 (m, 2H), 4.89 (s, 2H), 3.95 (s, 3H).

Step 3: 5-Bromo-6-fluoro-2-(1-methyl-6-oxo-1,6-dihydropyridazin-3-yl)isoindolin-1-one 6-Amino-2-methylpyridazin-3(2H)-one (286 mg, 2.29 mmol) and DIPEA (0.906 mL, 5.20 mmol) were added to a solution of methyl 4-bromo-2-(bromomethyl)-5-fluorobenzoate (339 mg, 1.04 mmol) in DMF (14.6 mL), and the mixture was stirred at 80° C. for 16 h. After this time, the reaction mixture was concentrated in vacuo. The residue obtained was suspended in THF (7.3 mL) and EtOH (7.3 mL), and lithium hydroxide (65.0 mg, 2.70 mmol) was added. The mixture was stirred at rt for 2 h. After this time, the volatiles were removed in vacuo, and water (10 mL) was added. The solid that formed was collected by filtration and dried in vacuo to afford the title compound (217 mg, 62%). $^1$H NMR (300 MHz, DMSO-$d_6$) 8.54 (d, J=10.2 Hz, 1H), 8.12 (d, J=6.0 Hz, 1H), 7.80 (d, J=7.8 Hz, 1H), 7.12 (d, J=10.2 Hz, 1H), 4.92 (s, 2H), 3.65 (s, 3H). MS ($ES^+$) $(M+H)^+$ 339.

Step 4: 6-Fluoro-2-(1-methyl-6-oxo-1,6-dihydropyridazin-3-yl)-5-(4,4,5,5-tetramethyl-1,3,2-dioxaborolan-2-yl)isoindolin-1-one A mixture of 5-bromo-6-fluoro-2-(1-methyl-6-oxo-1,6-dihydropyridazin-3-yl)isoindolin-1-one (154 mg, 0.455 mmol), bis(pinacolato)diboron (173 mg, 0.683 mmol), potassium acetate (112 mg, 1.14 mmol), and Pd(dppf)$Cl_2$ (33 mg, 0.046 mmol) in 1,4-dioxane (8.2 mL) was heated at 90° C. for 6 h. After this time, the reaction mixture was cooled and concentrated in vacuo. The residue obtained was triturated in water (5 mL), and the solid that formed was collected by filtration, washed with water (5 mL), and dried in vacuo to afford the title compound (172 mg, 98%). $^1$H NMR (300 MHz, $CDCl_3$) 8.72 (d, J=9.9 Hz, 1H), 7.89 (d, J=4.5 Hz, 1H), 7.53 (d, J=8.1 Hz, 1H), 7.04 (d, J=9.9 Hz, 1H), 4.87 (s, 2H), 3.78 (s, 3H), 1.40 (s, 12H). MS ($ES^+$) $(M+H)^+$ 386.

Step 5: 6-Fluoro-5-hydroxy-2-(1-methyl-6-oxo-1,6-dihydropyridazin-3-yl)isoindolin-1-one A solution of sodium perborate tetrahydrate (172 mg, 1.12 mmol) in water (2.6 mL) was added to a solution of 6-fluoro-2-(1-methyl-6-oxo-1,6-dihydropyridazin-3-yl)-5-(4,4,5,5-tetramethyl-1,3,2-dioxaborolan-2-yl)isoindolin-1-one (172 mg, 0.447 mmol) in MeCN (12.9 mL), and the mixture was stirred at rt for 2 h. After this time, sat. aq ammonium chloride (1 mL) was added, and the mixture was concentrated in vacuo. Water (10 mL) was added, the pH was adjusted to 5 with 2 N hydrochloric acid, and the mixture was allowed to stand for 16 h. After this time, the solid that formed was collected by filtration, dried in vacuo and triturated in MeOH (8 mL) to afford the title compound (95 mg, 76%). $^1$H NMR (300 MHz, DMSO-$d_6$) 11.02 (br s, 1H), 8.55 (d, J=10.2 Hz, 1H), 7.54 (d, J=9.9 Hz, 1H), 7.22 (d, J=7.5 Hz, 1H), 7.08 (d, J=9.9 Hz, 1H), 4.82 (s, 2H), 3.63 (s, 3H). MS (ES$^+$) (M+H)$^+$ 276.

Step 6: 6-Fluoro-5-[(5-methoxypyridin-2-yl)methoxy]-2-(1-methyl-6-oxo-1,6-dihydropyridazin-3-yl)-2,3-dihydro-1H-isoindol-1-one Potassium carbonate (143 mg, 1.04 mmol) was added to a solution of 6-fluoro-5-hydroxy-2-(1-methyl-6-oxo-1,6-dihydropyridazin-3-yl)isoindolin-1-one (95 mg, 0.35 mmol) and 2-(chloromethyl)-5-methoxypyridine (65 mg, 0.41 mmol) in DMF (6.3 mL), and the mixture was stirred at 30° C. for 16 h. After this time, water (20 mL) was added, and the mixture was extracted with DCM (2×30 mL). The combined organic layers were dried over sodium sulfate, filtered, and the filtrate was concentrated in vacuo. The residue obtained was purified by FCC (silica, 0-5% MeOH in DCM) to afford the title compound (83 mg, 61%) as an off-white solid. The product was combined with another lot (19 mg) and dissolved in DCM (10 mL). The solution was added dropwise to hexanes (75 mL), and the solid that formed was collected by filtration, washed with hexanes (50 mL), and dried in vacuo to afford the title compound (73 mg).

Example 12-1: 6-Fluoro-5-[(5-methoxypyridin-2-yl)methoxy]-2-(1-methyl-6-oxo-1,6-dihydropyridazin-3-yl)-2,3-dihydro-1H-isoindol-1-one $^1$H NMR (500 MHz, DMSO-$d_6$) 8.69 (d, J=10.0 Hz, 1H), 8.31 (d, J=3.0 Hz, 1H), 7.57 (d, J=9.5 Hz, 1H), 7.49 (d, J=8.5 Hz, 1H), 7.27-7.24 (m, 1H), 7.17 (d, J=7.0 Hz, 1H), 7.01 (d, J=10.0 Hz, 1H), 5.31 (s, 2H), 4.81 (s, 2H), 3.88 (s, 3H), 3.75 (s, 3H). $^{19}$F NMR (282 MHz, DMSO-$d_6$) −131.86. Tr(MET-uHPLC-001)=4.53 min, (ES$^+$) (M+H)$^+$ 397.1, 100%.

The following additional compounds were prepared by Method 12:

Example 12-2: 4-Fluoro-5-[(5-methoxypyridin-2-yl)methoxy]-2-(1-methyl-6-oxo-1,6-dihydropyridazin-3-yl)-2,3-dihydro-1H-isoindol-1-one

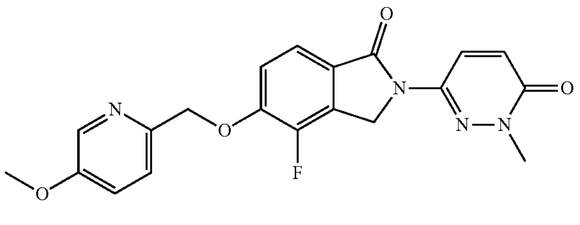 [SMILES: COc1ccc(COc2ccc3c(c2F)CN(c2ccc(=O)n(C)n2)C3=O)nc1]

$^1$H NMR (300 MHz, DMSO-$d_6$) 8.55 (d, J=10.0 Hz, 1H), 8.31 (d, J=2.5 Hz, 1H), 7.62 (d, J=8.3 Hz, 1H), 7.58-7.42 (m, 3H), 7.10 (d, J=10.0 Hz, 1H), 5.31 (s, 2H), 4.98 (s, 2H), 3.84 (s, 3H), 3.65 (s, 3H). $^{19}$F NMR (282 MHz, DMSO-$d_6$) −141.12. Tr(MET-uHPLC-006)=4.28 min m/z (ES$^+$) (M+H)$^+$ 397.0, 99%.

Example 12-3: 4-Fluoro-6-[(5-methoxypyridin-2-yl)methoxy]-2-(1-methyl-6-oxo-1,6-dihydropyridazin-3-yl)-2,3-dihydro-1H-isoindol-1-one

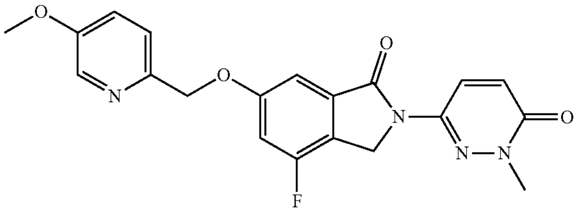 [SMILES: COc1ccc(COc2cc(F)c3c(c2)C(=O)N(c2ccc(=O)n(C)n2)C3)nc1]

$^1$H NMR (500 MHz, DMSO-$d_6$) 8.52 (d, J=10.0 Hz, 1H), 8.30 (d, J=3.0 Hz, 1H), 7.50 (d, J=8.5 Hz, 1H), 7.43 (dd, J=8.5, 3.0 Hz, 1H), 7.30 (dd, J=10.5, 2.0 Hz, 1H), 7.27 (d, J=1.5 Hz, 1H), 7.10 (d, J=10.0 Hz, 1H), 5.23 (s, 2H), 4.92 (s, 2H), 3.83 (s, 3H), 3.65 (s, 3H). $^{19}$F NMR (282 MHz, DMSO-$d_6$) −117.70. Tr(MET-uHPLC-001)=4.33 min m/z (ES$^+$) (M+H)$^+$ 397.2, 99%.

Example 12-4: 5-Fluoro-6-[(5-methoxypyridin-2-yl)methoxy]-2-(1-methyl-6-oxo-1,6-dihydropyridazin-3-yl)-2,3-dihydro-1H-isoindol-1-one

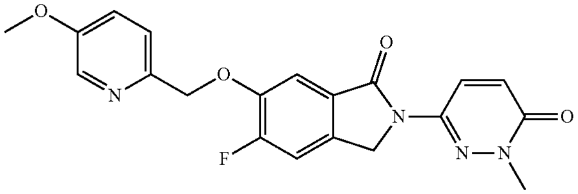 [SMILES: COc1ccc(COc2cc3c(cc2F)CN(c2ccc(=O)n(C)n2)C3=O)nc1]

$^1$H NMR (500 MHz, DMSO-$d_6$) 8.54 (d, J=9.9 Hz, 1H), 8.30 (d, J=2.6 Hz, 1H), 7.61 (d, J=9.0 Hz, 1H), 7.59 (d, J=6.3 Hz, 1H), 7.51 (d, J=8.6 Hz, 1H), 7.45 (dd, J=8.6, 2.9 Hz, 1H), 7.09 (d, J=9.9 Hz, 1H), 5.30 (s, 2H), 4.85 (s, 2H), 3.83 (s, 3H), 3.63 (s, 3H). $^{19}$F NMR (282 MHz, DMSO-$d_6$) −125.54. Tr(MET-uHPLC-001)=4.41 min m/z (ES+) (M+H)+ 397.0, 99%.

Example 12-5: 6-{3-[(5-Methoxypyridin-2-yl)methoxy]-7-oxo-5H,6H,7H-pyrrolo[3,4-b]pyridin-6-yl}-2-methyl-2,3-dihydropyridazin-3-one

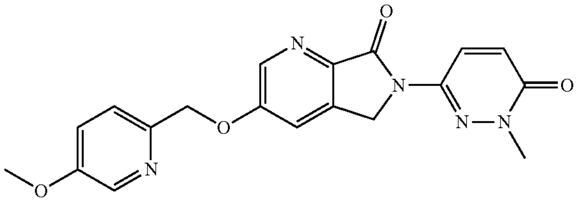 [SMILES: COc1ccc(COc2cnc3c(c2)CN(c2ccc(=O)n(C)n2)C3=O)nc1]

$^1$H NMR (500 MHz, DMSO-$d_6$) 8.58 (d, J=10.0 Hz, 1H), 8.54 (d, J=3.0 Hz, 1H), 8.32 (d, J=3.0 Hz, 1H), 7.82 (d, J=2.5 Hz, 1H), 7.56 (d, J=8.5 Hz, 1H), 7.46 (dd, J=8.6, 2.7 Hz, 1H), 7.10 (d, J=10.0 Hz, 1H), 5.29 (s, 2H), 4.89 (s, 2H), 3.84 (s, 3H), 3.65 (s, 3H). Tr(MET-uHPLC-001)=4.39 min, (ES+) (M+H)+ 380.3, 99%.

Example 12-6: 6-(3-{[5-(2-Fluoroethoxy)pyridin-2-yl]methoxy}-7-oxo-5H,6H,7H-pyrrolo[3,4-b]pyridin-6-yl)-2-methyl-2,3-dihydropyridazin-3-one

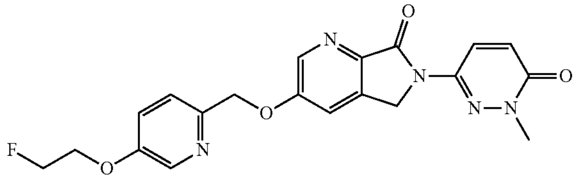 [SMILES: Cn1nc(N2Cc3cc(OCc4ccc(OCCF)cn4)cnc3C2=O)ccc1=O]

$^1$H NMR (500 MHz, DMSO-$d_6$) 8.58 (d, J=10.0 Hz, 1H), 8.54 (d, J=2.6 Hz, 1H), 8.35 (d, J=2.9 Hz, 1H), 7.82 (d, J=2.6 Hz, 1H), 7.57 (d, J=8.5 Hz, 1H), 7.50 (dd, J=8.5, 2.9 Hz, 1H), 7.09 (d, J=10.0 Hz, 1H), 5.31 (s, 2H), 4.89 (s, 2H), 4.77 (dt, J=47.7, 3.9 Hz, 2H), 4.36 (dt, J=31.0, 4.0 Hz, 2H), 3.65 (s, 3H). $^{19}$F NMR (282 MHz, DMSO-$d_6$) −222.32. Tr(MET-uHPLC-001)=3.23 min, (ES+) (M+H)+ 412.4, 98%.

Example 12-7: 6-{3-[(5-Fluoropyridin-2-yl)methoxy]-7-oxo-5H,6H,7H-pyrrolo[3,4-b]pyridin-6-yl}-2-methyl-2,3-dihydropyridazin-3-one

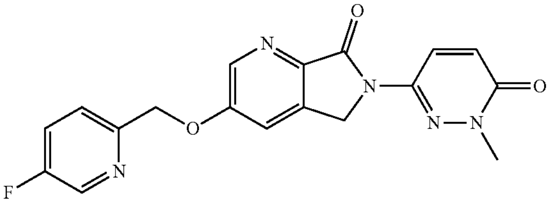 [SMILES: Cn1nc(N2Cc3cc(OCc4ccc(F)cn4)cnc3C2=O)ccc1=O]

$^1$H NMR (500 MHz, $CDCl_3$) 8.78 (d, J=10.0 Hz, 1H), 8.60 (d, J=2.5 Hz, 1H), 8.49 (d, J=2.5 Hz, 1H), 7.55 (dd, J=9.0, 4.5 Hz, 1H), 7.49 (td, J=8.0, 3.0 Hz, 1H), 7.41 (d, J=2.5 Hz, 1H), 7.04 (d, J=10.0 Hz, 1H), 5.33 (s, 2H), 4.88 (s, 2H), 3.76 (s, 3H). $^{19}$F NMR (282 MHz, $CDCl_3$) −126.65. Tr(MET-uHPLC-001)=3.76 min m/z (ES+) (M+H)+ 368.1, 100%.

Example 12-8: 6-{3-[(3-Fluoro-5-methoxypyridin-2-yl)methoxy]-7-oxo-5H,6H,7H-pyrrolo[3,4-b]pyridin-6-yl}-2-methyl-2,3-dihydropyridazin-3-one

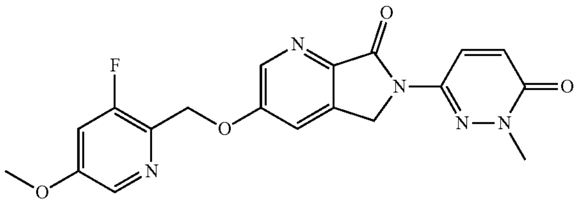 [SMILES: COc1cnc(COc2cnc3c(c2)CN(c2ccc(=O)n(C)n2)C3=O)c(F)c1]

$^1$H NMR (500 MHz, DMSO-$d_6$) 8.58 (d, J=10.0 Hz, 1H), 8.53 (d, J=2.5 Hz, 1H), 8.23 (d, J=2.0 Hz, 1H), 7.86 (d, J=2.5 Hz, 1H), 7.55 (dd, J=11.5, 2.5 Hz, 1H), 7.10 (d, J=10.0 Hz, 1H), 5.36 (d, J=2.0 Hz, 2H), 4.90 (s, 2H), 3.89 (s, 3H), 3.66 (s, 3H). $^{19}$F NMR (282 MHz, DMSO-$d_6$) −123.19. Tr(MET-uHPLC-001)=3.96 min m/z (ES+) (M+H)+ 398.4, 99%.

Example 12-9: 6-[3-([5-[2-Fluoro(1,1,2,2-$^2H_4$)ethoxy]pyridin-2-yl]methoxy)-7-oxo-5H,6H,7H-pyrrolo[3,4-b]pyridin-6-yl]-2-methyl-2,3-dihydropyridazin-3-one

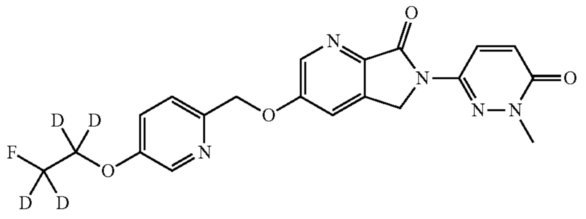

$^1$H NMR (500 MHz, DMSO-$d_6$) 8.58 (d, J=10.0 Hz, 1H), 8.54 (d, J=2.5 Hz, 1H), 8.35 (d, J=3.0 Hz, 1H), 7.82 (d, J=3.0 Hz, 1H), 7.57 (d, J=8.5 Hz, 1H), 7.50 (dd, J=8.5, 3.0 Hz, 1H), 7.10 (d, J=10.0 Hz, 1H), 5.30 (s, 2H), 4.89 (s, 2H), 3.65 (s, 3H). $^{19}$F NMR (282 MHz, $CDCl_3$) −224.24. Tr(MET-uHPLC-002)=2.67 min m/z (ES+) (M+H)+ 416.2, 100%.

Example 12-10: 7-Fluoro-6-[(5-methoxypyridin-2-yl)methoxy]-2-(1-methyl-6-oxo-1,6-dihydropyridazin-3-yl)-2,3-dihydro-1H-isoindol-1-one

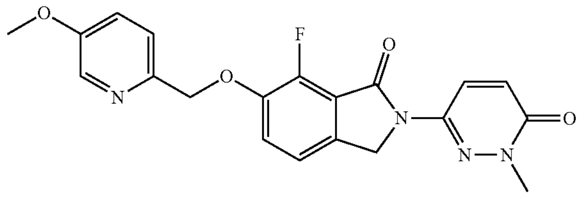 [SMILES: COc1ccc(COc2ccc3c(c2F)C(=O)N(c2ccc(=O)n(C)n2)C3)nc1]

$^1$H NMR (500 MHz, DMSO-$d_6$) 8.49 (d, J=10.0 Hz, 1H), 8.29 (d, J=2.9 Hz, 1H), 7.61 (t, J=8.0 Hz, 1H), 7.51 (d, J=8.6 Hz, 1H), 7.44 (dd, J=8.6, 2.9 Hz, 1H), 7.39 (d, J=8.3 Hz, 1H), 7.09 (d, J=10.0 Hz, 1H), 5.25 (s, 2H), 4.85 (s, 2H), 3.83 (s, 3H), 3.63 (s, 3H). $^{19}$F NMR (282 MHz, DMSO-$d_6$) −141.33. Tr(MET-uHPLC-002)=2.92 min m/z (ES+) (M+H)+ 397.0, 99%.

Method 13

Scheme for Method 13

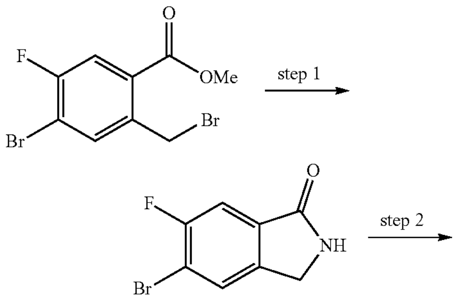

-continued

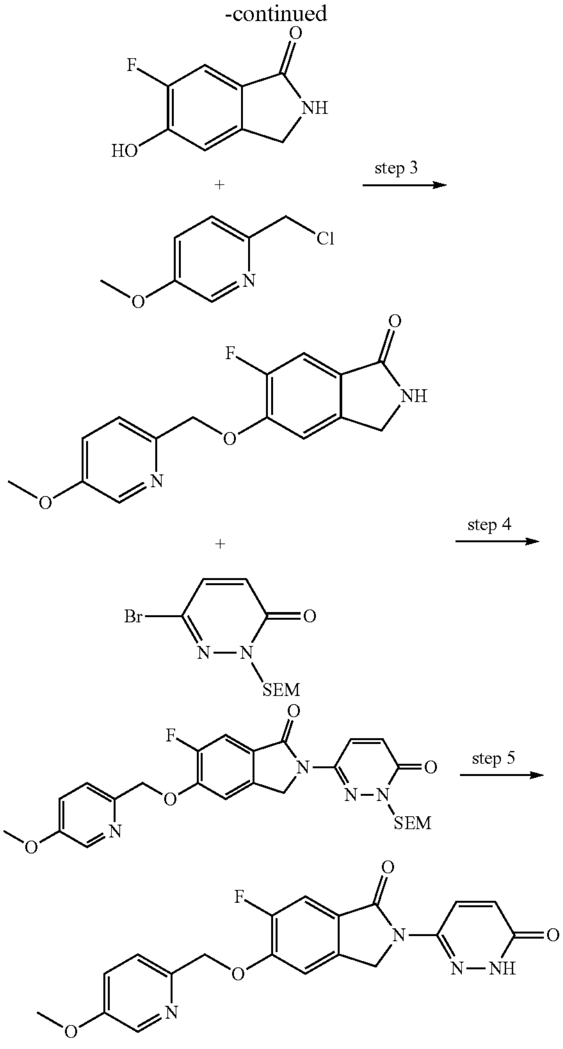

Example 13-1

Step 1: 5-Bromo-6-fluoroisoindolin-1-one

Ammonia gas was bubbled into a solution of methyl 4-bromo-2-(bromomethyl)-5-fluorobenzoate (330 mg, 1.01 mmol) in MeOH (10 mL) at rt until saturated, and the mixture was stirred overnight. After this time, the volatiles were removed under reduced pressure, and the residue obtained was suspended in 1:1 MeOH/water and filtered. The solid obtained was washed with water and dried under vacuum to afford the title compound (217 mg, 93%). $^1$H NMR (300 MHz, DMSO-$d_6$) 8.81 (s, 1H), 7.99 (d, J=5.9 Hz, 1H), 7.61 (d, J=7.6 Hz, 1H), 4.36 (s, 2H).

Step 2: 6-Fluoro-5-hydroxyisoindolin-1-one

To a mixture of 5-bromo-6-fluoroisoindolin-1-one (210 mg, 0.913 mmol), bis(pinacolato)diboron (348 mg, 1.37 mmol) and potassium acetate (224 mg, 2.28 mmol) in 1,4-dioxane (20 mL) was added Pd(dppf)$Cl_2$ (33 mg, 0.046 mmol), and the mixture was heated at 100° C. for 18 h. After this time, the mixture was cooled to rt, and a solution of sodium perborate tetrahydrate (351 mg, 2.28 mmol) in water (6 mL) was added. The mixture was stirred for 2 h, and concentrated under vacuum. The residue obtained was purified by FCC (silica, 0-20% MeOH in EtOAc) to afford the title compound (107 mg, 70%). $^1$H NMR (300 MHz, DMSO-$d_6$) 10.58 (s, 1H), 8.36 (s, 1H), 7.36 (d, J=9.9 Hz, 1H), 7.09 (d, J=7.5 Hz, 1H), 4.24 (s, 2H).

Step 3: 6-Fluoro-5-((5-methoxypyridin-2-yl)methoxy)isoindolin-1-one

To a mixture of 6-fluoro-5-hydroxyisoindolin-1-one (100 mg, 0.598 mmol) and potassium carbonate (248 mg, 1.79 mmol) in DMF (10 mL) at rt was added 2-(chloromethyl)-5-methoxypyridine hydrochloride (174 mg, 0.897 mmol), and the mixture was heated at 60° C. overnight. After this time, the solvent was removed under reduced pressure, and the residue obtained was purified by FCC (silica, 0-100% MeOH in EtOAc) to afford the title compound (85 mg, 49%). $^1$H NMR (300 MHz, DMSO-$d_6$) 8.50 (s, 1H), 8.31 (d, J=2.2 Hz, 1H), 7.53-7.40 (m, 4H), 5.24 (s, 2H), 4.30 (s, 2H), 3.84 (s, 3H). MS ($ES^+$) $(M+H)^+$ 289.

Step 4: 6-Fluoro-54(5-methoxypyridin-2-yl)methoxy)-2-(6-oxo-1-((2-(trimethylsilyl)ethoxy)methyl)-1,6-dihydropyridazin-3-yl)isoindolin-1-one To a mixture of 6-fluoro-5-((5-methoxypyridin-2-yl)methoxy)isoindolin-1-one (80 mg, 0.28 mmol), 3-bromo-6-((2-(trimethylsilyl)ethoxy)methoxy)pyridazine (0.127 g, 0.416 mmol), RuPhos (0.013 g, 0.028 mmol), and cesium carbonate (0.271 g, 0.833 mmol) in 1,4-dioxane (10 mL) was added $Pd_2(dba)_3$ (0.038 g, 0.042 mmol), and the mixture was heated at 100° C. overnight. After this time, the volatiles were removed under reduced pressure, and the residue obtained was purified by FCC (silica, 0-100% EtOAc in hexanes) to afford 6-fluoro-5-((5-methoxypyridin-2-yl)methoxy)-2-(6-oxo-1-((2-(trimethylsilyl)ethoxy)methyl)-1,6-dihydropyridazin-3-yl)isoindolin-1-one (0.103 g, 72%). $^1$H NMR (300 MHz, DMSO-$d_6$) 8.58 (d, J=10.0 Hz, 1H), 8.32 (d, J=2.4 Hz, 1H), 7.64 (d, J=17.5 Hz, 1H), 7.64 (s, 1H), 7.55 (d, J=8.5 Hz, 1H), 7.47 (dd, J=8.5, 2.9 Hz, 1H), 7.13 (d, J=10.0 Hz, 1H), 5.31 (s, 2H), 5.29 (s, 2H), 4.85 (s, 2H), 3.84 (s, 3H), 3.69 (t, J=15.9 Hz, 2H), 0.88 (t, J=7.8 Hz, 2H), −0.024 (s, 9H). MS ($ES^+$) $(M+H)^+$ 513.

Step 5: 6-Fluoro-5-((5-methoxypyridin-2-yl)methoxy)-2-(6-oxo-1,6-dihydropyridazin-3-yl)isoindolin-1-one A mixture of TFA (2.00 mL, 26.9 mmol) and 6-fluoro-5-((5-methoxypyridin-2-yl)methoxy)-2-(6-oxo-1-((2-(trimethylsilyl)ethoxy)methyl)-1,6-dihydropyridazin-3-yl)isoindolin-1-one (103 mg, 0.201 mmol) was stirred at rt for 30 min. After this time, the volatiles were removed under vacuum, and the residue obtained was purified by prep HPLC (MeCN-water, 0.1% v/v formic acid). The product obtained was repurified by FCC (silica, 0-20% MeOH in EtOAc) to afford the title compound (44 mg, 57%).

Example 13-1: 6-Fluoro-5-((5-methoxypyridin-2-yl)methoxy)-2-(6-oxo-1,6-dihydropyridazin-3-yl)isoindolin-1-one $^1$H NMR (500 MHz, DMSO-$d_6$) 12.78 (br s, 1H), 8.53 (d, J=10.2 Hz, 1H), 8.31 (d, J=2.8 Hz, 1H), 7.65-7.60 (m, 2H), 7.54 (d, J=8.5 Hz, 1H), 7.46 (dd, J=8.6, 2.9 Hz, 1H), 7.02 (d, J=10.1 Hz, 1H), 5.29 (s, 2H), 4.85 (s, 2H), 3.84 (s, 3H). $^{19}$F NMR (282 MHz, DMSO-$d_6$) −133.41. Tr(MET-uHPLC-002)=2.94 min, ($ES^+$) $(M+H)^+$ 383.1, 98%.

The following additional compounds were prepared by Method 13:

Example 13-2: 5-Fluoro-6-[(5-methoxy-2-pyridyl)methoxy]-2-(6-oxo-1H-pyridazin-3-yl)isoindolin-1-one

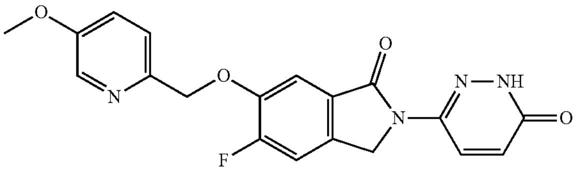 [SMILES: COc1ccc(COc2cc3c(cc2F)CN(c2ccc(=O)[nH]n2)C3=O)nc1]

$^1$H NMR (500 MHz, DMSO-$d_6$) 12.87 (s, 1H), 8.51 (d, J=10.2 Hz, 1H), 8.30 (d, J=2.8 Hz, 1H), 7.51 (d, J=8.6 Hz, 1H), 7.43 (dd, J=8.6, 2.9 Hz, 1H), 7.30 (dd, J=10.6, 1.9 Hz, 1H), 7.27 (d, J=2.0 Hz, 1H), 7.05 (d, J=10.2 Hz, 1H), 5.24 (s, 2H), 4.91 (s, 2H), 3.84 (s, 3H). 19F NMR (471 MHz, DMSO-$d_6$) −117.76 (d, J=10.5 Hz). Tr(MET-uHPLC-AB-101)=2.21 min m/z (ES+)(M+H)+ 383.2, 98%.

Example 13-3: 4-Fluoro-6-[(5-methoxy-2-pyridyl)methoxy]-2-(6-oxo-1H-pyridazin-3-yl)isoindolin-1-one

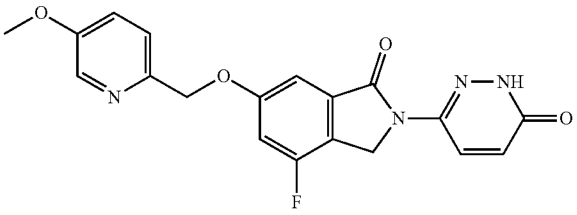 [SMILES: COc1ccc(COc2cc(F)c3c(c2)C(=O)N(c2ccc(=O)[nH]n2)C3)nc1]

$^1$H NMR (400 MHz, DMSO-$d_6$) 12.87 (s, 1H), 8.51 (d, J=10.2 Hz, 1H), 8.30 (d, J=2.8 Hz, 1H), 7.51 (d, J=8.6 Hz, 1H), 7.43 (dd, J=8.6, 2.9 Hz, 1H), 7.32-7.23 (m, 2H), 7.05 (d, J=10.2 Hz, 1H), 5.24 (s, 2H), 4.91 (s, 2H), 3.84 (s, 3H). 19F NMR (376 MHz, DMSO-$d_6$) −117.76. Tr(MET-uHPLC-AB-101)=2.26 min m/z (ES+)(M+H)+ 383.2, 100%.

Method 14

Scheme for Method 14

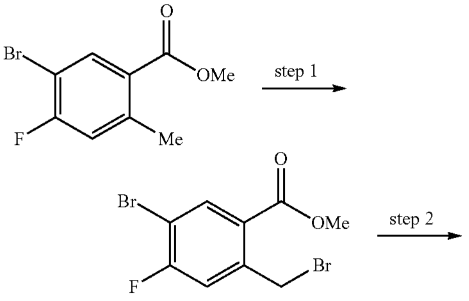

-continued

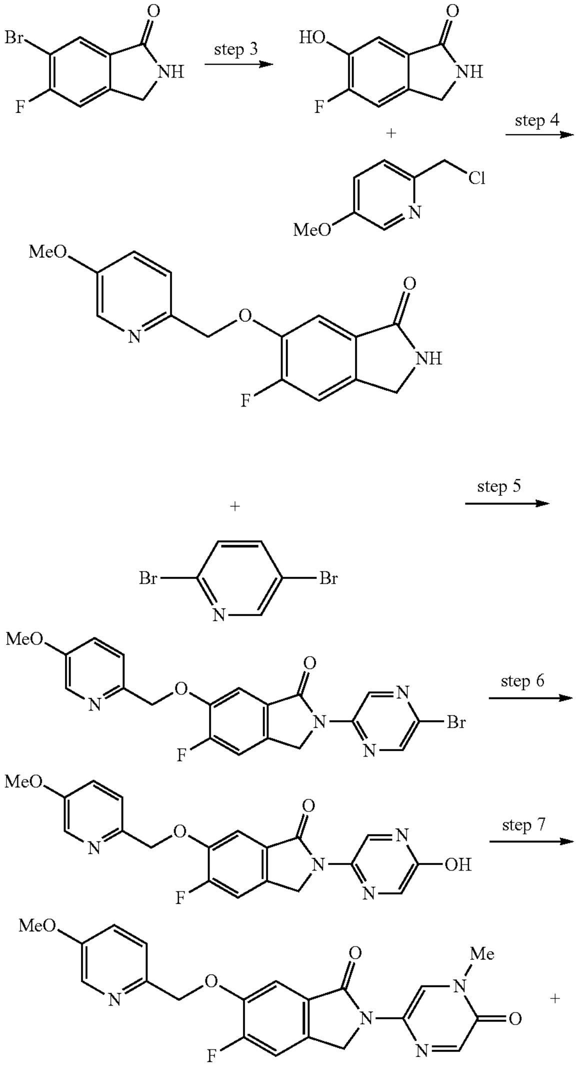

Example 14-1

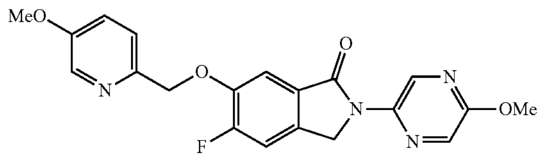

Example 14-2

Step 1: Methyl 5-bromo-2-(bromomethyl)-4-fluorobenzoate

To a solution of methyl 5-bromo-4-fluoro-2-methylbenzoate (400 mg, 1.62 mmol) in carbon tetrachloride (15 mL) was added NBS (288 mg, 1.62 mmol) and AIBN (5.3 mg, 0.032 mmol), and the mixture was stirred at 80° C. overnight. After this time, the volatiles were removed under reduced pressure, and the residue obtained was purified by FCC (silica, 0-5% EtOAc in hexanes) to afford the title compound (487 mg, 92%). $^1$H NMR (300 MHz, $CDCl_3$) 8.23 (d, J=7.0 Hz, 1H), 7.26 (d, J=8.7 Hz, 1H), 4.89 (s, 2H), 3.94 (s, 3H).

Step 2: 6-Bromo-5-fluoroisoindolin-1-one

To a solution of methyl 5-bromo-2-(bromomethyl)-4-fluorobenzoate (172 mg, 0.528 mmol) in MeOH (6 mL) was added 7 N ammonia in MeOH (0.45 mL, 3.2 mmol), followed by ammonium hydroxide (2 mL, 0.53 mmol), and the mixture was stirred at rt for 18 h. After this time, the volatiles were removed under reduced pressure. The residue obtained was suspended in water (15 mL), and the mixture was neutralized with 1 N HCl. The resulting solids were collected by filtration and dried under high vacuum to afford the title compound (119 mg, 98%). $^1$H NMR (300 MHz, $CDCl_3$) 8.08 (d, J=6.3 Hz, 1H), 7.25 (d, J=8.4 Hz, 1H), 6.51 (br s, 1H), 4.42 (s, 2H).

Step 3: 5-Fluoro-6-hydroxyisoindolin-1-one

A mixture of 6-bromo-5-fluoroisoindolin-1-one (118 mg, 0.513 mmol), bis(pinacolato)diboron (195 mg, 0.768 mmol), and potassium acetate (126 mg, 1.28 mmol) in 1,4-dioxane (7 mL) was purged with nitrogen for 2 min. Pd(dppf)$Cl_2$ (38 mg, 0.051 mmol) was added, and the reaction mixture was heated in a sealed tube at 100° C. for 1.5 h. After this time, the mixture was cooled to rt and concentrated to dryness under reduced pressure. The residue obtained was suspended in THF (5.0 mL) and water (5.0 mL), sodium perborate tetrahydrate (197 mg, 1.28 mmol) was added, and the mixture was stirred at rt for 30 min. After this time, aqueous ammonium chloride (5 mL) was added. The volatiles were removed under reduced pressure, and the residue obtained was purified by FCC (silica, 0-20% MeOH in EtOAc) to afford the title compound (66 mg, 62%). MS (ES$^+$) (M+H)$^+$ 168.

Step 4: 5-Fluoro-6-((5-methoxypyridin-2-yl)methoxy)isoindolin-1-one

Potassium carbonate (133 mg, 0.962 mmol) was added to a solution of 5-fluoro-6-hydroxyisoindolin-1-one (66 mg, 0.32 mmol) and 2-(chloromethyl)-5-methoxypyridine (71 mg, 0.45 mmol) in DMF (5 mL), and the mixture was stirred at 70° C. for 2 h. After this time, the mixture was cooled to rt, and the solvents were removed under reduced pressure. The residue obtained was purified by FCC (silica, 0-20% MeOH in EtOAc, then 0-20% MeOH in DCM) to afford the title compound (85 mg, 92%). $^1$H NMR (300 MHz, DMSO-$d_6$) 8.56 (s, 1H), 8.30 (d, J=2.1 Hz, 1H), 7.50-7.42 (m, 4H), 5.25 (s, 2H), 4.28 (s, 2H), 3.83 (s, 3H). MS (ES$^+$) (M+H)$^+$ 289.

Step 5: 2-(5-Bromopyrazin-2-yl)-5-fluoro-6-((5-methoxypyridin-2-yl)methoxy)isoindolin-1-one A mixture of 5-fluoro-6-((5-methoxypyridin-2-yl)methoxy)isoindolin-1-one (84 mg, 0.29 mmol), 2,5-dibromopyrazine (83 mg, 0.35 mmol), Xantphos (15 mg, 0.026 mmol), and cesium carbonate (285 mg, 0.875 mmol) in 1,4-dioxane (10 mL) was purged with nitrogen for 2 min. $Pd_2(dba)_3$ (8 mg, 0.009 mmol) was added, and the reaction mixture was heated in a sealed vial at 120° C. for 4 h. After this time, the mixture was cooled to rt and concentrated under reduced pressure. The residue obtained was purified by FCC (silica, 0-100% EtOAc in DCM, then 0-10% MeOH in DCM) to afford the title compound (53 mg, 41%). $^1$H NMR (300 MHz, DMSO-$d_6$) 9.52 (s, 1H), 8.73 (s, 1H), 8.32 (d, J=2.7 Hz, 1H), 7.67 (d, J=4.2 Hz, 1H), 7.64 (s, 1H), 7.53 (d, J=9.0 Hz, 1H), 7.45 (dd, J=8.7, 3.0 Hz, 1H), 5.32 (s, 2H), 4.96 (s, 2H), 3.84 (s, 3H). MS (ES$^+$) (M+H)$^+$ 445.

Step 6: 5-Fluoro-2-(5-hydroxypyrazin-2-yl)-6-((5-methoxypyridin-2-yl)methoxy)isoindolin-1-one A mixture of 2-(5-bromopyrazin-2-yl)-5-fluoro-6-((5-methoxypyridin-2-yl)methoxy)isoindolin-1-one (52 mg, 0.12 mmol), tBuXPhos (5.9 mg, 0.014 mmol), and freshly ground KOH (13 mg, 0.23 mmol) in 1,4-dioxane (1.5 mL) and water (1.5 mL) was purged with nitrogen for 2 min. $Pd_2(dba)_3$ (6.4 mg, 0.0070 mmol) was added, and the reaction mixture was heated in a sealed vial at 100° C. for 2 h. After this time, the mixture was cooled to rt, neutralized with 1 N HCl, and concentrated to dryness under reduced pressure. The residue obtained was purified by FCC (silica, 0-20% MeOH in EtOAc) to afford the title compound (11 mg, 25%). $^1$H NMR (300 MHz, DMSO-$d_6$) 8.81 (br s, 1H), 8.31 (d, J=2.7 Hz, 1H), 7.98 (s, 1H), 7.63-7.56 (m, 2H), 7.52 (d, J=8.4 Hz, 1H), 7.44 (dd, J=8.5, 2.7 Hz, 1H), 5.30 (s, 2H), 4.91 (s, 2H), 3.84 (s, 3H). MS (ES$^+$) (M+H)$^+$ 383.

Step 7: 5-Fluoro-6-((5-methoxypyridin-2-yl)methoxy)-2-(4-methyl-5-oxo-4,5-dihydropyrazin-2-yl)isoindolin-1-one and 5-fluoro-2-(5-methoxypyrazin-2-yl)-6-((5-methoxypyridin-2-yl)methoxy)isoindolin-1-one Methyl 4-nitrobenzenesulfonate (8 mg, 0.04 mmol) was added to a mixture of potassium carbonate (11 mg, 0.078 mmol) and 5-fluoro-2-(5-hydroxypyrazin-2-yl)-6-((5-methoxypyridin-2-yl)methoxy)isoindolin-1-one (10 mg, 0.029 mmol) in DMF (2 mL), and the mixture was stirred at rt for 16 h. After this time, the reaction mixture was concentrated to dryness under reduced pressure, and the residue obtained was absorbed onto silica gel and purified by FCC (silica, 0-15% MeOH in EtOAc) to afford 5-fluoro-6-((5-methoxypyridin-2-yl)methoxy)-2-(4-methyl-5-oxo-4,5-dihydropyrazin-2-yl)isoindolin-1-one (5 mg, 48%), and 5-fluoro-2-(5-methoxypyrazin-2-yl)-6-((5-methoxypyridin-2-yl)methoxy)isoindolin-1-one (5 mg, 48%).

Example 14-1: 5-Fluoro-6-((5-methoxypyridin-2-yl)methoxy)-2-(4-methyl-5-oxo-4,5-dihydropyrazin-2-yl)isoindolin-1-one $^1$H NMR (500 MHz, $CDCl_3$) 8.61 (d, J=1.0 Hz, 1H), 8.32 (d, J=2.5 Hz, 1H), 8.04 (d, J=1.5 Hz, 1H), 7.53 (d, J=7.5 Hz, 1H), 7.48 (d, J=8.5 Hz, 1H), 7.26 (m, 1H), 7.24 (dd, J=8.5, 3.0 Hz, 1H), 5.28 (s, 2H), 4.88 (s, 2H), 3.87 (s, 3H), 3.62 (s, 3H). $^{19}$F NMR (282 MHz, $CDCl_3$) −124.82. Tr(MET-uHPLC-001)=2.90 min (ES$^+$) (M+H)$^+$ 397.2, 97%.

Example 14-2: 5-Fluoro-2-(5-methoxypyrazin-2-yl)-6-((5-methoxypyridin-2-yl)-methoxy)isoindolin-1-one $^1$H NMR (500 MHz, DMSO-$d_6$) 9.23 (d, J=1.0 Hz, 1H), 8.31 (d, J=3.0 Hz, 1H), 8.22 (d, J=1.5 Hz, 1H), 7.63-7.59 (m, 2H), 7.52 (d, J=9.0 Hz, 1H), 7.45 (dd, J=8.5, 3.0 Hz, 1H), 5.31 (s, 2H), 4.95 (s, 2H), 3.93 (s, 3H), 3.84 (s, 3H). $^{19}$F NMR (282 MHz, DMSO-$d_6$) −126.16. Tr(MET-uHPLC-001)=3.56 min, (ES$^+$) (M+H)$^+$ 397.0, 98%.

The following additional compounds were prepared by Method 14:

Example 14-3: 6-Fluoro-5-((5-methoxypyridin-2-yl) methoxy)-2-(4-methyl-5-oxo-4,5-dihydropyrazin-2-yl)isoindolin-1-one

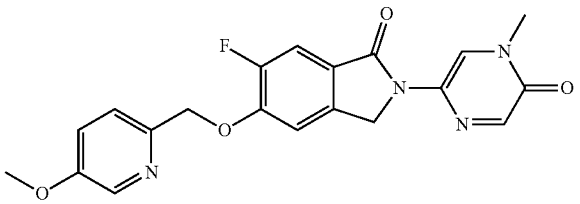 [SMILES: COc1ccc(COc2cc3c(cc2F)C(=O)N(c2cn(C)c(=O)cn2)C3)nc1]

$^1$H NMR (500 MHz, DMSO-$d_6$) 8.53 (d, J=1.1 Hz, 1H), 8.31 (d, J=2.8 Hz, 1H), 8.00 (d, J=1.1 Hz, 1H), 7.63 (d, J=7.3 Hz, 1H), 7.61 (d, J=9.8 Hz, 1H), 7.54 (d, J=8.5 Hz, 1H), 7.46 (dd, J=8.5, 2.9 Hz, 1H), 5.28 (s, 2H), 4.90 (s, 2H), 3.84 (s, 3H), 3.54 (s, 3H). $^{19}$F NMR (282 MHz, DMSO-$d_6$) −133.49. Tr(MET-uHPLC-006)=4.02 min m/z (ES+) (M+H)+ 397.0, 97%.

Biological Assays

Exon1-Q46 Radioligand Binding Assay

For radioligand binding assays (RBA) MBP-HTT(1-89) Q46-His(6×) ("Exon1-Q46") protein was generated based on a previous publication (Scherzinger et al. Cell, Vol. 90, 549-558, Aug. 8, 1997). For experiments 30 μM MBP-Exon1-Q46 was incubated with 150 μg/mL thrombin in assay buffer (150 mM NaCl, 50 mM Tris pH 8.0) and 2 mM $CaCl_2$ for 16 hours at 37° C. Aggregated Exon1-Q46 was pelleted by centrifugation for 5 minutes at 13,000 rpm in a bench top centrifuge and re-dissolved in the same volume of assay buffer. Test compounds were prepared by titration in DMSO at 11 concentrations from 63 μM to 2 nM. For the RBA, Exon1-Q46 protein aggregates and test compounds were pre-incubated in assay buffer for 20 minutes at room temperature, in 100 μL/well in a 96-well plate (pp, round bottom). Then, ligand was added in 50 μL/well and incubated for 60 minutes at 37° C. Final assay concentrations were 1 μM to 30 pM test compound, 1 μM Exon1-Q46 protein (equivalent monomer concentration) and 0.3 nM ligand [$^3H_3$-methyl]-5-((5-methoxypyridin-2-yl)methoxy)-2-(pyrazin-2-yl)benzo[d]oxazole. Samples were transferred onto GF/B filter plates and washed 2× with 200 μL PBS using a Filtermate Harvester. After drying filter plates for 1 hour at 55° C., the back of the plates were sealed with foil and 30 μL/well scintillation fluid (Packard MicroScint 40) added, incubated for 15 minutes in the dark and counted in a MicroBeta reader. For analysis, replicate data from independent assay plates were normalized towards 0% and 100% inhibition using control wells of vehicle (0% inhibition) and 1 μM unlabelled [$^3H_3$-methyl]-5-((5-methoxypyridin-2-yl) methoxy)-2-(pyrazin-2-yl)benzo[d]oxazole (100% inhibition). $IC_{50}$ values were determined with a sigmoidal inhibition model with four variables (top, bottom, slope, $IC_{50}$) in a global fit using the normalized replicate data.

The results for various example compounds were as provided in the table below (+++<100 nM; ++100-500 nM; +>500 nM; ND: not determined):

| Compound No. | Potency Range |
|---|---|
| 1-1 | +++ |
| 1-2 | ND |
| 1-3 | +++ |
| 1-4 | +++ |
| 1-5 | +++ |
| 1-6 | +++ |
| 1-7 | +++ |
| 1-8 | +++ |
| 1-9 | +++ |
| 1-10 | +++ |
| 1-11 | +++ |
| 1-12 | +++ |
| 1-13 | +++ |
| 2-1 | +++ |
| 2-2 | +++ |
| 2-3 | +++ |
| 3-1 | +++ |
| 4-1 | +++ |
| 5-1 | ND |
| 6-1 | +++ |
| 7-1 | ++ |
| 8-1 | +++ |
| 8-2 | +++ |
| 9-1 | +++ |
| 9-2 | +++ |
| 9-3 | +++ |
| 10-1 | +++ |
| 10-2 | +++ |
| 11-1 | +++ |
| 12-1 | +++ |
| 12-2 | +++ |
| 12-3 | +++ |
| 12-4 | +++ |
| 12-5 | +++ |
| 12-6 | +++ |
| 12-7 | +++ |
| 12-8 | +++ |
| 12-9 | +++ |
| 12-10 | +++ |
| 13-1 | +++ |
| 13-2 | +++ |
| 13-3 | +++ |
| 14-1 | +++ |
| 14-2 | +++ |
| 14-3 | +++ |

-continued

PET Imaging Example

The following example provides an illustrative, non-limiting, procedure that may be utilized when performing PET imaging studies on an individual in a clinical setting. The individual is either unmedicated or pre-medicated with an unlabeled compound. The individual may undergo fasting, allowing water intake ad libitum, prior to PET imaging. A 20 G two inch venous catheter is inserted into the contralateral ulnar vein for administration of the imaging agent.

The human subject is positioned in the PET camera and a tracer dose of imaging agent is administered via i.v. catheter. Either arterial or venous blood samples are taken at appropriate time intervals throughout the PET scan in order to analyze and quantitate the fraction of unmetabolized compound in plasma. Images are acquired for up to 120 minutes. Within ten minutes of the injection of radiotracer and at the end of the imaging session, 1 mL blood samples are obtained for determining the plasma concentration of any unlabeled imaging agent compound (or other compound of intervention) which may have been administered before the PET tracer.

Tomographic images are obtained through image reconstruction. For example, for determining the distribution of imaging agent, regions of interest (ROIs) are drawn on the reconstructed image. Regions of interest in a brain image may include, for example, the striatum, cerebellum, or basal ganglia. Imaging agent uptake over time in these regions may be used to generate time activity curves (TAC). Data may be expressed as radioactivity per unit time per unit volume (e.g., μCi/cc/mCi injected dose), or as radioactivity per unit volume. TAC data may be processed with various methods known in the field to yield quantitative parameters, an example of which is Binding Potential (BP). For further description of imaging procedure, see, for example, Waxman A D, et al., Society of Nuclear Medicine Procedure Guideline for FDG PET Brain Imaging, ver. 1.0, (Feb. 8, 2009).

Unbound Brain Fraction

Compounds were tested for unbounded brain fraction (or free fraction in brain, $f_{u,brain}$). It is an accepted standard in the CNS PET imaging field that compounds with low unbound fraction in brain (<5%) likely have high non-specific binding background that is undesirable for the detection of target binding. As a result, $f_{u,brain}$ is an important property in the design of PET ligands for brain imaging [see Zhang et al., Design and selection parameters to accelerate the discovery of novel central nervous system positron emission tomography (PET) ligands and their application in the development of a novel phosphodiesterase 2A PET ligand. *J Med Chem* 2013, 56 (11), 4568-79; Liu et al., Imaging Mutant Huntingtin Aggregates: Development of a Potential PET Ligand. *J Med Chem* 2020, 63 (15), 8608-8633].

| | Compound | Mean Free Brain Fraction (%) |
|---|---|---|
| Comparative Compound 1 | 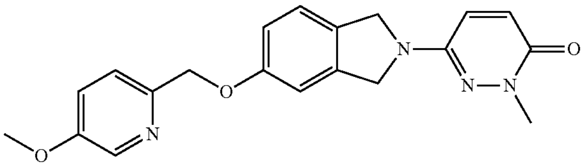 [SMILES: COc1ccc(COc2ccc3c(c2)CN(c2ccc(=O)n(C)n2)C3)nc1] | 1.3 |
| Comparative Compound 2 (Ex 1-4) | 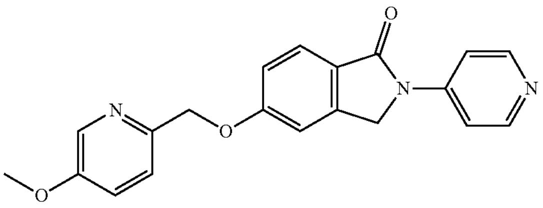 [SMILES: COc1ccc(COc2ccc3c(c2)CN(c2ccncc2)C3=O)nc1] | 3.0 |
| 1-1 | 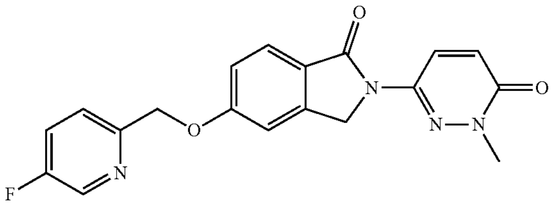 | 12.0 |
| 1-3 | 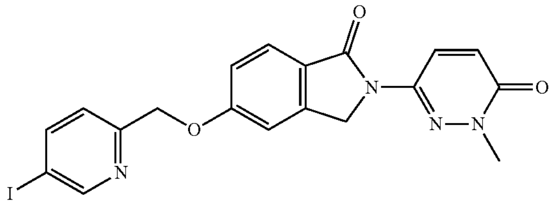 | 1.2 |
| 1-6 | 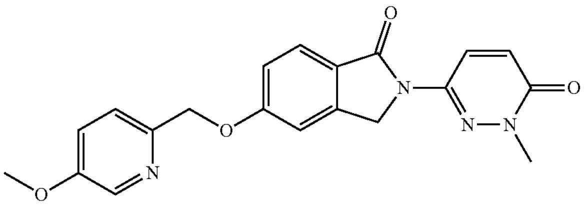 [SMILES: COc1ccc(COc2ccc3c(c2)CN(c2ccc(=O)n(C)n2)C3=O)nc1] | 9.8 |
| 1-7 | 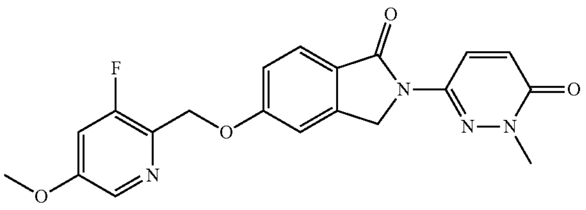 [SMILES: COc1cnc(COc2ccc3c(c2)CN(c2ccc(=O)n(C)n2)C3=O)c(F)c1] | 11.9 |

-continued
| | Compound | Mean Free Brain Fraction (%) |
|---|---|---|
| 1-8 | 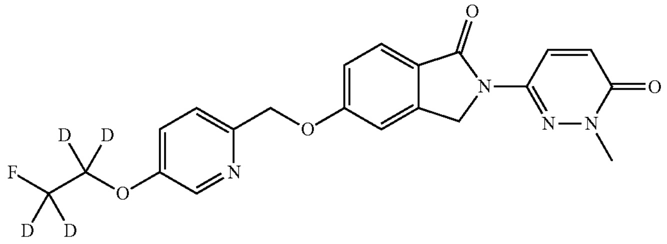 [SMILES: [2H]C([2H])(F)C([2H])([2H])Oc1ccc(COc2ccc3c(c2)CN(c2ccc(=O)n(C)n2)C3=O)nc1] | 10.1 |
| 1-10 | 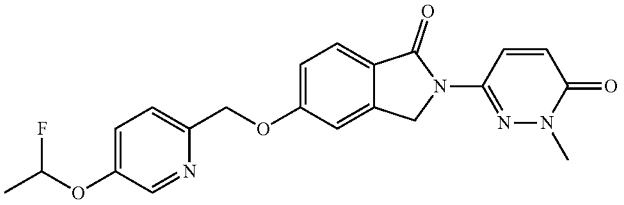 [SMILES: CC(F)Oc1ccc(COc2ccc3c(c2)CN(c2ccc(=O)n(C)n2)C3=O)nc1] | 3.8 |
| 1-11 | 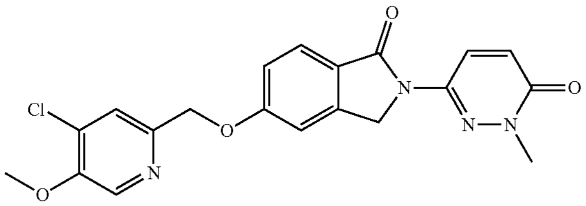 [SMILES: COc1cnc(COc2ccc3c(c2)CN(c2ccc(=O)n(C)n2)C3=O)cc1Cl] | 1.6 |
| 1-12 | 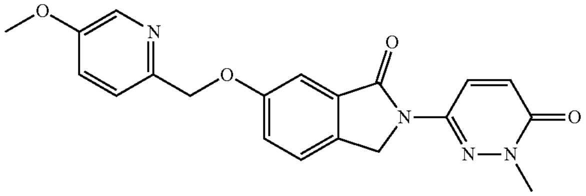 [SMILES: COc1ccc(COc2ccc3c(c2)C(=O)N(c2ccc(=O)n(C)n2)C3)nc1] | 9.0 |
| 1-13 | 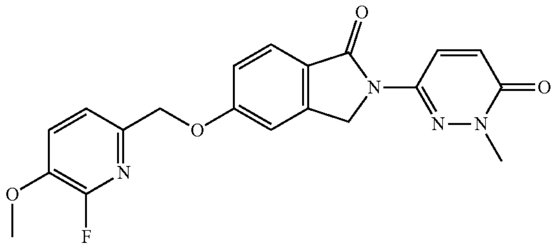 [SMILES: COc1ccc(COc2ccc3c(c2)CN(c2ccc(=O)n(C)n2)C3=O)nc1F] | 7.0 |
| 1-14 | 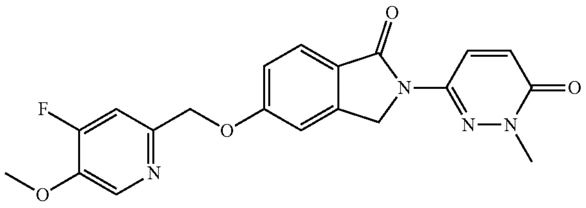 [SMILES: COc1cnc(COc2ccc3c(c2)CN(c2ccc(=O)n(C)n2)C3=O)cc1F] | 12.0 |
| 2-1 | 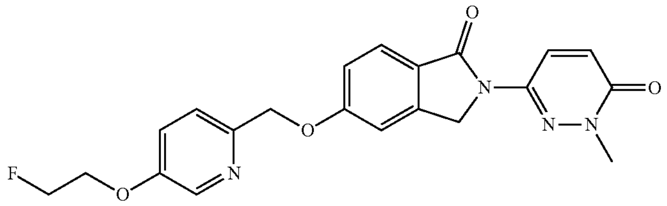 [SMILES: Cn1nc(N2Cc3cc(OCc4ccc(OCCF)cn4)ccc3C2=O)ccc1=O] | 14.3 |

-continued
| | Compound | Mean Free Brain Fraction (%) |
|---|---|---|
| 2-2 | 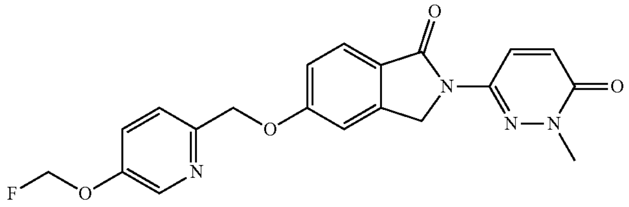 | 12.7 |
| 2-3 | 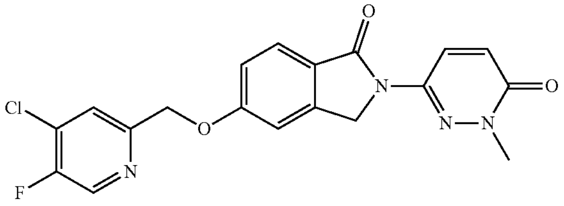 [SMILES: Cn1nc(N2Cc3cc(OCc4cc(Cl)c(F)cn4)ccc3C2=O)ccc1=O] | 2.7 |
| 3-1 | 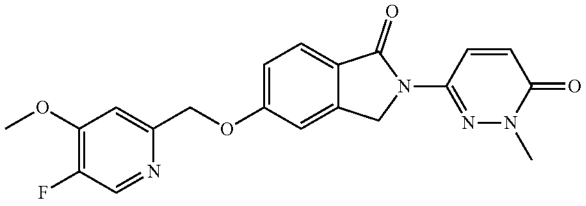 [SMILES: COc1cc(COc2ccc3c(c2)CN(c2ccc(=O)n(C)n2)C3=O)ncc1F] | 9.7 |
| 6-1 | 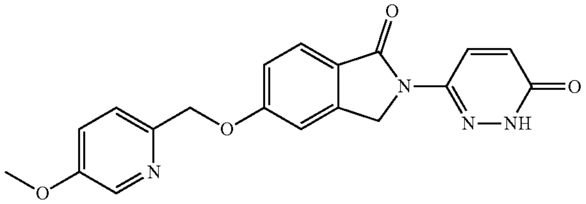 [SMILES: COc1ccc(COc2ccc3c(c2)CN(c2ccc(=O)[nH]n2)C3=O)nc1] | 11.3 |
| 8-1 | 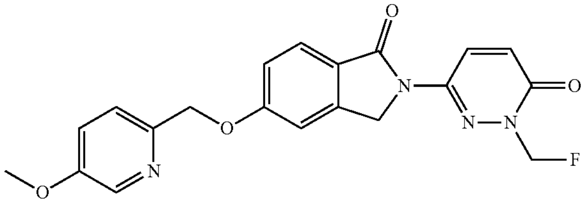 [SMILES: COc1ccc(COc2ccc3c(c2)CN(c2ccc(=O)n(CF)n2)C3=O)nc1] | 7.4 |
| 8-2 | 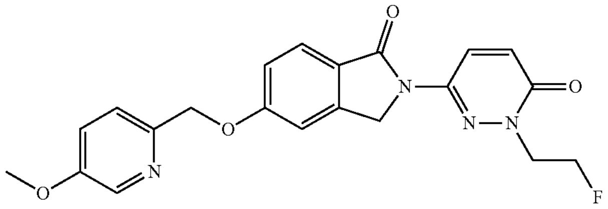 [SMILES: COc1ccc(COc2ccc3c(c2)CN(c2ccc(=O)n(CCF)n2)C3=O)nc1] | 9.0 |
| 9-1 | 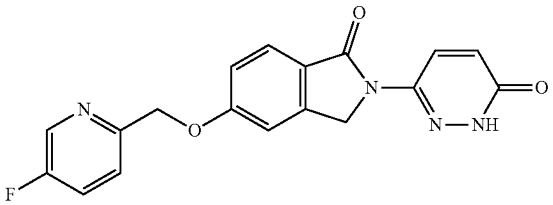 [SMILES: O=C1c2ccc(OCc3ccc(F)cn3)cc2CN1c1ccc(=O)[nH]n1] | 6.7 |

-continued
| | Compound | Mean Free Brain Fraction (%) |
|---|---|---|
| 9-3 | 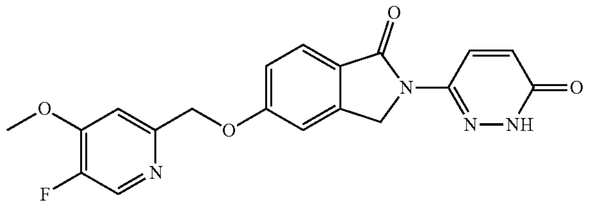 [SMILES: COc1cc(COc2ccc3c(c2)CN(c2ccc(=O)[nH]n2)C3=O)ncc1F] | 5.2 |
| 10-1 | 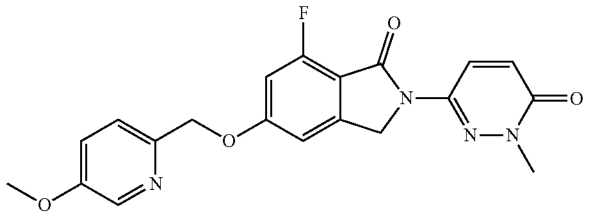 [SMILES: COc1ccc(COc2cc(F)c3c(c2)CN(c2ccc(=O)n(C)n2)C3=O)nc1] | 14.3 |
| 10-2 | 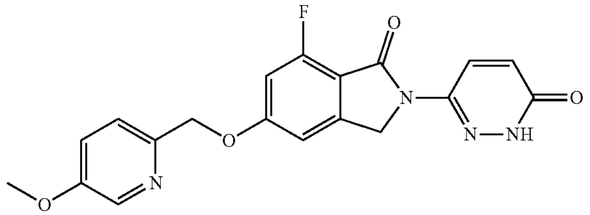 [SMILES: COc1ccc(COc2cc(F)c3c(c2)CN(c2ccc(=O)[nH]n2)C3=O)nc1] | 9.5 |
| 11-1 | 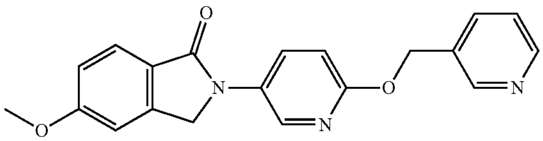 [SMILES: COc1ccc2c(c1)CN(c1ccc(OCc3cccnc3)nc1)C2=O] | 3.2 |
| 12-1 | 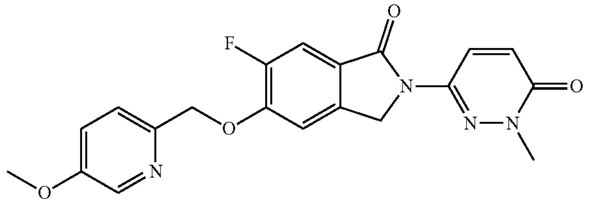 [SMILES: COc1ccc(COc2cc3c(cc2F)C(=O)N(c2ccc(=O)n(C)n2)C3)nc1] | 7.1 |
| 12-2 | 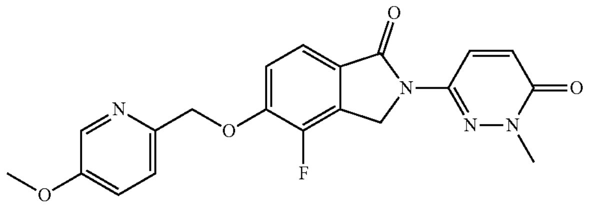 [SMILES: COc1ccc(COc2ccc3c(c2F)CN(c2ccc(=O)n(C)n2)C3=O)nc1] | 5.3 |
| 12-3 | 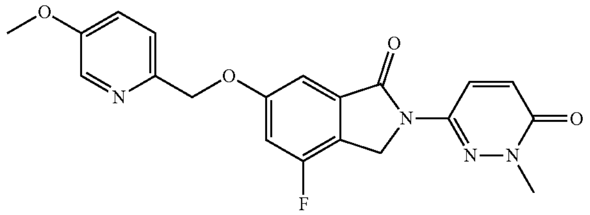 [SMILES: COc1ccc(COc2cc(F)c3c(c2)C(=O)N(c2ccc(=O)n(C)n2)C3)nc1] | 5.4 |

-continued
| | Compound | Mean Free Brain Fraction (%) |
|---|---|---|
| 12-4 | 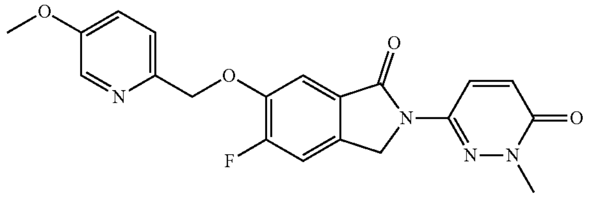 [SMILES: COc1ccc(COc2cc3c(cc2F)CN(c2ccc(=O)n(C)n2)C3=O)nc1] | 9.8 |
| 12-5 | 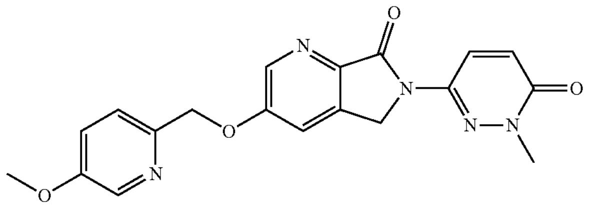 [SMILES: COc1ccc(COc2cnc3c(c2)CN(c2ccc(=O)n(C)n2)C3=O)nc1] | 37.0 |
| 12-6 | 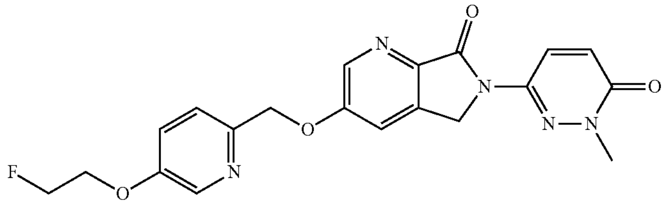 [SMILES: Cn1nc(N2Cc3cc(OCc4ccc(OCCF)cn4)cnc3C2=O)ccc1=O] | 50.0 |
| 12-7 | 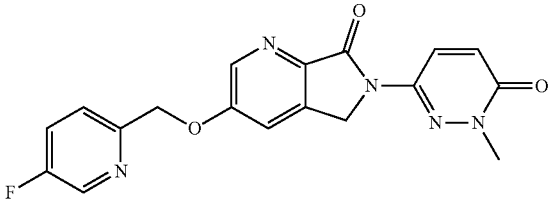 | 67.8 |
| 12-8 | 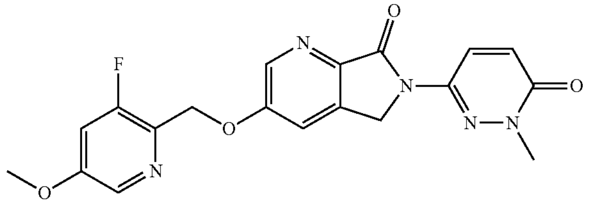 [SMILES: COc1cnc(COc2cnc3c(c2)CN(c2ccc(=O)n(C)n2)C3=O)c(F)c1] | 65.0 |
| 12-10 | 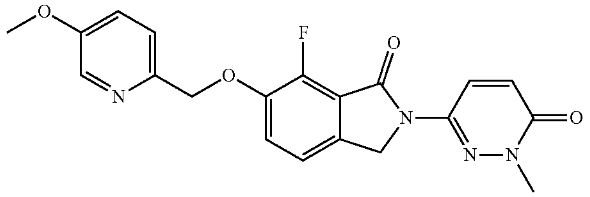 [SMILES: COc1ccc(COc2ccc3c(c2F)C(=O)N(c2ccc(=O)n(C)n2)C3)nc1] | 16.4 |
| 13-1 | 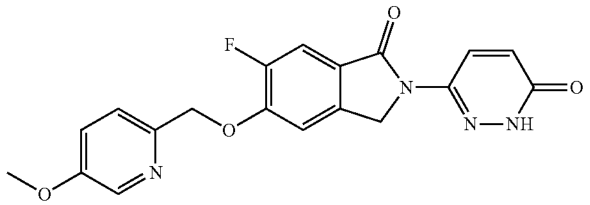 [SMILES: COc1ccc(COc2cc3c(cc2F)C(=O)N(c2ccc(=O)[nH]n2)C3)nc1] | 6.6 |

-continued

| | Compound | Mean Free Brain Fraction (%) |
|---|---|---|
| 13-2 | 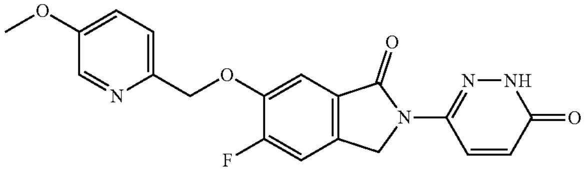 [SMILES: COc1ccc(COc2cc3c(cc2F)CN(c2ccc(=O)[nH]n2)C3=O)nc1] | 6.5 |
| 13-3 | 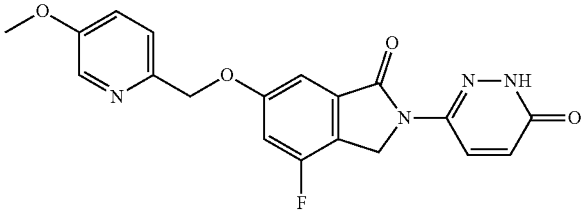 [SMILES: COc1ccc(COc2cc(F)c3c(c2)C(=O)N(c2ccc(=O)[nH]n2)C3)nc1] | 6.2 |
| 14-1 | 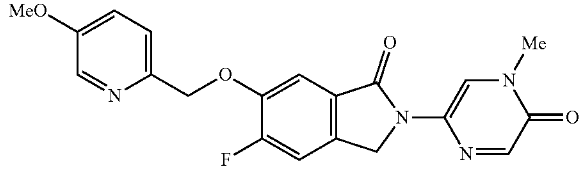 [SMILES: COc1ccc(COc2cc3c(cc2F)CN(c2cn(C)c(=O)cn2)C3=O)nc1] | 15.5 |
| 14-2 | 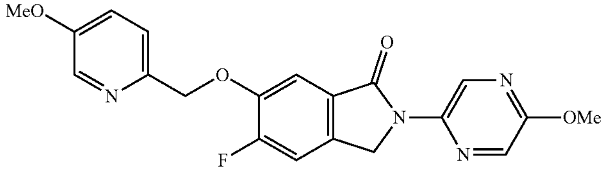 | 0.7 |
| 14-3 | 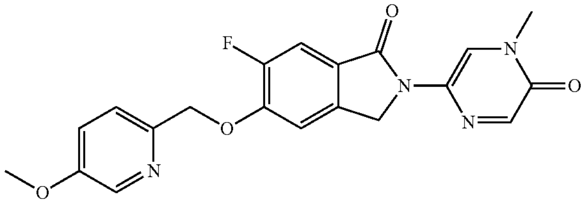 [SMILES: COc1ccc(COc2cc3c(cc2F)C(=O)N(c2cn(C)c(=O)cn2)C3)nc1] | 17.1 |

Determining $f_{u,brain}$ in Mouse Brain by Equilibrium Dialysis. Dialysis membranes (12-14 kDa) (HTDialysis, Connecticut) were soaked in phosphate buffer (10 mM potassium phosphate and 0.8% sodium chloride buffer, pH 7.4 at 37° C.) for a minimum of 1 h, at this time ethanol was added (final concentration of 20% v/v) and membranes continued to soak for 30 min Mouse brain tissue was diluted in phosphate buffer in a 1:4 ratio (w/v) and homogenised using a Precellys 24 (Stretton Scientific, UK) to achieve a final concentration of 20% brain homogenate.

Test compounds prepared as DMSO stocks at 0.5 mM are diluted into brain homogenate to achieve 5 μM final substrate concentration (1% DMSO) and a t=0 sample was prepared by sampling 50 μL of into 400 μL of quench solution (Acetonitrile containing 0.1% formic acid and sulfisoxazole/tolbutamide/imipramine/labetalol 200 nM). Samples were matrix matched with the addition of 50 μL of assay buffer. The HTDialysis Teflon blocks (HTDialysis, Connecticut) were assembled with pre-soaked membrane between each receiver and donor well and clamped in the stainless steel pressure plate (HTDialysis, Connecticut). The lower compartment (acceptor side) was dosed with 120 μL of buffer and the upper compartment (donor side) was dosed with 120 μL of compound in homogenate. All test compounds and controls were completed in triplicate. The HT dialysis plate was sealed and incubated for 6 h at 37° C. shaking at 250 rpm.

Following the incubation, 50 μL of sample was removed from all donor and acceptor wells and transferred into a quench plate containing 400 μL of quench solution. All samples were matrix matched with 50 μL of the alternate blank matrix. Analytical samples were diluted 1:1 with water using the Janus Robot and analysed by LC-MS/MS.

Peak areas of donor and acceptor compartments were compared to determine percent unbound (% $f_u$) and the average of triplicate measurements was reported. Reference T0 sample was used to calculate sample recovery (%). Control compounds were compared with historic and literature values to ensure assay functionality.

When the mean free brain fraction of a compound is less than 5%, undesired promiscuous binding will increase the background signal. Thus, persons of skill in the art understand that a mean free brain fraction of more than 5% is desired for an imaging PET tracer to adequately detect brain structures containing aggregated proteins such as mHTT. The data shows that compounds described herein have higher free brain fraction than the comparative compounds while also providing good binding to mHTT protein species. Thus, compounds described herein have favorable properties for in vivo use as imaging agents.

In Situ Autoradiography (ARG)

In situ autoradiography (ARG) was used to investigate the pharmacological binding characteristics of a tritium-labeled Compound 1-6 ("[$^3$H]-Compound 1-6") in the HD mouse model 12-month-old HOM zQ175 and human post-mortem brains from healthy and HD gene-expanded carriers (HDGECs); specificity of binding was explored by including samples from Alzheimer's disease (AD) patients, which contain other pathological aggregates (e.g., Abeta-containing plaques and phosphor-Tau-expressing tangles). Saturation binding experiments were performed in coronal brain sections; [$^3$H]-Compound 1-6 binding was quantified by densitometric analysis and specific binding was determined in cortex (CTX). Affinity ($K_D$) and maximum number of binding sites ($B_{max}$) were determined for each region of interest (ROI).

than 3 weeks. A similar procedure was conducted with fresh-frozen human post-mortem brain blocks (healthy subjects {CTRL}, Huntingon's disease {HD}, and Alzheimer's disease {AD}).

Assay Procedure

The appropriate number of slides containing the respective tissue sections were acclimated to room temperature for 30 minutes. The slides were then pre-incubated by immersion into 40 mL assay buffer for 20 minutes at room temperature. Following this pre-incubation step, one slide per animal was incubated by immersion into 30 mL of the 10 nM, 3 nM, 1 nM, 0.3 nM, 0.1 nM, 0.03 nM, 0.01 nM, or 0.003 nM Compound 1-6 solutions and one slide was incubated by immersion into 30 mL of 10 nM, 3 nM, 1 nM, 0.3 nM, 0.1 nM, 0.03 nM, 0.01 nM, or 0.003 nM [$^3$H]-Compound 1-6, plus 10 μM unlabeled Compound 1-6 solutions for 60 minutes at room temperature, respectively. A similar paradigm was performed with tritium-labeled Comparative Compound 3 ("[$^3$H]-Comparative Compound 3") and tritium-labeled Comparative Compound 4 ("[$^3$H]-Comparative Compound 4"). Structures of these comparative compounds and compound 1-6 are shown below.

| Compound Number | Structure |
| --- | --- |
| 1-6 | 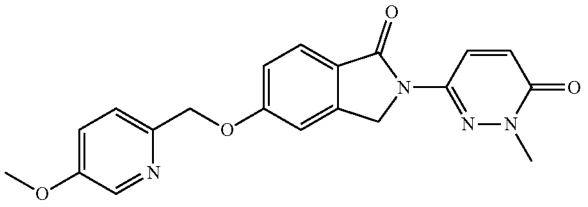 [SMILES: COc1ccc(COc2ccc3c(c2)CN(c2ccc(=O)n(C)n2)C3=O)nc1] |
| Comparative Compound 3 | 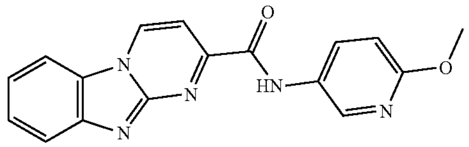 [SMILES: COc1ccc(NC(=O)c2ccn3c(n2)nc2ccccc23)cn1] |
| Comparative Compound 4 | 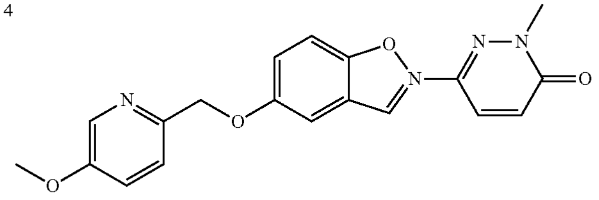 |

Tissue Preparation and Sectioning

At the appropriate ages, HD and WT mice of the different strains were sacrificed by cervical dislocation, and the brains, including cerebellum, were dissected and washed in ice cold PBS. Subsequently, the brains were patted dry on paper towels and transferred into a 6-well plate filled with isopentane that was cooled to a temperature between −30° C. and −40° C. The frozen brains were stored at −80° C. until sectioning.

The non-fixed and non-embedded frozen brains were sectioned by using a cryostat at −18° C. Thereby, serial coronal tissue sections of 20 μm thickness were mounted on superfrost slides and dried at room temperature for approximately 90 minutes. The slides were stored at −80° C. until the different experiments were conducted, but not longer Afterwards, the slides were washed three times for 10 minutes with 200 mL of ice cold washing buffer at 4° C. and dipped for three seconds in ice cold distilled water to remove buffer salts. The slides were dried for three hours at 30° C. and exposed for 96 hours to Fuji BAS-TR 2015 tritium phosphor screens together with the calibrated tritium standards ART 0123C and ART 0123B. Stored radiation energy on the screen was scanned using the phosphorimager Typhoon FLA 7000.

Data Analysis

Densitometric data analysis was performed using the MCID Analysis 7.1 software (Interfocus Imaging Ltd.). Within each brain section, regions of interest (ROI) were defined for STR, CTX, and HPC by using appropriate sample tools, and the software calculated density measures from the gray level values of all pixels within a defined ROI (Molecular dynamics counts per unit area, MDC/$mm^2$). Densitometric calibration related the optical densities to known concentrations of radioactivity from the calibrated tritium standards (fmol/mg tissue) and mean values were calculated for each ROI of the individual brains. Total binding (TB) and non-specific binding (NSB) of the radioligand were quantified, and specific binding (SB) was derived by subtracting NSB from TB (SB=TB−NSB) for each brain and ROI, respectively. Subsequently, the group mean±standard deviation (SD) was calculated for each ROI and experimental condition. The data were fitted to one-site binding equation using non-linear regression method in GraphPad Prism Software.

Saturation Binding: HOM zQ175 HD Mouse Model

As can be seen in FIG. 1, [$^3$H]-Compound 1-6 displayed concentration-dependent specific binding and low nanomolar affinity to mHTT aggregates present in HOM zQ175 brain sections; in the cortex, $K_D$ average values of 1.4 nM were obtained. The calculated $B_{max}$ as a measurement for concentration of specific binding sites reached 448.6 fmol/mg tissue in cortex. It is contemplated that these results are reflective of the amount and density of mHTT aggregates expressed in this region of the brain.

The binding to WT brain sections was minor and only detectable above the lower limit of quantification (LLoQ, 0.5 fmol/mg tissue) at the two highest concentrations investigated, 3 nM and 10 nM. No binding curves could be established and neither $K_D$ nor $B_{max}$ values could be determined, corroborating the specific binding of [$^3$H]-Compound 1-6 to mHTT aggregates expressed only in HOM zQ175 (12-month old) brain sections.

[$^3$H]-Compound 1-6 specific and saturation binding, over a range of radioligand concentrations, determined in cortex and compared to [$^3$H]-Comparative Compound 4 and [$^3$H]-Comparative Compound 3, is further shown in FIG. 1. As is tabulated below, the Bmax of [$^3$H]-Compound 1-6 (448 fmol/mg) was significantly higher compared to [$^3$H]-Comparative Compound 4 (149 fmol/mg) and [$^3$H]-Comparative Compound 3 (169 fmol/mg).

| Test Compound | $K_D$ [nM] | Bmax [fmol/mg] |
|---|---|---|
| Compound 1-6 | 1.4 | 448 |
| Comparative Compound 4 | 0.6 | 149 |
| Comparative Compound 3 | 3.0 | 169 |

It is contemplated that this data suggests that Compound 1-6 is binding to more and/or different mHTT epitopes than Comparative Compound 4 and Comparative Compound 3.

Binding: Human Post-Mortem Brain Sections

Observation of in situ binding from mouse HD model-derived tissue was then extended to post-mortem human brain tissue, to provide information about the general translatability of this mHTT aggregate binder, and specifically with regards to pathology specificity and species-selectivity. [$^3$H]-Compound 1-6 showed mHTT-specific binding in post-mortem human HD brains.

Figure 2:
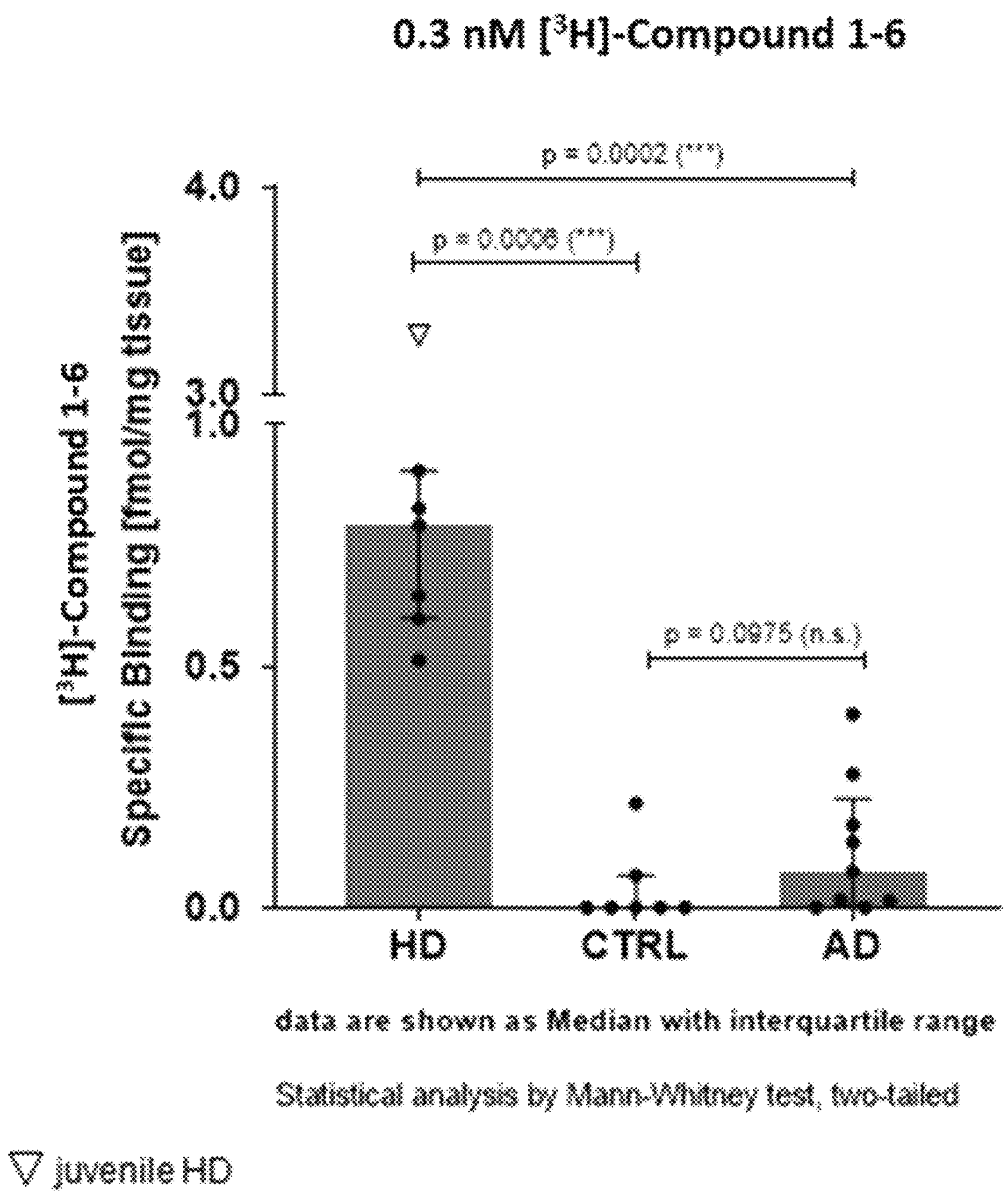
FIG. 2 shows specific binding of [$^3$H]-Compound 1-6 in various samples of post-mortem human brain tissue (healthy subjects [CTRL], Huntingon's disease [HD], and Alzheimer's disease [AD]).

As can be seen in FIG. 2, [$^3$H]-Compound 1-6 showed a low but significantly greater binding to frontal cortical sections from HD donors, compared to CTRL tissue (0.8±0.2 fmol/mg tissue for HD vs. 0.0±0.0 for CTRL; $p<0.01$, comparing HD vs. CTRL). [$^3$H]-Compound 1-6 showed distinct specific binding in gray matter areas with very low white matter binding (≤0.5 fmol/mg tissue). These data are in accordance with the observation that mHTT aggregates are primarily found in cortical neurons (gray matter), and infrequently expressed in white matter.

Further investigation to determine if [$^3$H]-Compound 1-6 shows different binding properties in different forms of the disease was then undertaken. To address this, a juvenile HD sample (one case), in addition to post-mortem adult-onset HD brains, was tested. Juvenile HD is characterized by an early onset and much faster progression compared to adult HD. [$^3$H]-Compound 1-6 displayed the highest binding density to the juvenile HD brain (open triangle in FIG. 2 and FIG. 3), indicating that the compound recognizes mHTT aggregates in both forms of the disease, and may be recognizing additional epitopes expressed in juvenile vs. adult-onset HD brains.

[$^3$H]-Compound 1-6 also showed significantly higher binding in the cortices of HD patients in comparison to brain sections from AD patients (0.1±0.0 fmol/mg tissue; $p<0.01$, comparing HD vs. AD; no significance revealed when comparing CTRL vs. AD), as can be seen in FIG. 2. Low SB of [$^3$H]-Compound 1-6 in cortex from AD patients supports selectivity of this radioligand towards mHTT vs. Aβ and PHF-tau, both of which are expressed in these AD samples (by IHC; data not shown).

Figure 3:
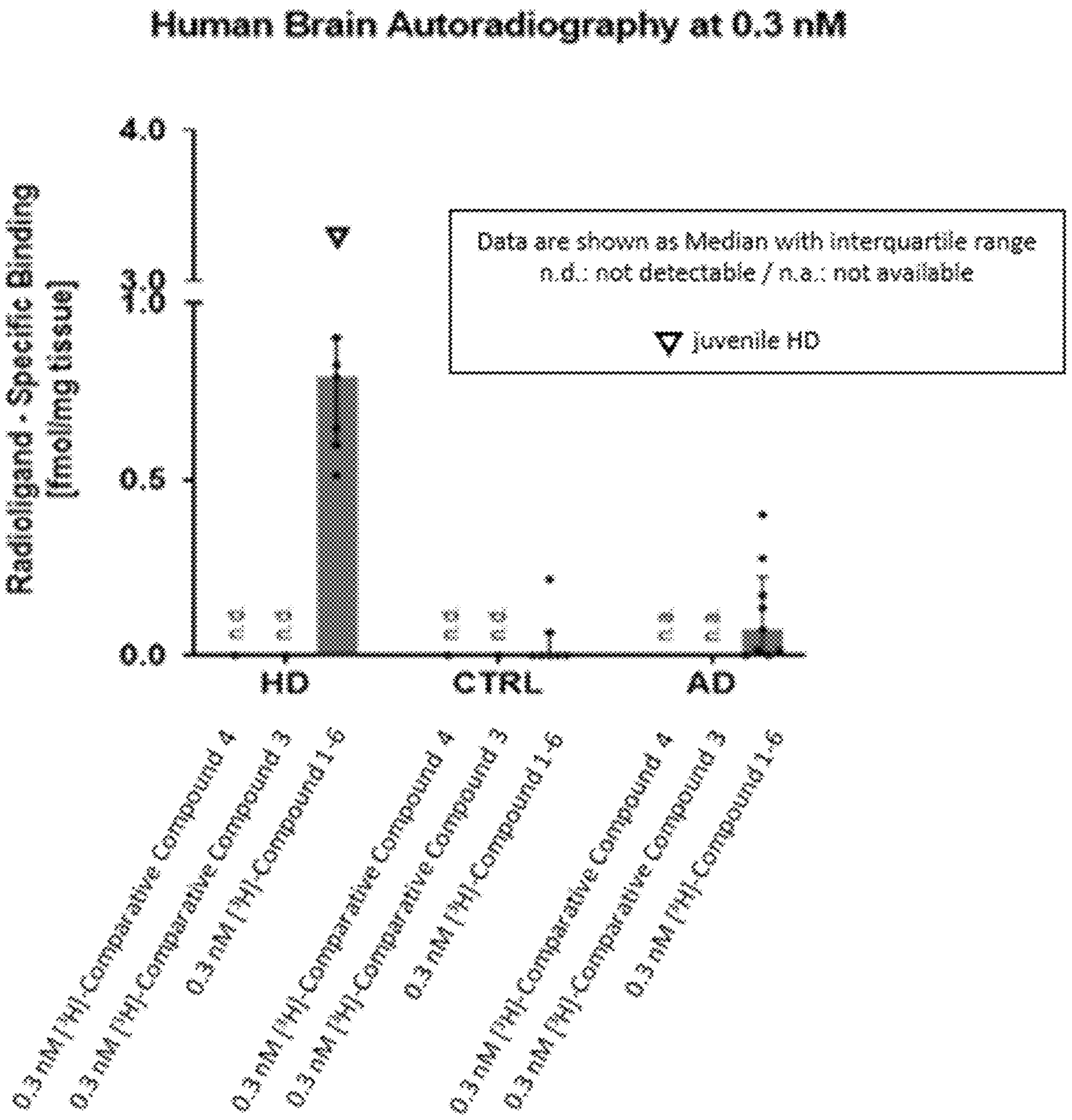
FIG. 3 compares specific binding of [$^3$H]-Compound 1-6 with [$^3$H]-Comparative Compound 3 and [$^3$H]-Comparative Compound 4, in various samples of post-mortem human brain tissue (healthy subjects [CTRL], Huntingon's disease [HD], and Alzheimer's disease [AD]).

As can be seen in FIG. 3, significant specific HD binding was detectable at 0.3 nM [$^3$H]-Compound 1-6, but no HD binding was detectable at 0.3 nM for either [$^3$H]-Comparative Compound 4 or [$^3$H]-Comparative Compound 3, suggesting recognition by [$^3$H]-Compound 1-6 of different binding epitopes and/or greater affinity for mHTT aggregates expressed in HD patient brains compared to [$^3$H]-Comparative Compound 4 or [$^3$H]-Comparative Compound 3 radioligands.

Conclusions

[$^3$H]-Compound 1-6 shows concentration-dependent specific binding to cortex of HOM zQ175 HD mice. Binding to WT brain sections is minor and only detectable above the lower limit of quantification (LLoQ, 0.5 fmol/mg tissue) at the two highest concentrations, 3 nM and 10 nM. [$^3$H]-Compound 1-6 binds to mHTT aggregates in HD mouse brain with low nanomolar affinity, exhibiting $K_D$ values of 1.4 nM which are in accordance with in vitro binding data generated using recombinant Exon1-Q46 protein.

Additionally, [$^3$H]-Compound 1-6 binds selectively to human HD brain sections at 0.3 nM, a concentration of radioligand that failed to reveal HD binding for either [$^3$H]-Comparative Compound 4 or [$^3$H]-Comparative Compound 3, suggesting novel epitope recognition and/or higher affinity binding for Compound 1-6.

Finally, [$^3$H]-Compound 1-6 exhibited selectivity for binding to HD patient brain sections with little to no binding to either healthy control or Alzheimer's disease brain sections.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A compound that is:

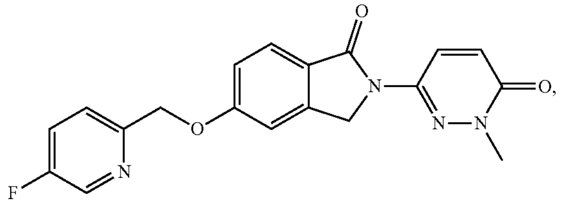

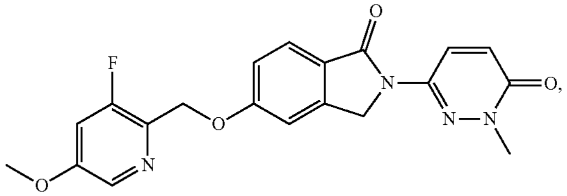

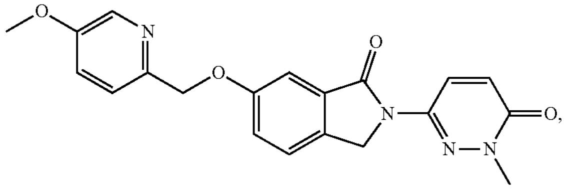

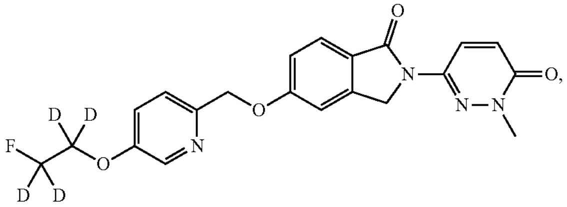

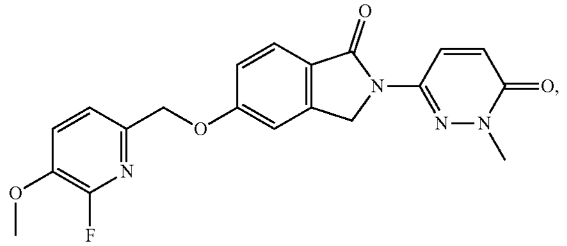

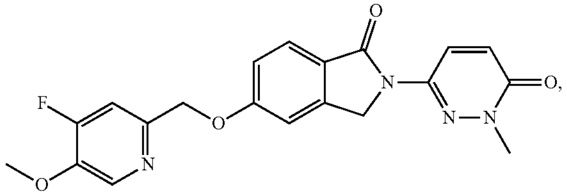

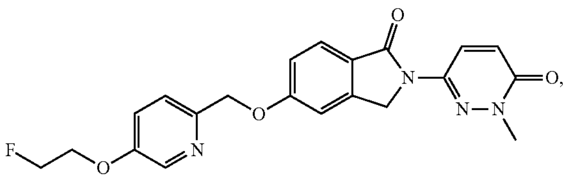

-continued

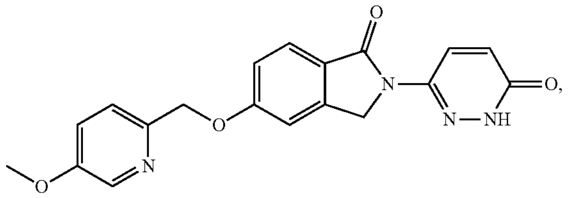

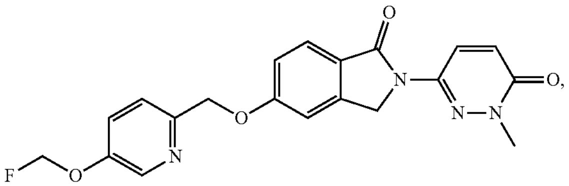

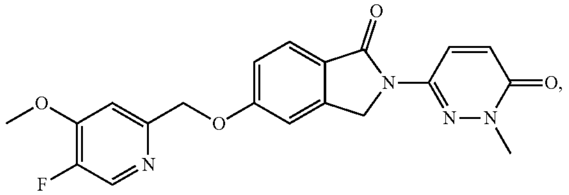

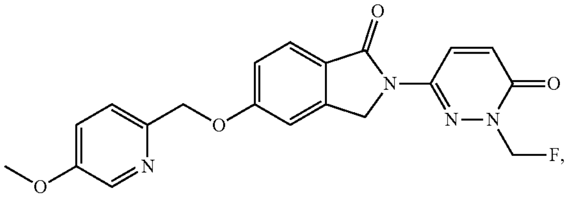

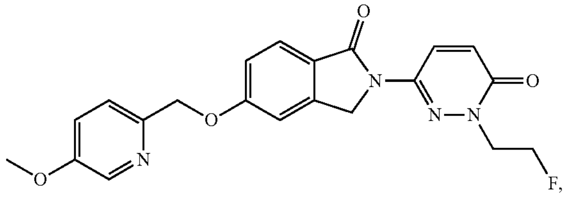

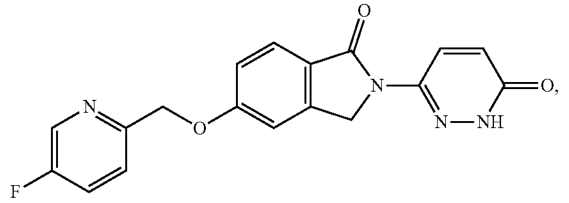

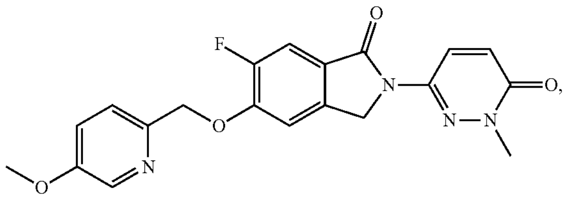

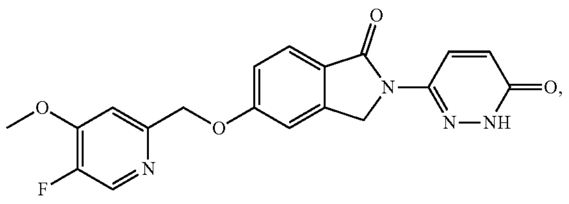

-continued

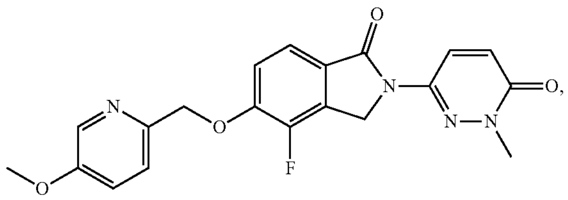

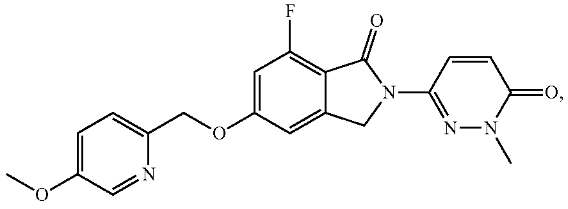

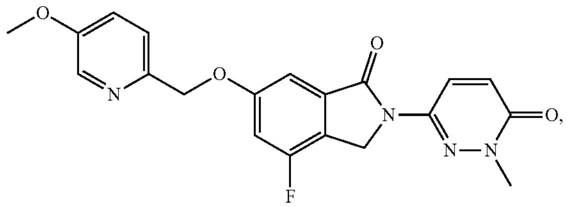

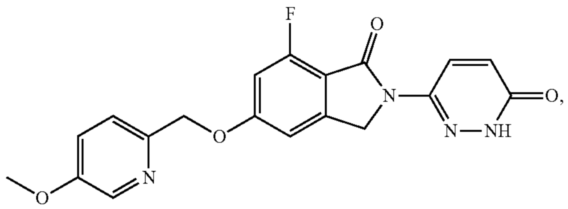

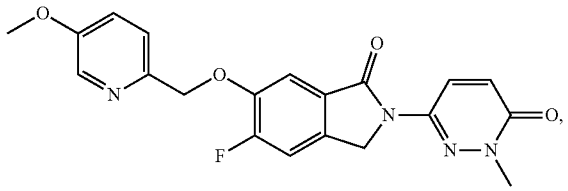

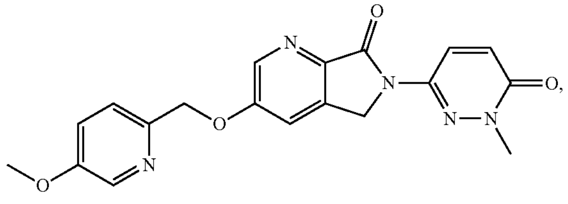

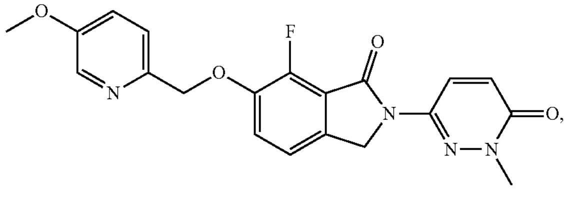

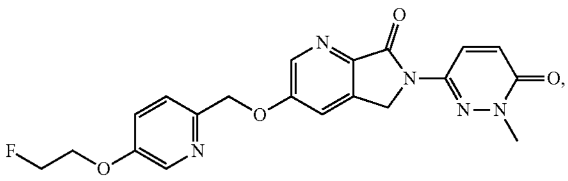

-continued

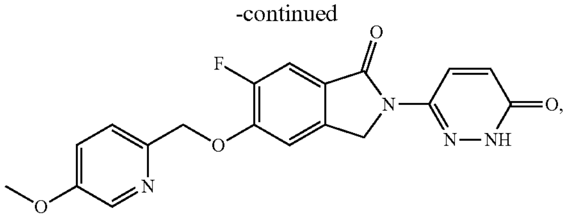

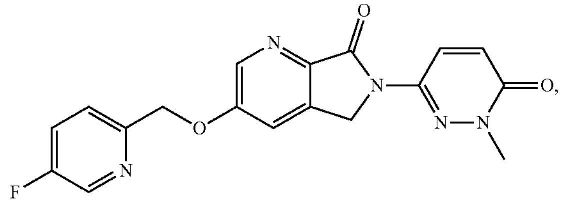

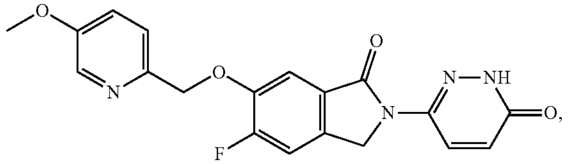

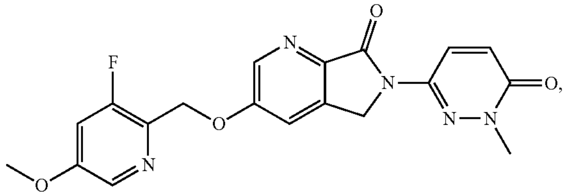

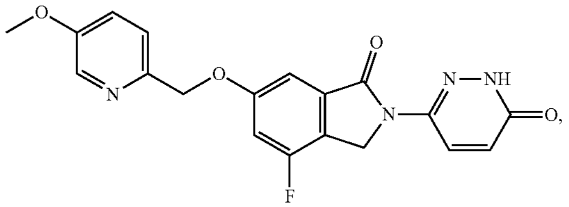

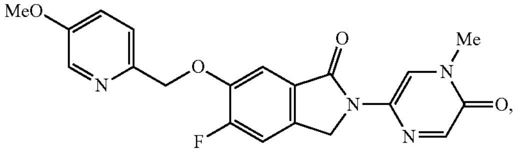

or

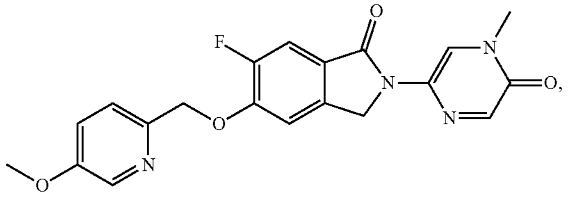 [SMILES: COc1ccc(COc2cc3c(cc2F)C(=O)N(c2cn(C)c(=O)cn2)C3)nc1]

or an isotopically enriched analog, pharmaceutically acceptable salt, tautomer, stereoisomer, or a mixture of stereoisomers thereof, optionally wherein the compound is labeled with a radioactive isotope.

2. The compound of claim 1, wherein the compound is labeled with a radioactive isotope.

3. The compound of claim 2, wherein the compound contains a positron-emitting radioactive isotope selected from $^{11}C$, $^{13}N$, $^{15}O$, and $^{18}F$.

4. An imaging agent comprising the compound of claim 2, or an isotopically enriched analog, pharmaceutically acceptable salt, tautomer, stereoisomer, or a mixture of stereoisomers thereof.

5. A method of detecting a presence or absence of a protein susceptible to aggregation in an individual comprising administering an effective amount of the imaging agent of claim 4 to the individual, and generating an image of a body part or body area of the individual.

6. The method of claim 5, wherein the presence or absence of a protein aggregate corresponds to a presence or absence of a neurodegenerative disease.

7. The method of claim 6, wherein the neurodegenerative disease is selected from Alzheimer's disease, amyotrophic lateral sclerosis, Huntington's disease, Parkinson's disease, Prion disease, and spinocerebellar ataxias.

8. The method of claim 7, wherein the neurodegenerative disease is Huntington's disease (HD).

9. The method of claim 5, wherein generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof.

10. The method of claim 9, wherein generating an image comprises PET imaging.

* * * * *